United States Patent

Cama et al.

[11] Patent Number: 4,775,669
[45] Date of Patent: * Oct. 4, 1988

[54] 1-CARBA-2-PENEM-3-CARBOXYLIC ACID

[75] Inventors: Lovji D. Cama, Edison; Burton G. Christensen, Metuchen, both of N.J.

[73] Assignee: Merck & Co., Inc., Rahway, N.J.

[*] Notice: The portion of the term of this patent subsequent to Apr. 7, 1998 has been disclaimed.

[21] Appl. No.: 83,938

[22] Filed: Jul. 31, 1987

Related U.S. Application Data

[60] Continuation of Ser. No. 736,885, Jul. 12, 1985, abandoned, which is a division of Ser. No. 109,737, Jan. 4, 1980, Pat. No. 4,543,257, which is a continuation of Ser. No. 843,171, Oct. 19, 1977, abandoned, which is a continuation-in-part of Ser. No. 743,363, Nov. 19, 1976, abandoned.

[51] Int. Cl.$^4$ .................. C07D 487/04; A61K 31/40
[52] U.S. Cl. ..................................... 514/210; 540/350
[58] Field of Search ................ 540/350, 310; 514/210

[56] References Cited

U.S. PATENT DOCUMENTS 4,260,627  4/1981  Christensen et al. ............... 514/210
4,543,257  9/1985  Cama et al. .......................... 540/350

Primary Examiner—Nicholas S. Rizzo
Attorney, Agent, or Firm—Robert J. North; Hesna J. Pfeiffer

[57] ABSTRACT

Disclosed are 1-carba-2-penem-3-carboxylic acids of the following structure:

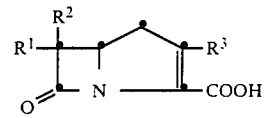

wherein $R^1$, $R^2$ and $R^3$ are, inter alia, independently selected from the group consisting of hydrogen, alkyl, aryl, and aralkyl. Such compounds as well as their pharmaceutically acceptable salt, ester and amide derivatives are useful as antibiotics. Also disclosed are processes for the preparation of such compounds, pharmacetical compositions comprising such compounds and methods of treatment comprising administering such compounds and compositions when an antibiotic effect is indicated.

27 Claims, No Drawings

1-CARBA-2-PENEM-3-CARBOXYLIC ACID

This is a continuation of application Ser. No. 736,885, filed 7/12/85, now abandoned, which in turn is a divisional of Ser. No. 109,737, filed 1/4/80, now U.S. Pat. No. 4,543,257, which in turn is a continuation of U.S. Ser. No. 843,171, filed Oct. 19, 1977 which is a continuation-in-part of U.S. Ser. No. 743,363 filed Nov. 19, 1976, both abandoned.

BACKGROUND OF THE INVENTION

This invention relates to 1-carba-2-penem-3-carboxylic acid and its 6-substituted, 6,6-disubstituted and 2-substituted derivatives, which compounds are useful as antibiotics and which may be represented by the following generic structural formula (I):

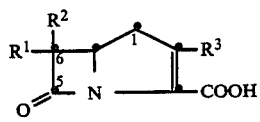

wherein $R^1$, $R^2$ and $R^3$ are independently selected from the group consisting of hydrogen, substituted and unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl and heterocyclylalkyl wherein the substituent or substituents relative to the above named radicals are selected from the group consisting of amino, hydroxy, alkoxyl, mercapto, alkylthio, arylthio, sulfamoyl, amidino, guanidino, nitro, chloro, bromo, fluoro, cyano and carboxy; and wherein the hetero atom in the above-named heterocyclic moiety is selected from the group consisting of oxygen, nitrogen and sulphur.

This invention also relates to the pharmaceutically acceptable salt, ester and amide derivatives of the compounds of the present invention identified by structure I, above.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only agsinst certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes.* and *B. subtilis,* and gram negative bacteria such as *E. coli, Pseudomonas, Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

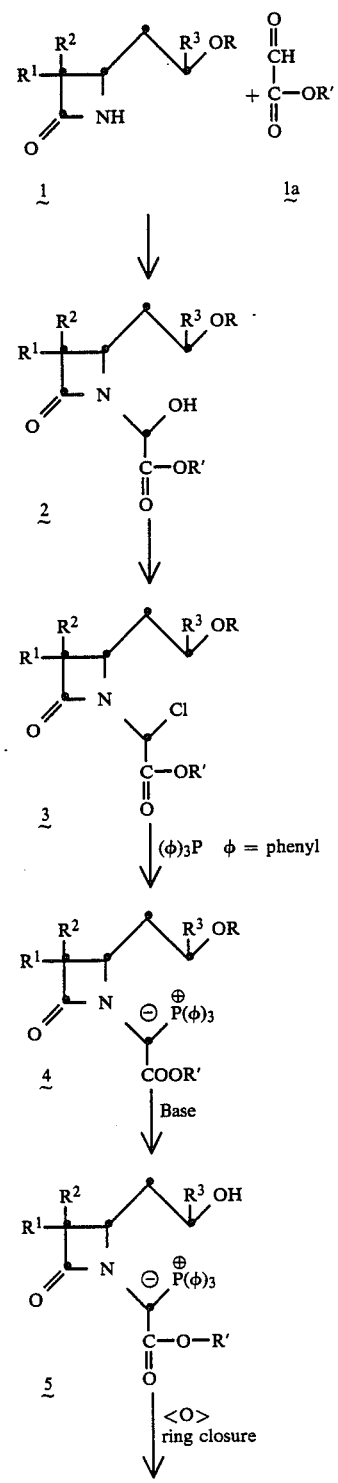

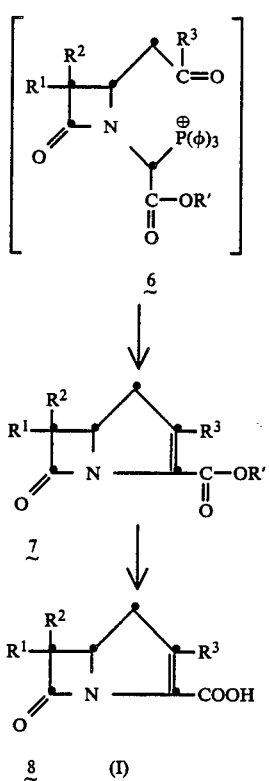

wherein

R¹, R² and R³ are as defined;

R and R' are readily removable blocking groups; R' may also be a pharmaceutically acceptable ester moiety. Typically, the blocking group R is an acyl such as a lower alkanoyl, aralkylcarbonyl or the like such as acetyl, bromo-t-butoxycarbonyl, benzyloxycarbonyl, formyl, trifluoroacetyl and the like or a trialkylsilyl such as trimethylsilyl or t-butyl dimethylsilyl group; and typically the blocking group R' is substituted or unsubstituted alkyl, aralkyl, alkenyl, or the like such as benzyl, p-nitrobenzyl, o-nitrobenzyl, pivaloyloxymethyl, bromo-t-butyl and the like.

In words relative to the above reaction diagram, a suitably substituted azetidinone (1) is reacted with a glyoxalate ester such as benzyl glyoxalate to form the corresponding 1-(benzyloxycarbonylhydroxymethyl)azetidinone (2). The reaction 1→2 is conveniently carried out in a solvent such as benzene, toluene, xylene and the like at a temperature of from about 25° C. to reflux for from 2 to 10 hours. There is no criticality as to the precise identity of the solvent, provided only that it adequately solubilizes the reactants and be inert or substantially inert to the desired course of reaction. The halogenation reaction 2→3 may be conducted by any of a variety of well-known halogenation means. Suitable reagents include: SOCl₂, POCl₃, oxalyl chloride and the like. A preferred means of chlorination involves treating 2 in a solvent such as tetrahydrofuran (THF), ether, CH₂Cl₂ and the like with thionylchloride in the presence of 1 to 2 equivalents (relative to the thionylchloride) of a base such as pyridine, triethylamine, quinoline and the like. Typically, the reaction is conducted at a temperature of from −30° to 25° C. for from 0.5 to 1 hour. The resulting 1-(benzyloxycarbonylchloromethyl)-azetidinone species, 3, is isolated, if desired, by conventional procedures for later reaction, 3→4. The intermediate 4 is prepared from 3 by treating 3 in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of from −20° to 25° C., for from 0.5 to 2 hours. The reaction 4→5 may be achieved by any of a variety of well-known deblocking procedures such as hydrolysis or hydrogenolysis. A particularly convenient means for the deblocking, 4→5, is by an alcoholysis procedure comprising treating 4 in a lower alkanol such as methanol, ethanol, or the like in the presence of 0.1 to 1.4 equivalents of the corresponding alkali metal alkoxide such as sodium methoxide or the like; typically the reaction is conducted at a temperature of from 0° to 25° C., for from 0.5 to 2 hours. The ring closure reaction 5→7 proceeds via the oxo intermediate 6 and is achieved by treating 5 with an equivalent of an oxidizing system such as 1:1 mixture of dimethylsulfoxide (DMSO) and acetic anhydride (Ac₂O); other oxidizing systems include cyclohexylcarbodiimide in DMSO, and CrO₃.2(pyridine) in CH₂Cl₂, for example. Typically, the closure step 5→7 is conducted at a temperature of from about 0° to 100° C. for from 0.25 to 24 hours in the oxidative system (DMSO/Ac₂O) described above or by heating from 100°–160° C. (after isolation of the oxo compound 6) in a solvent such as benzene, toluene, dioxane, xylene, or DMF. The carboxyl deblocking step 7→8 may be achieved by a number of well-known procedures such a hydrolysis, hydrogenation, or photolysis of a suitable R' group. Suitable hydrogenation catalysts for deblocking include the platinum metals and their oxides such as palladium on carbon and the like; suitable solvents for the hydrogenation include methanol, dioxane/H₂O, ethanol/H₂O and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

The glyoxalate esters 1a used to react with 1 can be prepared by oxidation of the corresponding tartaric acid diesters with oxidants such as periodic acid or lead tetraacetate in a solvent such as THF, benzene or methylene chloride at −20° to 25° for ¼ to 4 hrs. The tartarate esters are prepared from dilithio tartarate or disodio tartarate by reaction with R'X wherein X is chloro, bromo or iodo and R' is as defined above in a solvent such as DMF or DMSO at 25° to 70° C. for from 4 to 48 hrs. As noted above, R' may be a pharmaceutically acceptable ester moiety. Such pharmaceutically acceptable esters and amides, however, may also be prepared from the free acid of I according to the procedure of co-pending U.S. patent application Ser. No. 733,651 filed Oct. 18, 1976, which is directed to the pharmaceutically acceptable esters and amides of thienamycin and their preparation. Accordingly, for its disclosure relative to such pharmaceutically acceptable forms and their means of preparation, the above-cited application is incorporated herein by reference.

The substituted azetidinone 1 is disclosed and claimed in co-pending, concurrently filed U.S. patent application Ser. No. 743,370 Bouffard et al. [Merck & Co., Inc. Attorney's Docket Number 15959], which application is incorporated herein by reference for the disclosure relative to 1 and its preparation. The following diagram summarizes the synthesis of this essential starting material, 1.

Preparation of 1:

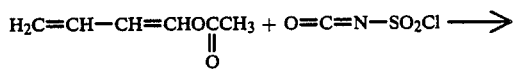

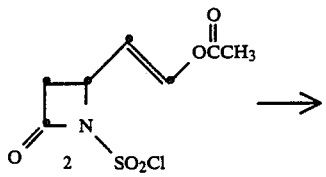

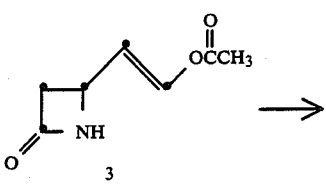

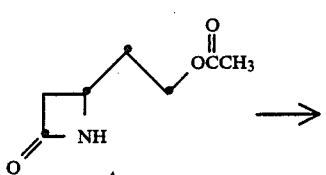

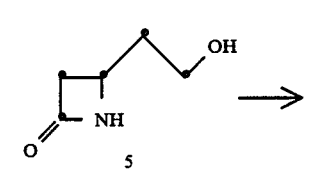

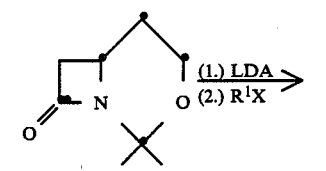

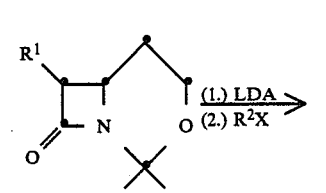

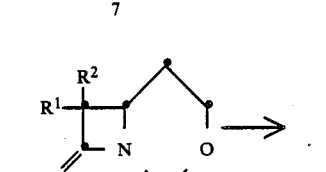

-continued

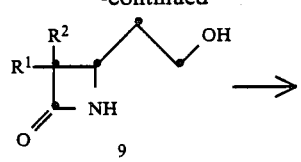

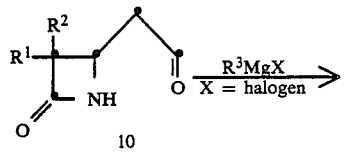

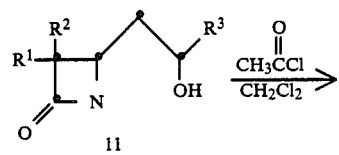

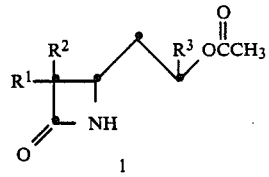

In words relative to the above diagram for the preparation of 1, the 4-(2-acetoxyvinyl)azetidine-2-one (3) is prepared by reacting chloro sulphonyl isocyanate and an acyloxybutadiene such as 1-acetoxybutadiene in a solvent such as anhydrous dimethyl ether at a temperature of from about −30° C. to 0° C. under a nitrogen atmosphere. The reaction intermediate 2 is converted to 3 by hydrolysis. The reduction of 3 to provide the 4-(2-acetoxyethyl)-2-azetidinone (4) is conducted by any convenient means such as hydrogenation in the presence of a catalyst such as platinum, palladium or oxides thereof under a hydrogen pressure of from 1 to 20 atmospheres in a solvent such as ethanol, ethylacetate, or the like at a temperature of from 0° to 25° C., for from 5 minutes to 1 hour. The 4-(2-hydroxyethyl)-2-azetidinone species, 5, is obtained from 4 by hydrolysis. The 8-oxo-2,2-dimethyl-3-oxa-1-azabicyclo[4.2.0]octane species, 6, is obtained on treatment of 5 with 2,2-dimethoxypropane in the presence of a catalyst such as boron trifluoride etherate in a solvent such as methylene chloride at a temperature of from 0° to 40° C. for from 1 to 40 minutes. Alternatively, 5 can be treated with borontrifluoride etherate and trimethylorthoformate to give 8-oxo-2-methoxy-3-oxa-1-azabicyclo[4.2.0]octane which can be mono- or dialkylated following the procedures for 6→7 or 8. Alkylation of 6 provides 7. Typically, 6 is treated with a strong base such as lithium diisopropyl amide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, R¹X, is added (R¹ is as described above and X is chloro or bromo; alternatively the alkylating agent may be R¹-tosylate, R¹-mesylate or an aldehyde or ketone such as acetaldehyde and the like) to provide mono-alkylated species 7. When desired dialkylated species 8 may be obtained from 7 by repeating the alkylating procedure, 6→7. Species 9 is obtained from 7 or 8 by acid hydrolysis. Oxidation of 9 with an oxidizing agent such as DMSO-acetic anhydride, pyridine.CrO₃, cyclohexylcarbodiimide/DMSO, and the like in a solvent such as DMSO, pyridine, acetonitrile, methylene chloride, and the like at a temperature of from about 0° to 25° C. for from 0.5 to 12 hours provides 10 which upon treatment with the Grignard reagent R³MgX (R³ is as defined above and X is halogen) provides 11. Typically, the alkylation reaction 10→11 is conducted in a solvent such as ether, THF, benzene and the like at a temperature of from −78° to about 25° C. for from 0.5 to about 24 hours.

The desired blocked-species 1 is obtained by treating 11 with an acylating agent such as acetyl chloride, formic acetic anhydride, trifluoroacetic anhydride and the like in a solvent such as CH₂Cl₂, CHCl₃, THF and the like at a temperature of from −20° to about 25° C. for from 0.5 to about 4 hours. The starting material 1 may be isolated for later reaction in accordance with the procedures of the present invention for the preparation of the compounds of the present invention.

It should be noted that in the establishment of R³ (9→10→11), the ring nitrogen may be protected by an easily removable blocking group R″:

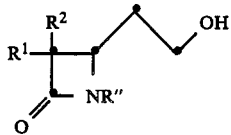

wherein R″ is acyl or triorganosilyl such as trimethylsilyl, t-butyldimethylsilyl, trifluoroacetyl, formyl, or the like. Removal of R″ is accomplished by hydrolysis to provide 11 (or 1 from N-blocked 1) according to well-known procedures.

Starting material 1, may alternatively be prepared by the following scheme:

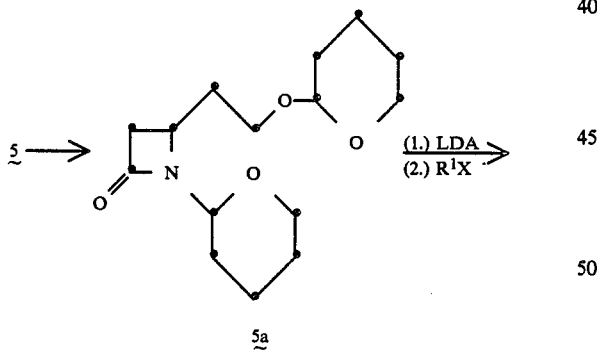

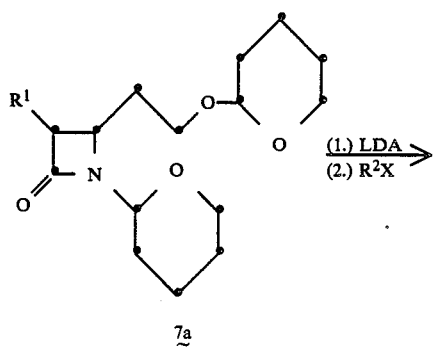

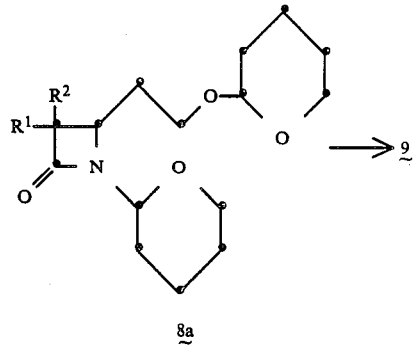

wherein all symbolism is as previously defined.

Reaction 5→5a is accomplished by treating 5 with 2,3-dihydropyran in a solvent such as p-dioxane, benzene, and the like in the presence of p-toluene sulphonic acid, perchloric acid, or the like at a temperature of from 0° to about 30° C. The intermediate 5a may be isolated for later alkylation to obtain 7a and 8a by procedures analogous to previously described reactions 6→7→8. Intermediate species 9 is obtained from 7a or 8a by mild acid hydrolysis.

Finally, it should be noted that intermediate species 9 may conveniently be prepared for later reaction in the above scheme by internal acylation according to the following reaction:

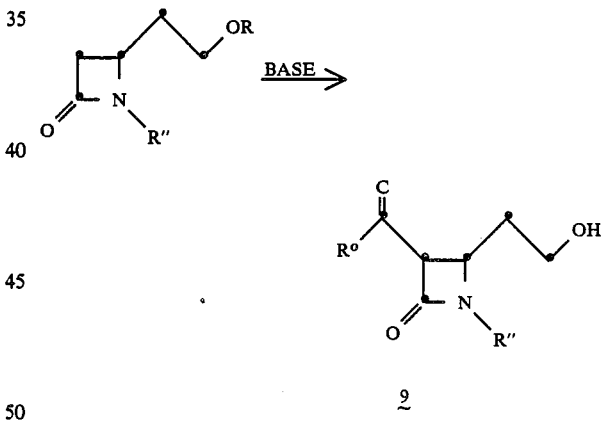

wherein R is acyl,

is R¹ and R° is for example lower alkyl, acyl, or the like. Typically the above reaction is conducted in a solvent such as tetrahydrofuran, ether, dimethoxyethane, or the like in the presence of 1 to 2 equivalents of a strong base such as lithium diisopropylamide, sodium hydride, potassium hydride or the like at a temperature of from −78° to 25° C., for from 0.5 to 24 hours.

An alternate procedure for establishing the 2-substituent, R³, in the total synthesis of I may be illustrated by the following reaction diagram:

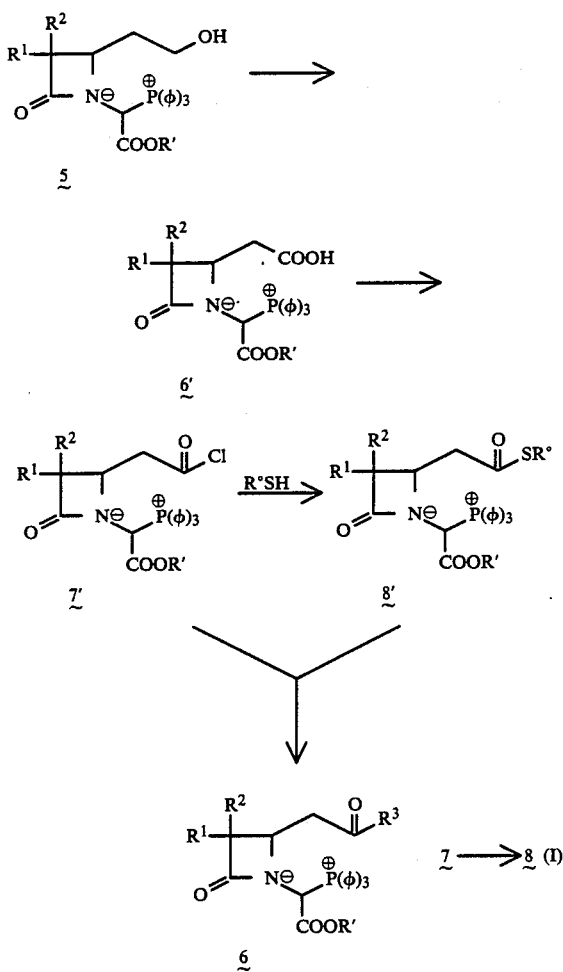

In words relative to the above diagram, species 5 is the same as that shown in the first-described reaction diagram except that R³ is hydrogen. This species, 5, is oxidized to yield 6'. Any of a variety of oxidizing systems may be employed such as Jones' Reagent, KMnO₄, Ag₂O, and the like in solvents such as acetone, aqueous THF, aqueous dioxane, and the like at a temperature range of from 0° to 25° C. for from 10 min. to 24 hours. The preferred conditions of oxidation, 5→6', comprise treating 5 in a solvent such as acetone, or the like with Jones' Reagent at a temperature of from 0° to 25° C. for from 10 min. to 0.5 hours. Chlorination of 6' yields 7'. Typically the chlorination is accomplished by treating 6' in a solvent such as CH₂Cl₂, THF, Et₂O, CHCl₃, C₆H₆, or the like with a chlorinating agent such as oxalyl chloride, SOCl₂, POCl₃, or the like at a temperature of from −20° to 25° C. for from ½ to 24 hours. Treating 7' with a mercaptan in R°SH such as phenyl mercaptan, butyl mercaptan, ethyl mercaptan, p-nitrophenyl mercaptan or the like in a solvent such as CH₂Cl₂, Et₂O, THF, C₆H₆, or the like at a temperature of from 0° to 25° C. for from 0.5 to 3 hours provides 8'. In the alternative 7' may be converted directly to 6, then to 7 and 8 (I). Conversion of either 8' or 7' to 6 is accomplished by treating either with (R³)₂CuLi⁻ or (R³)₂CuMgX wherein R³ is as defined above (the ultimate 2-substituent on species 8, otherwise known as I) in a solvent such as diethylether, tetrahydrofuran, or the like at a temperature of from −78° to 25° C. for from 10 min. to 2 hours. It will be recognized that species 6 (above) is identical to species 6 in the first-defined total reaction scheme and that conversion of 6→7→8 (I) is exactly as described above.

In the generic description of the present invention (I, above), the substituents R¹, R² and R³ are preferably selected from the group consisting of hydrogen; substituted and unsubstituted: straight and branched loweralkyl having from 1 to 10 carbon atoms; alkenyl, alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent (or substituents) relative to the above-named radicals is selected from the group consisting of amino, hydroxyl, cyano, carboxyl, nitro, chloro, bromo, fluoro, lower alkoxy having from 1 to 6 carbon atoms, mercapto, perhaloloweralkyl such as trifluoromethyl, lower-alkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

A particularly preferred class of compounds are those wherein R¹, R² and R³ are all hydrogen as well as those compounds wherein either R¹ or R² is hydrogen and R³ is selected from the group consisting of substituted and unsubstituted: loweralkyl having from 1 to 6 carbon atoms, alkenyl having from 2 to 6 carbon atoms, and phenyl; R¹ is an α-substituted alkyl wherein the α-substituent is hydroxyl, amino or mercapto and wherein the alkyl moiety is straight or branched and comprises 1 to 6 carbon atoms; the substituents relative to the above-named preferred radicals are selected from the group consisting of hydroxyl, amino, amidino, guanidino, phenyl, mercapto, carboxyl, trifluoromethyl, loweralkylthio and loweralkoxyl wherein the alkyl moiety of the loweralkylthio and loweralkoxyl comprises 1 to 6 carbon atoms.

The preferred esters used as protecting groups are those where R' is benzyl, p-nitrobenzyl, o-nitrobenzyl, t-butyl, bromo-t-butyl, t-butyl-dimethylsilyl, trimethylsilyl, trichloroethyl; or R' represents pharmaceutically acceptable ester moieties such as pivalyloxymethyl, allyl, methallyl, (2-methylthio)-ethyl, or 3-buten-1-yl.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried in certain species of I on side chains $R^1$, $R^2$ and $R^3$ are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel 1-carba-2-penem-3-carboxylic acids of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus*, *Escherichia coli*, *Klebsiella pneumoniae*, *Bacillus subtilis*, *Salmonella typhosa*, *Pseudomonas* and *Bacterium proteus*. The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylprrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All reaction temperatures are in °C.

EXAMPLE 1

Preparation of 1-carba-2-penem-carboxylic acid; and the benzyl ester and sodium salt thereof

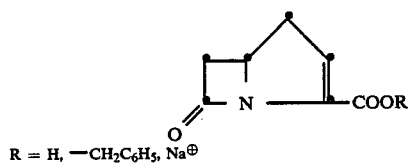

R = H, —CH$_2$C$_6$H$_5$, Na$^\oplus$

Step A:
1-(Benzyloxycarbonylhydroxymethyl)-4-(2-acetoxyethyl)-2-azetidinone

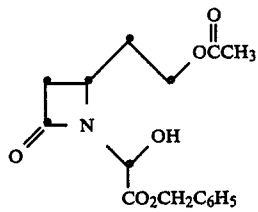

Dibenzyl tartarate, 2.0 g, is dissolved in 8 ml tetrahydrofuran (THF) and placed under N$_2$; periodic acid 1.7 g, dissolved in THF (80 ml) is added all at once and the reaction mixture is stirred vigorously for 30 minutes at 25° C. The resulting solution is filtered; the filtrate is evaporated; the residue is taken up in benzene (50 ml); filtered again; and finally evaporated to give benzylglyoxalate mixed with its hydrate. The 4-(2-acetoxyethyl)azetidinone, 1.0 g, is dissolved in benzene (80 ml) in a 3 neck flask fitted with a Dean-Stark water separator containing 2 g CaH$_2$ to trap the water, and a dropping funnel. The solution is refluxed until the CaH$_2$ shows no further reaction. The benzylglyoxalate and its hydrate from above is dissolved in benzene (80 ml) and added dropwise to the refluxing solution of the azetidinone over 1 hour; the reaction mixture is then refluxed another 3 hours. The reaction mixture is cooled and filtered. The filtrate is evaporated and the residue chromatographed on silica gel using 25% ethylacetate/benzene containing 1% methanol to give 1.85 g of product: 1-(benzyloxycarbonylhydroxymethyl)-4-(2-acetoxyethyl)-2-azetidinone. i.r. /μ: 2.8 (OH); 5.7 (broad, β-lactam ester carbonyl).

n.m.r. δ:

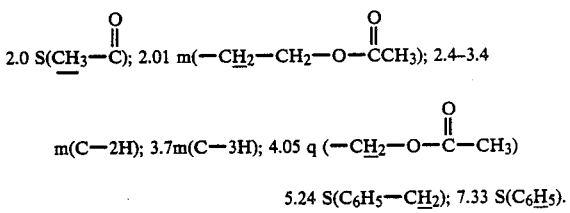

5.24 S(C$_6$H$_5$—C$\underline{H}_2$); 7.33 S(C$_6$$\underline{H}_5$).

Step B:
1-(Benzyloxycarbonylchloromethyl)-4-(2-acetoxyethyl)-2-azetidinone

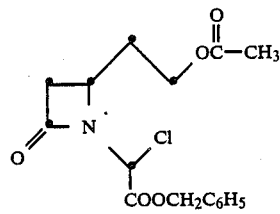

1-(Benzyloxycarbonyl hydroxymethyl)-4-(2-acetoxyethyl)-2-azetidinone (1.8 g) is dissolved in 30 ml THF under N$_2$ and cooled to −20° C. Pyridine 0.45 ml is added and then thionylchloride (0.390 ml in 4 ml THF) is added dropwise over 2 minutes. The reaction mixture is stirred at −20° C., for 5 minutes. The cooling bath is removed and the reaction mixture is stirred for another 25 minutes. The reaction mixture is diluted with 30 ml benzene and filtered. The filtrate is evaporated under reduced pressure at 5° C. The residue is 1-(benzyloxycarbonylchloromethyl)-4-(2-acetoxyethyl)-2-azetidinone which is used directly in the next reaction.

Step C:
1-(Benzyloxycarbonylmethylenetriphenylphosphoranyl)-4-(2-acetoxyethyl)-2-azetidinone

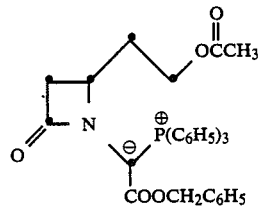

The 1-(benzyloxycarbonylchloromethyl)-4-(2-acetoxyethyl)-2-azetidinone (1.8 g) from Step B is dissolved in dimethylformamide (DMF) (20 ml) and treated with triphenylphosphine (1.47 g). The reaction mixture is stirred under N$_2$ at 25° C., for 1 hour. The DMF is removed under reduced pressure and the residue is taken up in CH$_2$Cl$_2$ and washed with pH 7 phosphate buffer. The CH$_2$Cl$_2$ solution is dried and evaporated to give the crude product. Chromatography on silica gel using ethylacetate as eluant gives 2.9 g 1-(benzoyloxycarbonylmethylenetriphenylphosphoranyl)-4-(2-acetoxyethyl)-2-azetidinone.

i.r. μ5.7(β-lactam, acetoxy ester); 6.1(benzyl ester).
n.m.r. δ:

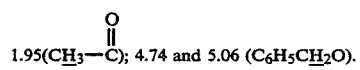

1.95(C$\underline{H}_3$—C); 4.74 and 5.06 (C$_6$H$_5$C$\underline{H}_2$O).

Step D:
1-(Benzyloxycarbonylmethyltriphenylphosphoranyl)-4-(2-hydroxyethyl)-2-azetidinone

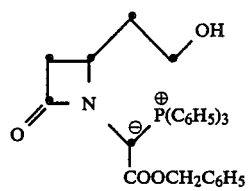

The 1-(benzyloxycarbonylmethylenetriphenylohosphoranyl)-4-(2-acetoxyethyl)-2-azetidinone (2.9 g) from Step C is dissolved in methanol (100 ml) and treated with 0.300 g of sodium methoxide. The reaction mixture is stirred under N$_2$ at 25° C., for 1 hour. Most of the methanol is removed under reduced pressure. The residue is taken up in 150 ml CH$_2$Cl$_2$ and washed once with pH 7 buffer, then dried and evaporated. The residue is chromatographed on silica gel using 5% methanol in ethylacetate as eluant to give 2.4 g of 1-(benzyloxycarbonylmethylenetriphenylphosphoranyl)-4-(2-hydroxyethyl)-2-azetidinone.

i.r. μ: 2.9 (OH); 5.72 (β-lactam) 6.1 (ester carbonyl).

Step E: Benzyl-1-carba-2-penem-3-carboxylate

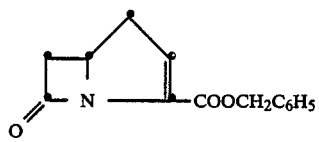

The 1-(benzyloxycarbonylmethylenetriphenylphosphoranyl)-4-(2-hydroxyethyl)-2-azetidinone (0.546 g) from Step D is dissolved in 10 ml dimethylsulfoxide (DMSO) and 10 ml of acetic anhydride is added. The reaction mixture is stirred under N$_2$ at 25° C., for 3.5 hours. The acetic anhydride and DMSO are removed under reduced pressure at 25° C., and the residue is purified by preparative thin layer chromatography on silica gel using 25% ethylacetate in benzene as eluant to give 0.081 g of benzyl-1-carba-2-penem-3-carboxylate.

U.V. λ$_{max}$ (H$_2$O/dioxane) 269, ε=5500.
M.S. M+ 243.

i.r. μ5.59 (β-lactam), 5.78 (ester), 6.19 (c═c). n.m.r. δ: 7.3 (C$_6$$\underline{H}_5$); 6.36 t(C-2H); 5.2 S(C$_6$H$_5$ C$\underline{H}_2$O) 4.2 m(C-5H); 2.5 to 3.7 m(C-6H and C-1H).

Step F: Sodium 1-carba-2-penem-3-carboxylate

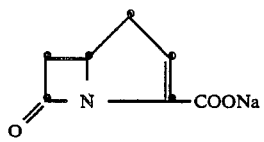

The Benzyl 1-carba-2-penem-3-carboxylate (0.010 g) from Step E is dissolved in 1 ml dioxane, treated with 1 ml H$_2$O and 0.01 ml pH 7 0.5 molar phosphate buffer; 0.002 g of 10% Pd/C catalyst is added and the reaction mixture is reduced under H$_2$ at 40 lbs for 7 minutes. The catalyst is filtered off and washed with water. The filtrate and washings are extracted with CH$_2$Cl$_2$ and the aqueous phase is concentrated and freeze dried to give sodium 1-carba-2-penem-3-carboxylate.

U.V. λ$_{max}$ 262 nm.

EXAMPLE 1a

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml. DMF and treated with o-nitrobenzyl chloride (20 g, 0.117 mole) and sodium iodide (17.5 g, 0.117 mole). The mixture is stirred under N$_2$ for 2½ days at 65° C.

The solvent is removed under vacuum and the resulting paste is treated with water and sodium thiosulfate (5 g). The resulting solid is filtered and dried to give di-o-nitrobenzyltartarate (17.0 g, 0.040 mole, 69%, m.p. 128° C.).

n.m.r. (DMSO)δ: 4.8 d (j=7, $\underline{H}$—C—OH), 5.23d (j=7, H—C—O$\underline{H}$), 5.75 S (O—C$\underline{H}_2$—C$_6$H$_4$—NO$_2$); 7.73 & 8.2 m (aromatic H).

Similar treatment of the di-lithium salt with R'X (where X=Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate. These can be used as alternatives to di-benzyl tartarate in Example 1.

EXAMPLE 2

Preparation of trans-3-isopropyl-4-(2-acetoxyethyl)-2-azetidinone

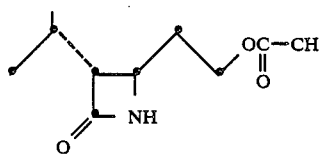

Step A:
8-oxo-2,2-dimethyl-7α-isopropyl-3-oxa-1-azabicyclo[4.2.0]octane

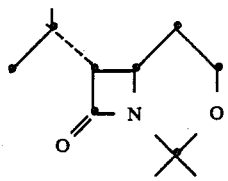

THF, 20 ml is placed under N₂, treated with 1.54 ml diisopropylamine and cooled to −78° C. A solution of n-butyl lithium 1.97M in hexane 5.6 ml is added dropwise over 5 min. The reaction mixture is stirred at −78° C. for 10 min and then treated with 8-oxo-2,2-dimethyl-3-oxa-1-azabicyclo[4.2.0]octane 1.55 g in 15 ml THF added dropwise over 5 min. After another 10 min hexamethylphosphoramide 1.97 ml is added. The mixture is stirred another 10 min, then treated with 2 ml of isopropyl iodide. The reaction mixture is stirred at −78° C. for 15 min and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C₆H₆ as eluant to give 8-oxo-2,2-dimethyl-7α-isopropyl-3-oxa-1-azabicyclo[4.2.0]octane. μ i.r.: 5.7 (β-lactam).

n.m.r. δ:

0.96d, 1.06d (CH₃—C—H); 1.4S, 1.76S (gem dimethyl);
  |
  CH₃

1.9m (C-5 H); 2.59d of d (C-7 H);

3.33m (C-6 H); 3.83 d of d (C-4 H).

Step B:
Trans-3-isppropyl-4-(2-hydroxyethyl)-2-azetidinone

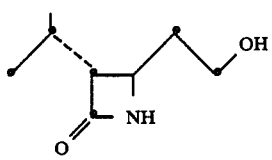

8-oxo-2,2-dimethyl-7α-isopropyl-3-oxa-1-azabicyclo[4.2.0]octane 1.0 g is dissolved in 8 ml of acetic acid and 2 ml H₂O is added. The mixture is heated at 65° C. for 1.25 hrs. The acetic acid and H₂O are removed under reduced pressure and the residue is taken up in C₆H₆ and evaporated to give 3-isopropyl-4-(2-hydroxyethyl)azetidinone.

Step C:
Trans-3-isopropyl-4-(2-acetoxyethyl)-2-azetidinone

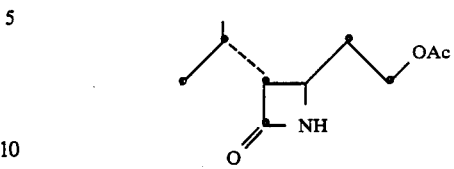

Trans-3-isopropyl-4-(2-hydroxyethyl)-2-azetidinone from Step B, is dissolved in 10 ml. CH₂Cl₂ and cooled to 0° C. Pyridine 0.75 ml is added and then 0.392 ml of acetyl chloride is added dropwise. The mixture is stirred at 0° for 15 min and then at 25° C. for another 15 minutes. The reaction mixture is evaporated to dryness. The residue is chromatographed on silica gel using 50% EtOAc/C₆H₆ as eluant to give 0.652 g 3-isopropyl-4-(2-acetoxyethyl)-azetidinone.

i.r. μ: 5.7 (broad β-lactam-ester carbonyl) 3.5 NH.
n.m.r. δ:

```
           CH₃               CH₃
            \                 \
1.0d, 1.1d (  CH); 2.0m (      CH and
            /                 /
           CH₃               CH₃
```

CH₂—CH₂—OAc); 2.63d (C-3 H); 3.43 d of t (C-4 H)

4.13t (CH₂—OAc), 7.03 (NH).

EXAMPLE 3
Preparation of
Trans-3-benzyl-4-(2-acetoxyethyl)-2-azetidinone

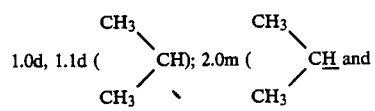

Step A:
8-oxo-2,2-dimethyl-7α-benzyl-3-oxa-1-azabicyclo[4.2.0]octane

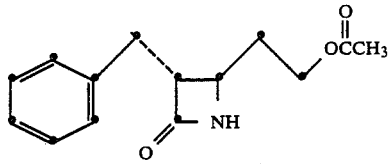

Following the procedure described for the preparation of 8-oxo-3-oxa-2,2-dimethyl-7α-isopropyl-1-azabicyclo[4.2.0]octane from 8-oxo-3-oxa-2,2-dimethyl-1-azabicyclo[4.2.0]octane and using benzyl bromide instead of isopropyl iodide there is obtained 8-oxo-2,2-dimethyl-7α-benzyl-3-oxa-1-azabicyclo[4.2.0]octane.

i.r. μ: 5.73 (β-lactam).

n.m.r. δ: 1.33S, 1.75S (gem dimethyl); 1.74m (C-5 H) 3.0 d of d (C₆H₅—CH₂); 3.73 d of d (C-2 H) 7.25S (C₆H₅).

Step B:
Trans-3-benzyl-4-(2-hydroxyethyl)-2-azetidinone

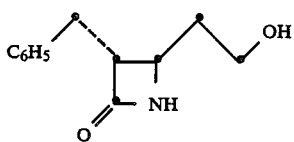

8-oxo-2,2-dimethyl-7α-benzyl-3-oxa-1-azabicyclo[4.2.0]octane (1.0 g) is dissolved in 8 ml acetic acid and 2 ml H₂O and heated at 65° C. for 1.25 hrs. The acetic acid and H₂O are removed under reduced pressure and the residue is taken up in C₆H₆ and evaporated to give trans-3-benzyl-4-(2-hydroxyethyl)-2-azetidinone.

Step C:
Trans-3-benzyl-4-(2-acetoxyethyl)-2-azetidinone

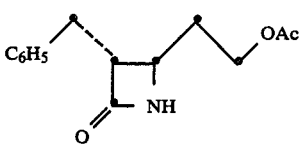

Trans-3-benzyl-4-(2-hydroxyethyl)-2-azetidinone is acetylated as described for the acetylation of trans-3-isopropyl-4-(2-hydroxyethyl)-2-azetidinone to give trans-3-benzyl-4-(2-acetoxyethyl)-2-azetidinone.

EXAMPLE 4

Preparation of Sodium 6α-(1-hydroxyethyl)-1-carba-2-penem-3-carboxylate

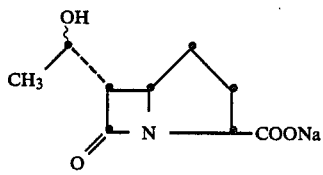

Step A: Benzyl 6α-(1-methylthiomethyleneoxy)ethyl-2-penem-3-carboxylate

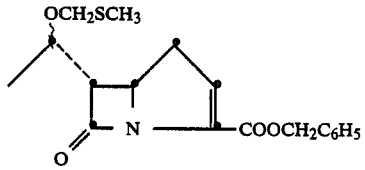

Following exactly the procedures described for conversion of trans-3-isopropyl-1-carba-4-(2-acetoxyethyl)-2-acetidinone to benzyl-6α-isopropyl-1-carba-2-penem-3-carboxylate, there is obtained benzyl-6α-(1-methylthiomethyleneoxy)ethyl-1-carba-2-penem-3-carboxylate from trans-3-(1-methyleneoxy)ethyl-4-(2-acetoxyethyl)-2-azetidinone.

i.r. μ5.6 (β-lactam); 5.79 (ester); 6.2 (C=C).

n.m.r. δ: 1.33d (CH₃—CH); 2.17s (CH₃ S); 2.85m (C-1 H); 3.4m (C-6 H); 4.2m (C-5H); 5.25s (C₆H₅CH₂) 6.45t (C-2 H); 7.35s (C₆H₅).

Step B: Benzyl 6α-(1-hydroxyethyl)-1-carba-2-penem-3-carboxylate

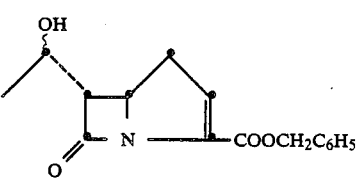

Benzyl 6α-(1-methylthiomethyleneoxy)-ethyl-2-penem-3-carboxylate (0.100 g) is dissolved in 4 ml acetonitrile 1 ml water. Mercuric chloride 1.5 eq is added and the mixture is stirred at 25° C. for 4 hrs. The reaction mixture is filtered through celite and washed with EtOAc. The filtrate and washings are washed with a solution of ammonium chloride then dried and evaporated. The residue is purified by preparative t.l.c. (50% EtOAc/C₆H₆, silica gel) to give Benzyl-6α-(1-hydroxyethyl)-2-penem-3-carboxylate.

Step C: Sodium 6α-(1-hydroxyethyl)-1-carba-2-penem-3-carboxylate

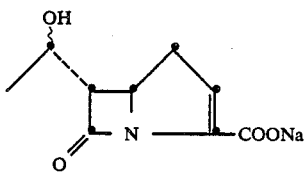

Benzyl 6α-(1-hydroxyethyl)-2-penem-3-carboxylate is hydrogenated using the procedure described in Step F, Example 1 to give sodium 6α-(1-hydroxyethyl)-2-penem-3-carboxylate.

EXAMPLE 5

Benzyl-6α-benzyl-2-penem-3-carboxylate

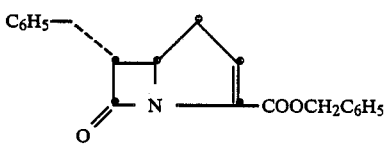

Following exactly the procedures described for conversion of trans-3-isopropyl-4-(2-acetoxyethyl)-2-azetidinone to benzyl-6α-isopropyl-2-penem-3-carboxylate one obtains benzyl-6α-benzyl-2-penem-3-carboxylate from trans-3-benzyl-4-(2-acetoxyethyl)-2-azetidinone.

i.r. μ: 5.59 (β-lactam); 5.79 (ester); 6.19 (C=C).

n.m.r. δ: 2.73m(C-1H); 3.2 d of d (C₆H₅—CH₂C); 3.5m(C-6H); 4.05 d of t (C-5H); 5.26s(C₆H₅CH₂—O) 6.4t(C-2H); 7.26s and 7.36s (C₆H₅).

Sodium-6α-benzyl-2-penem-3-carboxylate

Benzyl-6α-benzyl-2-penem-3-carboxylate is hydrogenated using the procedure described in Step F Example 1 to give sodium 6α-benzyl-2-penem-3-carboxylate.

EXAMPLE 6

Preparation of trans-3-(1-methylthiomethyleneoxy)-ethyl-4-(2-acetoxyethyl)-2-azetidinone

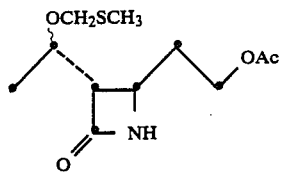

Step A:
8-oxo-2,2-dimethyl-7α-(1-hydroxyethyl)-3-oxa-1-azabicyclo[4.2.0]-octane

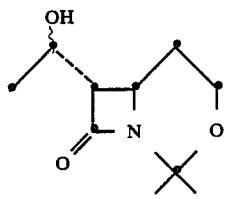

The lithium enolate of 8-oxo-3-oxa-2,2-dimethyl-1-azabicyclo[4.2.0]-octane is prepared as described in the preparation of 8-oxo-3-oxa-2,2-dimethyl-7α-isopropyl-1-azabicyclo[4.2.0]-octane. The enolate at −78° C. is treated with excess acetaldehyde at 78° C. and the reaction mixture is allowed to warm to 25° C. and stirred for 15 minutes. Work up as described before gives 8-oxo-3-oxa-2,2-dimethyl-7α-(1-hydroxyethyl)-1-azabicyclo[4.2.0]-octane.

i.r. μ: 2.9 (OH); 5.73 (broad β-lactam).

n.m.r. δ: 1.29 d (C$\underline{H}_3$—CH—); 1.41-1.75 s (gem dimethyl); 1.85 m (C-5 $\underline{H}$); 2.85 m (C-7 H); 3.85 d of d (C-4 H); 4.1 m (CH$_3$—C$\underline{H}$—O) 3.6 m (C-6 H).

Step B:
8-oxo-2,2-dimethyl-7α-(1-methylthiomethyleneoxy)ethyl-3-oxa-1-azabicyclo[4.2.0]-octane

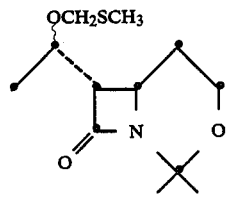

8-oxo-3-oxa-2,2-dimethyl-7α-(1-hydroxyethyl)-1-azabicyclo[4.2.0]-octane (1.04 g) is dissolved in 5 ml DMF under N$_2$ and treated with sodium hydride (0.330 g 57% in mineral oil, 1.5 eq). The reaction mixture is stirred for 1 hour. Chloromethylmethylsulfide (0.964 ml, 2-eq) is added and the reaction mixture is stirred another 2 hours. Acetic acid (0.5 ml) is added to destroy excess sodium hydride and the reaction mixture is evaporated to dryness under reduced pressure below 40° C. The residue is taken up in CH$_2$Cl$_2$, washed with water, dried and evaporated. The residue is chromatographed to give 8-oxo-2,2-dimethyl-7α-(1-methylthiomethyleneoxy)-ethyl-3-oxa-1-azabicyclo[4.2.0]-octane (0.275 g) and recovered starting material (0.435 g).

i.r. μ: 5.7 (β-lactam).

n.m.r. δ: 1.25 d (C$\underline{H}_3$—CH—); 1.42 and 1.73 s (gem dimethyl); 2.16S (CH$_3$-S); 1.85 m(C-5 H); 2.85 m (C-7 H); 3.83 d of d (C-4 H) 4.1 m (CH$_2$—C$\underline{H}$—); 4.81 d of d (O—C$\underline{H}_2$—S); 3.6 m (C-6 H).

Step C:
Trans-3-(1-methylthiomethyleneoxy)ethyl-4-(2-hydroxyethyl)-2-azetidinone

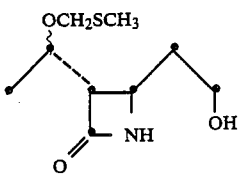

8-oxo-3-oxa-2,2-dimethyl-7α-(1-methylthiomethyleneoxy)ethyl-1-azabicyclo[4.2.0]-octane (0.460 g) is dissolved in 8 ml acetic acid and 2 ml H$_2$O and allowed to stand at 25° C. for 48 hrs. The acetic acid and H$_2$O are removed under reduced pressure. The residue is purified by preparative t.l.c. to give trans-3-(1-methylthiomethyleneoxy)ethyl-4-(2-hydroxyethyl)-2-azetidinone.

Step D:
Trans-3-(1-methylthiomethyleneoxy)ethyl-4-(2-acetoxyethyl)-2-azetidinone

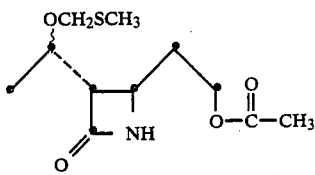

Trans-3-(1-methylthiomethyleneoxy)ethyl-4-(2-hydroxyethyl)-2-azetidinone is acetylated as described in the preparation of trans-3-(isopropyl)-4-(2-acetoxyethyl)-2-azetidinone to give trans-3-(1-(methylthiomethyleneoxy)ethyl-4-(2-acetoxyethyl)-2-azetidinone.

i.r. μ3.0 NH; 5.7 (broad, β-lactam-ester carboxyls).

n.m.r. δ:

1.3 d (C$\underline{H}_3$—CH); 1.8 m (C$\underline{H}_2$—CH$_2$—O—$\overset{\overset{\displaystyle O}{\|}}{C}$—);

2.06 S (C$\underline{H}_3$C$\overset{\overset{\displaystyle O}{\|}}{}$); 2.16 S (C$\underline{H}_3$S—); 3.0 m (C-3 H);

4.16 t (C$\underline{H}_3$—O$\overset{\overset{\displaystyle O}{\|}}{C}$); 4.7 d of d (O—C$\underline{H}_2$—S).

EXAMPLE 7

Preparation of Sodium-6α-isopropyl-1-carba-2-penem carboxylate

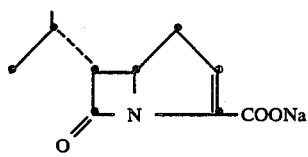

Step A:
Trans-1-(benzyloxycarbonylhydroxymethyl)-3-isopropyl-4-(2-acetoxyethyl)-2-azetidinone

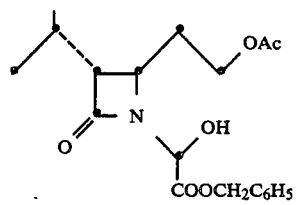

Benzyl glyoxalate is prepared from 0.390 g of dibenzyl tartarate as described in Example 1 Step A, dissolved in 30 ml $C_6H_6$ and refluxed using a Dean-Stark water separator containing 1 g of $CaH_2$ for 2 hours. Trans-3-isopropyl-4-(2-acetoxyethyl)-2-azetidinone (0.214 g) is added and the mixture is refluxed 8 hrs, cooled, filtered and evaporated. The residue is purified by preparative t.l.c. to trans-1-(benzyloxycarbonylhydroxymethyl)-3-isopropyl-4-(2-acetoxyethyl)-2-azetidinone (0.395 g).

i.r. μ: 2.9 (OH); 5.7 (broad β-lactam-ester carbonyls).

Step B:
Trans-1-(benzyloxycarbonylchloromethyl)-3-isopropyl-4-(2-acetoxymethyl)-2-azetidinone

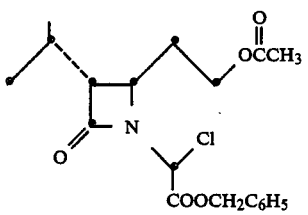

Trans-1-benzyloxycarbonylhydroxymethyl)-3-isopropyl-4-(2-acetoxyethyl)-2-azetidinone (0.395 g) is treated with pyridine (0.094 ml) and $SOCl_2$ (0.084 ml) following the procedure of Example 1, Step B to give the trans-1-(benzyloxycarbonylchloromethyl)-3-cso-propyl-4-(2-acetoxyethyl)-2-azetidinone which is used directly in the next reaction.

Step C:
Trans-1-(benzyloxycarbonylmethylenetriphenylphosphoranyl)-3-isopropyl-4-(2-acetoxyethyl)-2-azetidinone

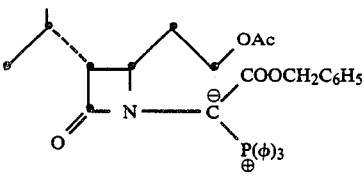

Trans-1-(benzyloxycarbonylchloromethyl)-3-isopropyl-4-(2-acetoxyethyl)-2-azetidinone from above is treated with 0.296 g of triphenylphosphine following the procedure of Example 1 Step E. to give trans-1-(benzyloxycarbonylmethylenetriphenylphosphoranyl)-3-isopropyl-4-(2-acetoxyethyl)-2-azetidinone.

n.m.r. δ:

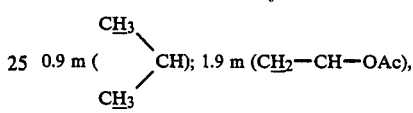

0.9 m ($CH_3$)(CH); 1.9 m ($CH_2$—CH—OAc), 1.98 s ($CH_3\overset{O}{\overset{\|}{C}}$) 2.63 d of d (C-3 H); 3.46 m (C-4 H);

4.03 g ($CH_2$—O—Ac) 5.13 s ($C_6H_5CH_2$) 7.26 s ($C_6H_5$)

Step D:
Trans-1-(Benzyloxycarbonylmethylenetriphenylphosphoranyl)-3-isopropyl-4-(2-hydroxyethyl)-2-azetidinone

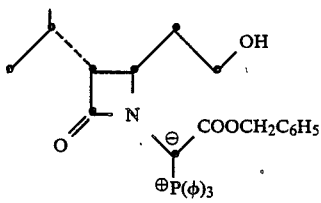

Trans-1-(benzyloxycarbonylmethylenetriphosphoranyl)-3-isopropyl-4-(2-acetoxyethyl)-2-azetidinone from the previous experiment is hydrolyzed using the procedure of Example 1, Step D to give trans-1-(benzyloxycarbonylmethylenetriphenylphosphoranyl)-3-isopropyl-4-(2-hydroxyethyl)-2-azetidinone (0.2/6 g).

Step E: Benzyl-6α-isopropyl-2-penem-3-carboxylate

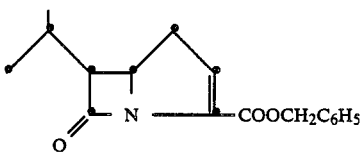

The trans-1-(benzyloxycarbonylmethylenetriphenylphosphoranyl)-3-isopropyl-4-(2-hydroxyethyl)-2-azetidinone 0.100 g is treated with DMSO and acetic anhydride following the procedure of Step E, Example 1 to give 0.026 g of benzyl-6α-isopropyl-2-penem-3-carboxylate.

i.r. μ: 5.6 (β-lactam); 5.79 (ester); 6.2 (C=C)
n.m.r. δ:

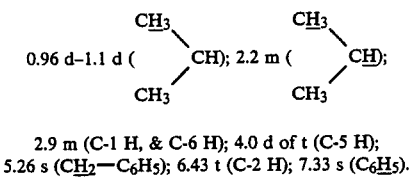

2.9 m (C-1 H, & C-6 H); 4.0 d of t (C-5 H);
5.26 s (C$\underline{H}_2$—C$_6$H$_5$); 6.43 t (C-2 H); 7.33 s (C$_6$H$_5$).

Step F: Sodium-6α-isopropyl-2-penem-3-carboxylate

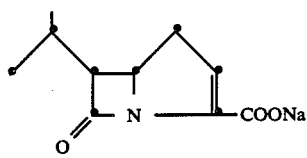

Benzyl 6α-isopropyl-2-penem-3-carboxylate is hydrogenated using the procedure described in Step F, Example 1 to give Sodium-6α-isopropyl-2-penem-3-carboxylate.

EXAMPLE 8

Preparation of 4-(2-Acetoxyethyl)-Azetidinone, 3-(1-hydroxyethyl)-4-(2-acetoxyethyl)-Azetidinone, and 3-(1-hydroxyethyl)-4-(2-hydroxyethyl)-Azetidinone Step A Preparation of 4-(2-acetoxyvinyl)azetidine-2-one

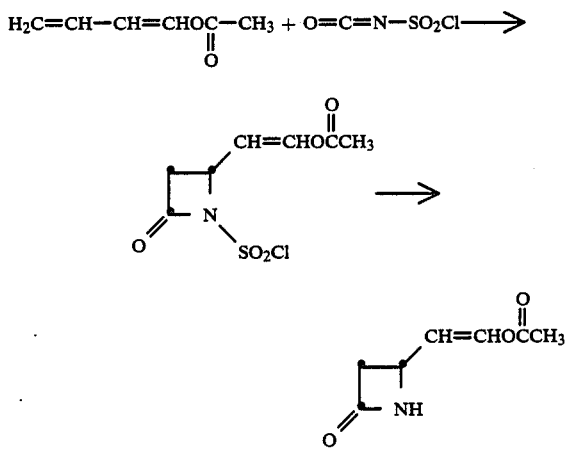

A solution of 1.0 ml distilled chlorosulfonylisocyanate (1.65 g; 11.7 mmoles) in 2.5 ml anhydrous diethyl ether is cooled under N$_2$ in a −20° C. bath.

A solution of 2.5 g 1-acetoxybutadiene (22 mmoles) in 2.5 ml anhydrous ether is similarly cooled under N$_2$ in a −20° C. bath.

The chlorosulfonylisocyanate solution is added dropwise to the acetoxybutadiene solution by means of a Teflon tube immersed in the CSI solution and pressurized with N$_2$. The addition takes 10 minutes. Little or no color is seen and the reaction is stirred at −20° C. for 0.5 hour. The solution is clear and has a light yellow color.

A solution of 2 g sodium sulfite and 5 g K$_2$HPO$_4$ in 20 ml H$_2$O is prepared during the above 0.5 hour reaction time and is cooled in an ice bath; 20 ml of ether is added and the mixture is vigorously stirred in an ice bath. At the end of the 30 minute reaction time, the reaction mixture is transferred, again using N$_2$ pressure and the Teflon tube, from the reaction flask which is maintained in the −20° C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish-orange gum with the aqueous phase. The ether phase is dried directly with MgSO$_4$. The aqueous/gum phase is extracted three more times with 50 ml portions of ether, each being added to the initial ether/MgSO$_4$.

The dried extracts are filtered and concentrated under a N$_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a N$_2$ stream. The product crystallizes from fractions 4–6, with traces in 3 and 7. Fractions 1–3 contain a yellowish sharp-smelling material which resinifies on standing. Yield: 100 mg as a mixture of the cis and trans isomers.

Step B

Preparation of 4-(2-Acetoxyethyl)-2-Acetidinone

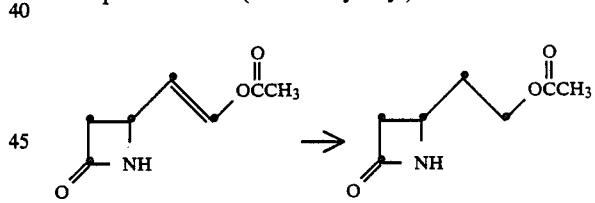

A solution of 4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-(2-acetoxyethyl)-2-azetidinone (10.0 g) as a crystalline solid. Recrystallization from ether affords white crystals: M.P. 44°–7°; ir (CHCl$_3$)μ5.66, 5.74; nmr (CDCl$_3$) τ 3.44 (broad s, 1, NH), 5.82 (m, 2, C$\underline{H}_2$OCOCH$_3$), 6.29 (m, 1, C-4H), 6.87 (½ AB pattern further split in four by C-4H and NH, 1, J$_{gem}$=12.8 Hz, J=4.5H J$_{NH}$=1.9 Hz, 7.38 (½ AB pattern further split in four by C-4H and NH, 1, J$_{gem}$=12.8 Hz, J=2.3 Hz, J$_{NH}$=1.0 Hz), 7.93 and 8.02 (s on m, total 5, OCOC$\underline{H}_3$ and C$\underline{H}_2$CH$_2$OCOCH$_3$, respectively).

Step C

Preparation of 4-(2-Hydroxyethyl)-2-Azetidinone

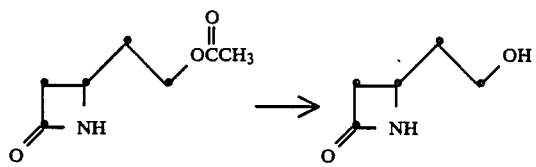

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/CHCl₃ to give 1.55 g of the alcohol: m.p. 50°; ir (CHCl₃) $\mu$5.67; nmr (CDCl₃) $\tau$ 3.20 (broad s, 1, NH), 6.24 and 6.28 (m on t, total 3, C-4H and C$\underline{H}_2$OH respectively), 6.90 (broad s on ½ AB pattern further split in four by C-4H and NH, total 2, OH and C-3H respectively, $J_{gem}$=13.0 Hz, $J_{vic}$=4.2 Hz, $J_{NH}$=1.6 Hz), 7.42 (½ AB pattern further split in four by C-4H and NH, 1, C-3H, $J_{gem}$=13.0 Hz, $J_{vic}$=2.2 Hz, $J_{NH}$=1.1 Hz), 8.16 (m, 2, C$\underline{H}_2$CH₂OH).

Step D

Preparation of 8-Oxo-2,2-dimethyl-3-oxa-1-azabicyclo[4.2.0]octane

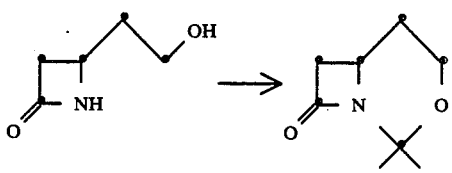

A solution of 4-(2-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]-octane (1.59 g) as a crystalline solid. Recrystallization from ether/hexane gives product of m.p. 60°–1°.

ir (CHCl₃)$\mu$: 5.73 ($\beta$-lactam).
nmr (CDCl₃)$\tau$:

| | |
|---|---|
| 6.02–6.28, m, 2H, C-4 methylene | |
| 6.22–6.62, m, 1H, C-6 methine | |
| 6.90, dd, 1H, $J_{7,7}$ = 14Hz, $J_{6,7}$ = 4.5Hz C-7 proton cis to C-6H | |
| 7.47, dd, 1H, $J_{7,7}$ = 14Hz, $J_{6,7}$ = 2Hz C-7 proton trans to C-6H | |
| 7.82–8.68, m, 2H, C-5 methylene | |
| 8.23, s, 3H | C-2 methyls |
| 8.57, s, 3H | |

Step E

Preparation of 8-oxo-2,2-dimethyl-7α and $\beta$-(1-hydroxyethyl)-3-oxa-1-azabicyclo/4.2.0/octane

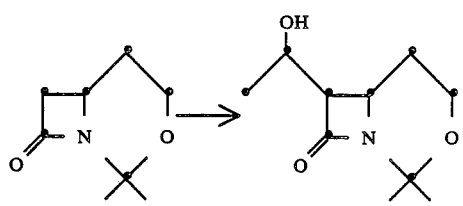

To a solution of 1.1 equivalents of freshly prepared lithium diisopropylamide in anhydrous tetrahydrofuran under a nitrogen atmosphere at −78° is added a solution of 8-oxo-2,2-dimethyl-3-oxa-1-azabicyclo[4.2.0]octane in anhydrous tetrahydrofuran which has been cooled to −78° C. After two minutes, the resulting lithium enolate is treated with excess acetaldehyde. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2-dimethyl-7α and $\beta$-(1-hydroxyethyl)-3-oxa-1-azabicyclo[4.2.0]octane.

Data for 8-oxo-2,2-dimethyl-7$\beta$-(1-hydroxyethyl)-3-oxa-1-azabicyclo[4.2.0]octane:
ir (CH₂Cl₂)$\mu$: 5.72$\mu$ ($\beta$-lactam).
nmr (CDCl₃)$\tau$:

| | |
|---|---|
| 5.53–6.43, m, 4H, C-4 methylene + C-6 methine + C-9 methine | |
| 6.90, dd on broad s, 2H, $J_{7,9}$ = 9Hz $J_{6,7}$ = 5.5Hz, C-7 methine + OH | |
| 7.70–8.83, m, 2H, C-5 methylene | |
| 8.27, s, 3H | C-2 methyl |
| 8.60, s, 3H | |
| 8.78, d, 3H, $J_{9,10}$ = 6.5Hz, C-10 methyl | |

Data for 8-oxo-2,2-dimethyl-7α-(1-hydroxyethyl)-3-oxa-1-azabicyclo[4.2.0]octane:
ir (CHCl₃)$\mu$: 2.9 broad O—H; 5.73 $\beta$-lactam.
nmr (acetone-d₆)$\delta$:

| | |
|---|---|
| 4.23–3.33, m, C-9 methine + C-4 methylene + C-6 methine | |
| 3.33, broad s, OH | |
| 2.83, dd, J = 2Hz, 6Hz | C-7 methine |
| 2.67, dd, J = 2Hz, 8Hz | |
| 1.93–1.63, m, C-5 methylene | |
| 1.63, s | C-2 methyls |
| 1.40, s | |
| 1.23, d, J = 6.5Hz, C-10 methyl | |

Step F

Preparation of 8-Oxo-2,2-dimethyl-7α-(1-p-nitrobenzylcarbonyldioxyethyl)-3-oxa-1-azabicyclo[4.2.0]octane

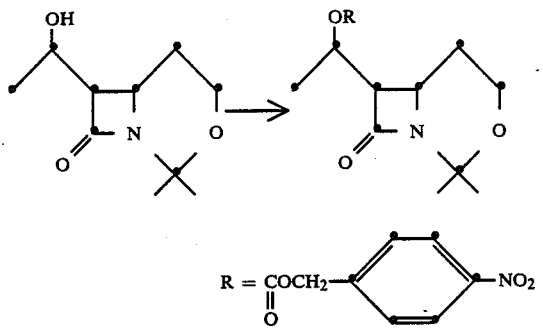

R = COCH₂—⟨C₆H₄⟩—NO₂
       ‖
       O

Under anhydrous conditions at 0° C. a solution of 8-oxo-2,2-dimethyl-7α-(1-hydroxyethyl)-3-oxa-1-azabicyclo[4.2.0]octane (60 mg, 0.302 mmole) in 0.6 ml ether is treated with powdered potassium hydroxide (19 mg, 0.332 mmole). After a period of 15 minutes, p-nitrobenzyl chloroformate (65 mg, 0.302 mmole) is added to the reaction mixture. Stirring is continued at 25° C. for an additional 15 hours. The mixture is partitioned between 1M pH 7 phosphate buffer and more ether. The ether phase is washed with water and brine, dried over magnesium sulfate and filtered. Evaporation of the filtrate under reduced pressure gives 67 mg of a colorless oil. Purification by preparative thick-layer chromatography on silica gel developing with 1:9 ethyl acetate/benzene gives 8-oxo-2,2-dimethyl-7α-(1-p-nitrobenzylcarbonyldioxyethyl)-3-oxa-1-azabicyclo[4.2.0]octane (40 mg) as a mixture of diastereomers.

ir (CH₂Cl₂) μ: 5.68 (β-lactam and carbonate), 6.19 and 6.54 (nitro).

nmr(CDCl₃)τ: 1.67, d, 2H, ArH 2.37, d, 2H, ArH 4.67, s, 2H, ArCH₂ 4.67–5.22, m, CH₃CH 5.98–6.25, m, 2H, C-4 methylene 6.25–6.62, m, 1H, C-6 methine 6.75–7.12, m, 1H, C-7 methine 7.75–8.83, m, 2H, C-5 methylene 8.22, s, 3H, C-2 methyl 8.50–8.58, m, 5H, C-2 methyl+CH₃CH The 7β-diastereoisomers or the 7α and β-mixture are obtained in an analogous manner.

Step G

Preparation of Cis and Trans-3-(1-p-nitrobenzylcarbonyldioxyethyl)-4-(2-hydroxyethyl)-2-azetidinone

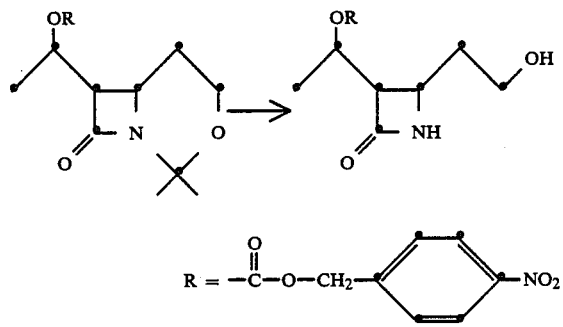

R = —C—O—CH₂—⟨C₆H₄⟩—NO₂
    ‖
    O

8-Oxo-3-oxa-2,2-dimethyl-7α-(1-p-nitrobenzylcarbonyldioxyethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give trans-3-(1-p-nitrobenzylcarbonyldioxyethyl)-4-(2-hydroxyethyl)-2-azetidinone as a mixture of diastereoisomers.

ir (CH₂Cl₂)μ: 5.67 (β-lactam), 5.72 shoulder, 6.20 and 6.57 (nitro).

nmr (CDCl₃) τ: 1.73, d, 2H, J=8.5 H, ArH 2.43, d, 2H, J=8.5 Hz, ArH 3.63, broad s, 1H, NH 4.37–5.13, m, 1H, CH₃CH 4.72, s, 2H, ArCH₂ 6.07–6.53, m, 1H, C-4 methine 6.23, t, 2H, J=5.5 Hz, CH₂OH 6.73–6.93, m, 1H, C-3 methine 7.63–8.97, m, 3H, CH₂CH₂OH 8.53, d, J=6.5 Hz, CH₃CH.

The cis diastereoisomers or the cis-trans mixture are obtained in an analogous manner.

Hydrogenation of 3-(1-p-nitrobenzylcarbonyldioxyethyl)-4-(2-hydroxyethyl)-2-azetidinone according to the procedure of Example 1 Step F provides 3-(1-hydroxyethyl)-4-(2-hydroxyethyl)-2-azetidinone, which upon acetylation according to the procedure of Example 2, Step C provides 3-(1-hydroxyethyl)-4-(2-acetoxyethyl)-2-azetidinone; or acetylation by the procedure of Example 2, Step C provides 3-(1-p-nitrobenzylcarbonyldioxyethyl)-4-(2-acetoxyethyl)-2-azetidinone.

Steps D', E', F' and G' as alternative to Steps D, E, F, and G for the preparation of 3-(1-p-nitrobenzylcarbonyldioxyethyl)-4-(2-hydroxyethyl)azetidinone

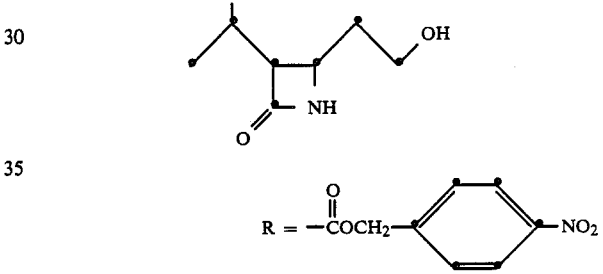

R = —COCH₂—⟨C₆H₄⟩—NO₂
    ‖
    O

Step D'

Preparation of 1-(2-Tetrahydropyranyl)-4-[2-(2-tetrahydropyranyl)oxyethyl]-2-azetidinone

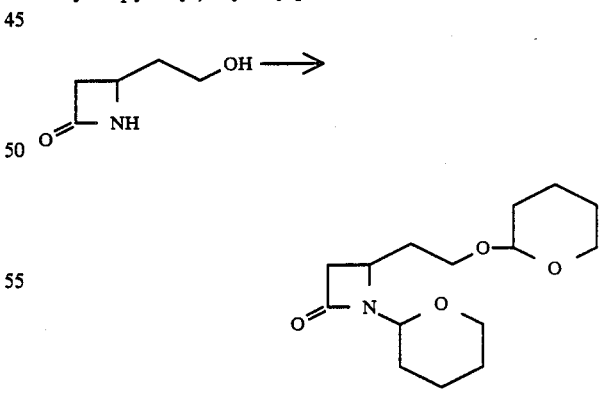

Under nitrogen and at 25° C., a solution of 4-(2-hydroxyethyl)-2-azetidinone (62 mg, 0.539 mmole) in 0.5 ml of anhydrous p-dioxane is treated with 2,3-dihydropyran (0.98 ml, 1.08 mmoles) and p-toluenesulfonic acid monohydrate (19 mg, 0.10 mmole). The resulting solution is stirred for a period of 60 minutes and then partitioned between 10 ml of 0.5M pH7 phosphate buffer and 10 ml of ethyl acetate. The aqueous phase is extracted a second time with ethyl acetate. The combined ethyl acetate solutions are washed with brine, dried over magnesium sulfate and filtered. The filtrate is evaporated unnder reduced pressure to give 216 mg of crude product. Purification by preparation thick-layer chromtography developing with ethyl acetate gives 80 mg of 1-(2-tetrahydropyranyl)-4-[2-(2-tetrahydropyranyl)oxyethyl]-2-azetidinone as an oil.

nmr (CDCl₃) τ:

---

5.13–5.60, m, OCH
5.83–6.85, m, C-4H + OCH₂
6.95, dd, J = 5Hz and 15 Hz  ⎫
7.35, dd, J = 3Hz and 15 Hz  ⎬ C-3 methylene
7.62–8.95, m, CHCH₂CH₂CH₂CH₂ + CHCH₂CH₂O

---

Step E'

Preparation of Cis and Trans-1-(2-tetrahydropyranyl)-3-(1-hydroxyethyl)-4-[2-(2-tetrahydroopyranyl)oxyethyl]-2-azetidinone

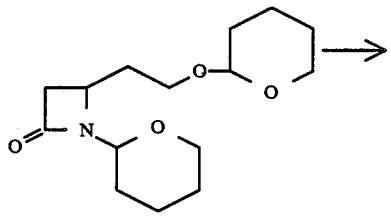

Following the procedure described for the preparation of 8-oxo-2,2-dimethyl-7α and β-(1-hydroxyethyl)-3-oxa-1-azabicyclo[4.2.0]octane from 8-oxo-2,2-dimethyl-3-oxa-1-azabicyclo[4.2.0]octane and using 1-(2-tetrahydropyranyl)-4-[2-(2-tetrahydropyranyl)oxyethyl]-2-azetidinone one obtains a diastereomeric mixture of both cis and trans-1-(2-tetrahydropyranyl)-3-(1-hydroxyethyl)-4-[2-(2-tetrahydropyranyl)oxyethyl]-2-azetidinone.

Step F'

Preparation of Cis and Trans-1-(2-tetrahydropyranyl)-3-(1-p-nitrobenzylcarbonyldioxyethyl)-4-[2-(2-tetrahydropyranyl)oxyethyl]-2-azetidinone

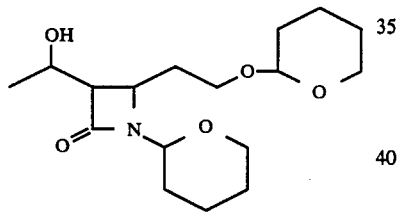

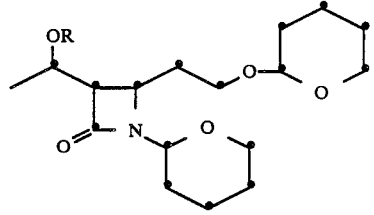

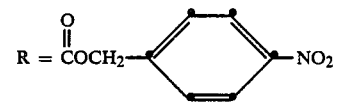

Following the procedure described for the preparation of 8-oxo-2,2-dimethyl-7α-(1-p-nitrobenzylcarbonyldioxyethyl)-3-oxa-1-azabicyclo[4.2.0]octane from 8-oxo-2,2-dimethyl-7α-(1-hydroxyethyl)-3-oxa-1-azabicyclo[4.2.0]octane and using trans-1-(2-tetrahydropyranyl)-3-(1-hydroxyethyl)-4-[2-(2-tetrahydropyranyl)oxyethyl]-2-azetidinone there is obtained trans-1-(2-tetrahydropyranyl)-3-(1-p-nitrobenzylcarbonyldioxyethyl)-4-[2-(2-tetrahydropyranyl)oxyethyl]-2-azetidinone. The cis diastereoisomers are obtained in an analogous manner.

Step G'

Preparation of Cis and Trans-3-(1-p-nitrobenzylcarbonyldioxyethyl)-4-(2-hydroxyethyl)-2-azetidinone

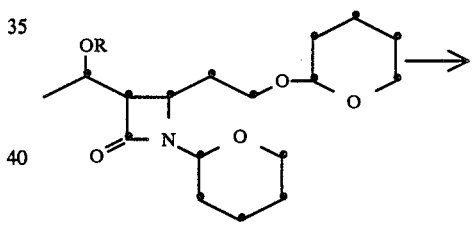

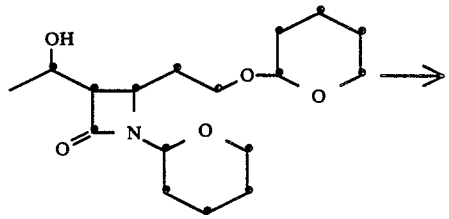

A solution of trans-1-(2-tetrahydropyranyl)-3-(1-p-nitrobenzylcarbonyldioxyethyl)-4-[2-(2-tetrahydropyranyl)oxyethyl]-2-azetidinone in methanol at 25° C. is treated with 0.1 molar equivalent of p-toluenesulfonic acid monohydrate. The solution is stirred for a period of 2 hours and then neutralized with 1M pH7 phosphate buffer. The product is extracted into ethyl acetate. The ethyl acetate solution is washed with brine, dried over magnesium sulfate and filtered. The filtrate is evaporated under reduced pressure to give trans-3-(1-p-nitrobenzylcarbonyldioxyethyl)-4-(2-hydroxyethyl)-2-azetidinone. The cis diastereoisomers are obtained in an analogous manner.

EXAMPLE 9

Preparation of 1-(t-butyldimethylsilyl)-4-(2-acetoxyethyl)-2-Azetidinone

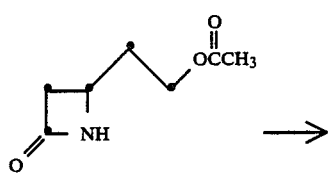

A solution of 4-(2'-acetoxyethyl)-2-azetidinone (50.2 g, 0.32 mole) and t-butyldimethylchlorosilane (50.6 g, 0.335 mole) in 250 ml anhydrous N,N-dimethylformamide is treated at 0° with triethylamine (35.6 g, 0.353 mole). A white precipitate appears immediately. The mixture is stirred for a period of five minutes. It is then partitioned between 1600 ml benzene and 600 ml water. The organic phase is washed an additional four times with water and finally with brine. The benzene solution is then dried over magnesium sulfate and filtered. Evaporation of the filtrate under reduced pressure gives 84.0 g of 1-(t-butyldimethylsilyl)-4-(2'-acetoxyethyl)-2-azetidinone. Recrystallization from pentane gives 68.9 g of product with m.p. 35°.

nmr (CDCl$_3$)$\tau$: 5.90, t, J=b 6 Hz, C$\underline{H_2}$OCOCH$_3$; 6.17–6.60, m, C-4 methine; 6.80, dd, J=1$\overline{4.5}$ Hz and 5 Hz, C-3 proton cis to C-4 methine; 7.33, dd, J=14.5 Hz and 3 Hz, C-3 proton trans to C-4 methine; 7.53–8.50, m, C$\underline{H_2}$CH$_2$OCOCH$_3$; 7.97, s, OCOC$\underline{H_3}$; 9.03, s, Si$\overline{C}$(CH$_3$)$_3$; 9.75, s, Si(CH$_3$)$_2$.

EXAMPLE 10

1-(t-butyldimethylsilyl)-4-(2-hydroxyethyl)-2-azetidinone

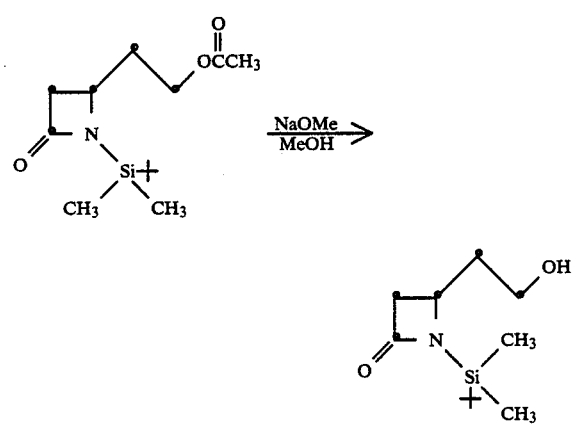

1-(t-butyldimethylsilyl)-4-(2-acetoxyethyl)-2-azetidinone (1.94 g, 7.15 mmol) is dissolved in anhydrous methanol (20 ml) cooled to 0° and a solution of NaOMe (0.36 mmol) in MeOH (0.5 ml) is added to the mixture stirred at 0° for 2 hours. HOAC (0.1 ml) is added the mixture is evaporated under vacuum and the residue is taken up in CH$_2$Cl$_2$; washed with water, 5% NaHCO$_3$, dried and evaporated to a pale yellow oil This is chromatographed on silica gel using EtOAc as eluant, to give 1-(t-butyldimethylsilyl)-4-(2-hydroxyethyl)-2-azetidinone 0.743 g (45%).

ir. μ2.85 (OH); 5.75, broad (β-lactam).

n.m.r. δ: 0.23, S, (CH$_3$Si); 0.96, S [(CH$_3$C-Si]; 2.0 m(C—C$\underline{H_2}$—CH$_2$OH) 3.0 m (C—3H+O$\underline{H}$); 3.64, t+m (C—4H+—C$\underline{H_2}$—OH).

ms: M$^+$ — 5$\overline{7}$(tBu) = 172.

EXAMPLE 11

1-(t-butyldimethylsilyl)-4-(2-oxoethyl)-2-azetidinone

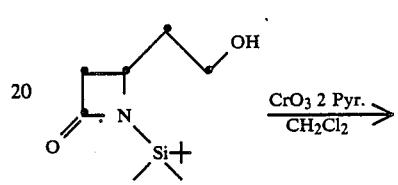

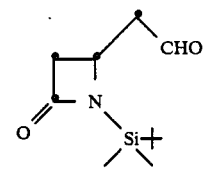

Anhydrous CrO$_3$ (1.94 g, 19.38 mmol) is added to a solution of anhydrous pyridine (3.07 g, 38.76 mmol) in anhydrous CH$_2$Cl$_2$ (50 ml). The resulting mixture is stirred at r.t. for 15 min. A solution of 1-(t-butyldimethylsilyl)-4-(2-hydroxyethyl)-2-azetidinone (0.74 g, 3.23 mmol) in anhydrous CH$_2$Cl$_2$ 5 ml is added all at once. After stirring for 5 min, the CH$_2$Cl$_2$ solution is separated from a dark gummy precipitate which is washed with more CH$_2$Cl$_2$. The combined CH$_2$Cl$_2$ solution is evaporated under vacuum. The residue is taken up in ether filtered and washed with 5% NaHCO$_3$, 5% HCl, 5%NaHCO$_3$ and brine then dried and evaporated to give the aldehyde (0.543 g 74%).

i.r., μ: 5.75 β-lactam and aldehyde.

n.m.r. δ: 0.23 S(CH$_3$ Si); 0.99 S [(CH$_3$)$_3$C—Si]; 3.0 m (C$\underline{H_2}$—CHO and C-$\overline{3}$H); 4.0 m(C-4$\overline{H}$); 9.76 t(C$\underline{H}$O).

EXAMPLE 12

1-(t-butyldimethylsilyl)-4-(2-hydroxypropyl)-2-azetidinone

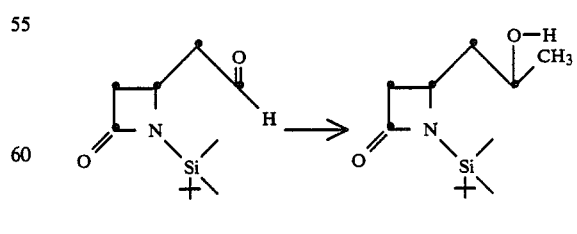

1-(t-butyldimethylsilyl)-4-(2-oxoethyl)-2-azetidinone (2.27 g, 0.01 mole) is dissolved in 50 ml ether and cooled to −20° C. under N$_2$. A solution of CH$_3$MgBr in ether (0.011 mole CH$_3$MgBr) is added dropwise over ½ hours at −20° C. and the reaction mixture is stirred for another ½ hr at −20°, allowing to rise to 25° C. The reaction mixture is treated with a saturated solution of MgSO4 (2 ml) and allowed to stir for 15 min. The Mg salts are filtered off and washed with ether. The combined filtrate and washings are dried and evaporated. Chromatography of the residue on silica gel gives 1-(t-butyldimethylsilyl)-4-(2-hydroxypropyl)-2-azetidinone.

EXAMPLE 13

1-(t-butyldimethylsilyl)-4-(2-azetoxypropyl)-2-azetidinone

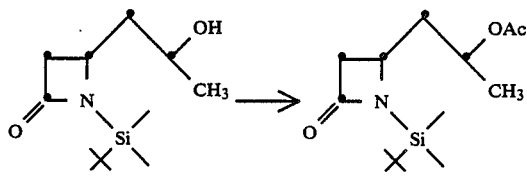

1-(t-butyldimethylsilyl)-4-(2-hydroxypropyl)-2-azetidinone (2.46 g) is dissolved in 20 ml CH2Cl2 cooled to 0° and treated with 0.90 g pyridine and 0.080 g of acetyl chloride (added dropwise). The reaction mixture is stirred at 0° for 15 min, allowed to warm to r.t. during the next 15 min and then worked up by dilution with CH2Cl2 and washed with water, drying and evaporating. The residue on chromatography on silica gel gives 1-(t-butyldimethylsilyl)-4-(2-acetoxypropyl)-2-azetidinone.

EXAMPLE 14

4-(2-acetoxypropyl)-2-azetidinone

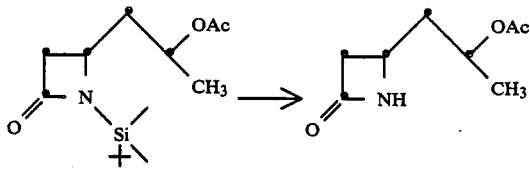

1-(t-butyldimethylsilyl)-4-(2-acetoxypropyl)-2-azetidinone (2.4 g) is dissolved in a solution of HCl in MeOH (0.25N, 10 ml) and allowed to stand 2.5 hours at room temperature. The solvent is evaporated under reduced pressure and the residue is chromatographed on silica gel to give 4-(2-azetoxypropyl)-2-azetidinone.

EXAMPLE 15

Preparation of 4-(2-acetoxy-2-p-methoxyphenyl)-ethyl-2-azetidinone

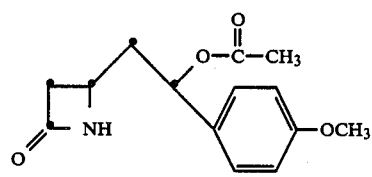

Treatment of 1-(t-butyldimethylsilyl)-4-(2-oxoethyl)-2-azetidinone (0.01 mole) with p-methoxyphenyl-magnesium bromide (1.1 eq.) in ether at 0° C. gives 2-azetidinone with p-methoxyphenyl-magnesium bromide gives 1-(t-butyl dimethylsilyl)-4-(2-hydroxyethyl-2-p-methoxyphenyl)-2-azetidinone which is acetylated as described before (Ex. 3, Step C) to give 4-(2-acetoxy-2-p-methoxyphenyl)-2-azetidinone.

EXAMPLE 16

Preparation of 4-(2-acetoxy-5-(1'-tetrahydropyranyloxy)pentyl-2-azetidinone

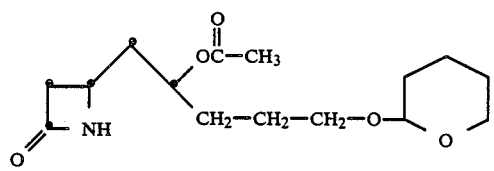

Treatment (following procedure of Example 15) of 1-(t-butyldimethylsilyl)-4-(2-oxoethyl)-2-azetidinone with Grignard reagent from 1-bromo-3-(2-tetrahydropyranyloxy)-propane followed by acetylation of the product gives 4-(2-acetoxy-5-(2'-tetrahydropyranyloxy)-pentyl-2-azetidinone.

EXAMPLE 17

Preparation of 8-Oxo-2,2-dimethyl-3-oxa-1-azabicyclo[4.2.0]octane

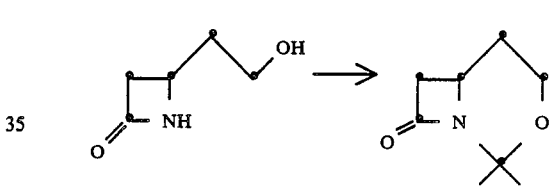

A solution of 4-(2'-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at room temperature. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]octane (1.59 g) as a crystalline solid. Recrystallization from ether/hexane gives product of m.p. 60°–1°.

ir (CHCl3)μ: 5.73 (β-lactam).

nmr (CDCl3)τ:

| | |
|---|---|
| 6.02–6.28, m, 2H, C-4 methylene | |
| 6.22–6.62, m, 1H, C-6 methine | |
| 6.90, dd, 1H, $J_{7,7} = 14H_z$, $J_{6,7} = 4.5H_z$, C-7 proton cis to C-6H | |
| 7.47, dd, 1H, $J_{7,7} = 14H_z$, $J_{6,7} = 2H_z$, C-7 proton trans to C-6H | |
| 7.82–8.68, m, 2H, C-5 methylene | |
| 8.23, s, 3H | C-2 methyls |
| 8.57, s, 3H | |

EXAMPLE 18

8-Oxo-2,2-dimethyl-7β-(1'-hydroxyethyl)-3-oxa-1-azabicyclo[4.2.0]octane

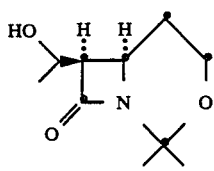

ir (CH$_2$Cl$_2$)μ: 5.72μ (β-lactam).
nmr (CDCl$_3$)τ:

| |
|---|
| 5.53–6.43, m, 4H, C-4 methylene + C-6 methine + C-9 methine |
| 6.90, dd on broad s, 2H, J$_{7,9}$ = 9H$_z$, J$_{6,7}$ = 5.5H$_z$, C-7 methine + OH |
| 7.70–8.83, m, 2H, C-5 methylene |
| 8.27, s, 3H  ⎫ C-2 methyl |
| 8.60, s, 3H  ⎭ |
| 8.78, d, 3H, J$_{9,10}$ = 6.5H$_z$, C-10 methyl |

EXAMPLE 19

Preparation of Cis-3-(1'-hydroxyethyl)-4-(2'-hydroxyethyl)-2-azetidinone

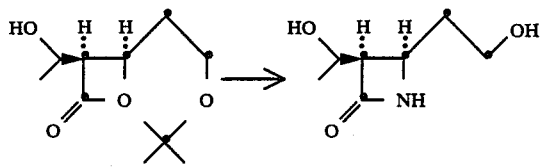

Following the procedure described for the preparation of trans-3-benzyl-4-(2'-hydroxyethyl)-2-azetidinone from 8-oxo-2,2-dimethyl-7α-benzyl-3-oxa-1-azabicyclo[4.2.0]octane and using 8-oxo-2,2-dimethyl-7β-(1'-hydroxyethyl)-3-oxa-1-azabicyclo[4.2.0]octane one obtains cis-3-(1'-hydroxyethyl)]-4-(2'-hydroxyethyl)-2-azetidinone.

EXAMPLE 20

Preparation of 8-Oxo-2-methoxy-3-oxa-1-azabicyclo[4.2.0]octane

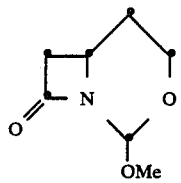

Following the procedure described for the preparation of 8-oxo-2,2-dimethyl-3-oxa-1-azabicyclo[4.2.0]octane from 4-(2'-hydroxyethyl)-2-azetidinone and using trimethyl orthoformate instead of 2,2-dimethoxypropane one obtains 8-oxo-2-methoxy-3-oxa-1-azabicyclo[4.2.0]octane.

i.r. (CHCl$_3$)μ: 5.69 (β-lactam).

nmr (CDCl$_3$)τ: 4.30, s, 1H, C-2 methine; 5.67–6.43, m, 3H, C-4 methylene+C-6 methine; 6.62, s, 3H, OCH$_3$; 6.75, dd, 1H, J$_{7,7}$=16 Hz, J$_{6,7}$=5 Hz; C-7 methylene proton cis to C-6H; 7.33, dd, 1H, J$_{77}$=16 H$_z$, J$_{6,7}$=2 H$_z$, C-7 methylene proton trans to C-6H; 7.70–8.65, m, 2H, C-5 methylene.

EXAMPLE 21

Preparation of 8-Oxo-2-methoxy-7α and β-benzoyl-3-oxa-1-azabicyclo[4.2.0]octane

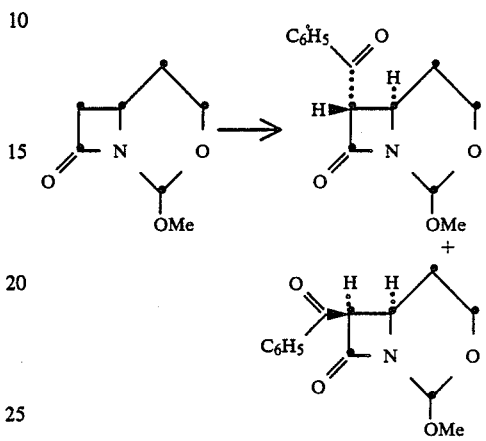

To a solution of 1.1 equivalent of freshly prepared lithium diisopropylamide in 4 ml anhydrous tetrahydrofuran under nitrogen atmosphere at −78° is added a solution of 8-oxo-2-methoxy-3-oxa-1-azabicyclo[4.2.0]octane (56 mg, 0.357 mmole) in 1 ml anhydrous tetrahydrofuran which has been cooled to −78° C. After two minutes the resulting lithium enolate is treated with methyl benzoate (49 mg, 0.357 mmole) and the solution allowed to warm to 0° over a 15 min period. The solution is then poured into water and the aqueous phase is saturated with sodium chloride and extracted with methylene chloride. The combined methylene chloride solutions are dried over magnesium sulphate, filtered and the filtrate evaporated under reduced pressure to give 94 mg of crude product. Purification by preparative thick-layer chromatography on silica gel developing with ether gives 8-oxo-2-methoxy-7α and β-benzoyl-3-oxa-1-azabicyclo[4.2.0]octane as a mixture.

ir (CHCl$_3$)μ: 5.67 (β-lactam); 5.96 (benzoyl).

nmr (CDCl$_3$)τ: 1.73–2.05, m, 2H, ArH; 2.33–2.63, m, 3H, ArH; 4.28, s, 1H, C-2 methine; 5.37 and 5.40, two overlapping d's; 1H, J$_{6,7α}$=4 H$_z$, J$_{6,7β}$=2 H$_z$, C-7α and β methine; 5.47–5.77, m, 1H, C-6 methine; 6.00–6.37, m, 2H, C-4 methylene; 6.67, s, 3H, OCH$_3$; 7.80–8.13, m, 2H, C-5 methylene.

EXAMPLE 22

Preparation of Cis and Trans-1-Formyl-3-benzoyl-4-(2'-hydroxyethyl)-2-azetidinone

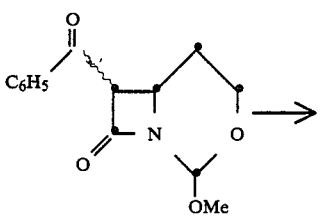

-continued

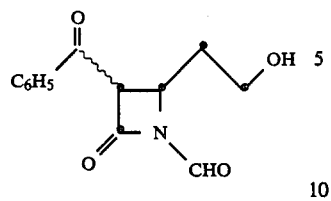

A solution of 8-oxo-2-methoxy-7α and β-benzoyl-3-oxa-1-azabicyclo[4.2.0]octane in aqueous p-dioxane containing 0.1 molar equivalent of concentrated sulfuric acid is stirred at room temperature for a period of 80 minutes. The solution is neutralized with 5% sodium bicarbonate solution and extracted with methylene chloride. The combined organic solutions are dried over magnesium sulfate, filtered and the filtrate is evaporated under reduced pressure to give cis and trans-1-formyl-3-benzoyl-4-(2'-hydroxyethyl)-2-azetidinone.

EXAMPLE 23

Preparation of Cis and Trans-3-Benzoyl-4-(2'-hydroxyethyl)-2-azetidinone

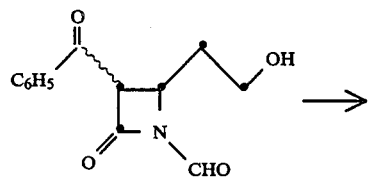

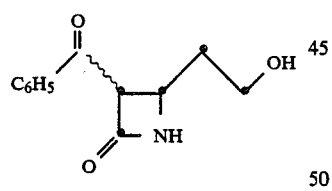

A solution of cis and trans-1-formyl-3-benzoyl-4-(2'-hydroxyethyl)-2-azetidinone in p-dioxane is treated at room temperature (25° C.) with an aqueous solution of 1 equivalent of sodium bicarbonate. The resulting solution is stirred for a period of two hours. It is then acidified by addition of 1M pH 3 phosphate buffer. The product is extracted with ethylacetate washing with brine. The ethyl acetate solution is then dried over magnesium sulfate and filtered. Evaporation of the filtrate under reduced pressure gives a mixture of cis and trans-3-benzoyl-4-(2'-hydroxyethyl)-2-azetidinone.

EXAMPLE 24

Preparation of 8-Oxo-2,2-dimethyl-7α and β-hydroxyisopropyl-3-oxa-1-azabicyclo[4.2.0]octane

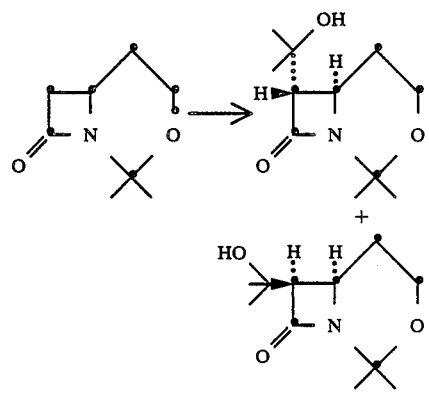

The lithium enolate of 8-oxo-2,2-dimethyl-3-oxa-1-azabicyclo[4.2.0]octane (40 mg., 0.258 mmole) is prepared as described in the preparation of 8-oxo-2,2-dimethyl-7α-isopropyl-3-oxa-1-azabicyclo[4.2.0]octane. The enolate at $-78°$ is treated with excess acetone. After 5 minutes at $-78°$ the reaction is quenched by pouring the reaction mixture into water. The aqueous phase is saturated with sodium chloride and extracted with methylene chloride. The combined methylene chloride solutions are dried over magnesium sulfate, filtered and the filtrate evaporated under reduced pressure to give 48 mg of crude product. Purification by preparative thick-layer chromatography on silica gel developing with 10% methanol/chloroform gives 8-oxo-2,2-dimethyl-7α and β-hydroxyisopropyl-3-oxa-1-azabicyclo[4.2.0]octane (23 mg and 3 mg, respectively).

7α-diasteromer:

| |
|---|
| ir (CHCl₃)μ 5.75 (β-lactam) |
| nmr (CDCl₃)τ 6.0–6.23, m, 2H, C-4 methylene |
| 6.27–6.60, m, 1H, C-6 methine |
| 7.13, d, 1H, $J_{6,7}$ = 1.9Hz, C-7 methine |
| 7.97–8.60, m, 2H, C-5 methylene |
| 8.03, s, 1H, OH |
| 8.22, s, 3H ⎫ C-2 methyls |
| 8.53, s, 3H ⎭ |
| 8.60, s, 3H ⎫ (CH₃)₂CHOH |
| 8.68, s, 3H ⎭ |

7β-diastereomer:

| |
|---|
| ir(CHCl₃)μ 5.74 (β-lactam) |
| nmr(CDCl₃)τ 6.06–6.44, m, C-4 methylene + C-6 methine |
| 6.79, d, $J_{6,7}$ = 5Hz, C-7 methine |
| 8.0–8.6, m, C-5 methylene |
| 8.24, s ⎫ C-2 methyls |
| 8.52, s ⎭ |
| 8.60, s ⎫ (CH₃)₂CHOH |
| 8.71, s ⎭ |

EXAMPLE 25

Preparation of
Trans-3-hydroxyisopropyl-4-(2'-hydroxyethyl)-2-azetidinone

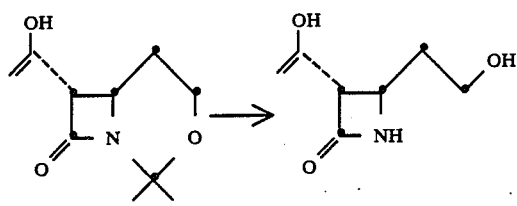

Following the procedure described for the preparation of trans-3-benzyl-4-(2'-hydroxyethyl)-2-azetidinone from 8-oxo-2,2-dimethyl-7α-benzyl-3-oxa-1-azabicyclo[4.2.0]octane and using 8-oxo-2,2-dimethyl-7α-hydroxyisopropyl-3-oxa-1-azabicyclo[4.2.0]octane one obtains trans-3-hydroxyisopropyl-4-(2'-hydroxyethyl)-2-azetidinone

EXAMPLE 25a

Preparation of
Cis-3-hydroxyisopropyl-4-(2'-hydroxyethyl)-2-azetidinone

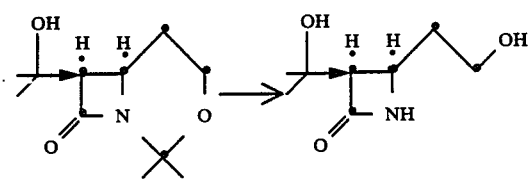

Following the procedure described for the preparation of trans-3-benzyl-4-(2-hydroxyethyl)-2-azetidinone from 8oxo-2,2-dimethyl-7α-benzyl-3-oxa-1-azabicyclo[4.2.0]octane and using 8-oxo-2,2-dimethyl-7β-hydroxyisopropyl-3-oxa-1-azabicyclo[4.2.0]octane one obtains cis-3-hydroxyisopropyl 4-(2'-hydroxyethyl)-2-azetidinone.

EXAMPLE 26

Preparation of
8-Oxo-7-acetoxymethylene-2,2-dimethyl-3-oxa-1-azabicyclo[4.2.0]octane

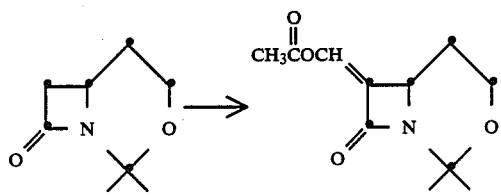

To a solution of 2.0 equivalents of freshly prepared lithium diisopropylamide in 5 ml anhydrous tetrahydrofuran under nitrogen atmosphere at −78° C. is added a solution of 8-oxo-2,2-dimethyl-3-oxa-1-azabicyclo[4.2.0]octane (98 mg., 0.629 mmmole) in 2 ml anhydrous tetrahydrofuran which has been cooled to −78° C. After two minutes excess anhydrous N,N-dimethylformamide (460 mg, 6.29 mmole) is added followed immediately by distilled and degassed acetyl chloride (148 mg, 1.89 mmole) which has been cooled to −78° C. After stirring at −78° for a period of 5 minutes, the reaction mixture is poured into 0.2M pH 7 phosphate buffer. The product is extracted with methylene chloride. The combined methylene chloride solutions are dried over magnesium sulfate, filtered and the filtrate evaporated under reduced pressure to give 64 mg of a colorless oil. Purification by preparative thick-layer chromatography on silica gel developing twice with ether gives 8-oxo-7-acetoxy-methylene-2,2-dimethyl-3-oxa-1-azabicyclo[4.2.0]octane (25 mg).

ir (CHCl₃)μ: 5.65 (β-lactam), 5.75 (ester), 5.89 (C═C).

nmr (CDCl₃)τ:

| |
|---|
| 2.42, d, 1H, $J_{6,9}$ = 1Hz, C-9 vinyl |
| 5.87, dd further split by C-9 vinyl proton, 1H, $J_{5,6}$ = 10H z and 6Hz, $J_{6,9}$ = 1Hz, C-6 methine |
| 6.07–6.30, m, 2H, C-4 methylene |
| 7.82, s, 3H, OCOCH₃ |
| 8.20, s, 3H  ⎱ C-2 methyls |
| 8.53, s, 3H  ⎰ |
| 7.77–8.67, m, 2H, C-5 methylene |

EXAMPLE 27

Preparation of
8-Oxo-7-(1'-acetoxyethylidene)-2,2-dimethyl-3-oxa-1-azabicyclo[4.2.0]octane

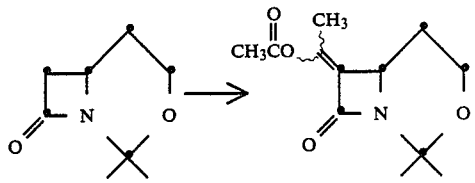

Following the procedure described for the preparation of 8-oxo-7-acetoxymethylene-2,2-dimethyl-3-oxa-1-azabicyclo[4.2.0]octane from 8-oxo-2,2-dimethyl-3-oxa-1-azabicyclo[4.2.0]octane and using N,N-dimethylacetamide instead of N,N-dimethylformamide one obtains 8-oxo-7-(1'-acetoxyethylidene)-2,2-dimethyl-3-oxa-1-azabicyclo[4.2.0]octane.

ir (CHCl₃) μ: 5.67 (β-lactam), 5.72 (ester), 5.90 (C═C).

nmr (CDCl₃) τ:

| |
|---|
| 5.53–6.00, m, 1H C-6 methine |
| 6.02, m, 2H, C-4 methylene |
| 7.53–8.73, m, 2H, C-5 methylene |

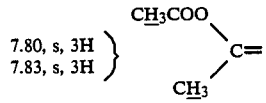

| |
|---|
| 8.22, s, 3H  ⎱ C-2 methyls |
| 8.57, s, 3H  ⎰ |

EXAMPLE 28

Preparation of
8-Oxo-2,2,7β-trimethyl-3-oxa-1-azabicyclo[4.2.0]octane

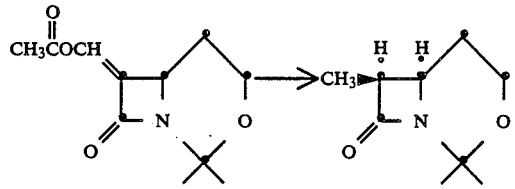

A solution of 8-oxo-7-acetoxymethylene-2,2-dimethyl-3-oxa-1-azabicyclo[4.2.0]octane (38 mg, 0.169 mmole) in 5 ml of ethyl acetate containing 4 mg of platinum oxide is hydrogenated at room temperature and 40 psi hydrogen for a period of 35 minutes. The reaction mixture is filtered through a bed of supercel washing with additional ethyl acetate. Evaporation of the filtrate under reduced pressure gives 31 mg of crude product. Purification by preparative thick-layer chromatography developing with 2:1 ethyl acetate/benzene gives 8-oxo-2,2,7β-trimethyl-3-oxa-1-azabicyclo[4.2.0]octane (13 mg).

ir (CHCl$_3$)μ: 5.74 (β-lactam).
nmr (CDCl$_3$)τ:

| |
|---|
| 6.04–6.20, m, C-4 methylene |
| 6.28, sextet partially covered by above m, J = 10H$_z$ and 5.2 H$_z$; C-6 methine |
| 6.71, m, J = 7.6H$_z$ and 5.2H$_z$, C-7 methine |
| 7.92–8.84, m, C-5 methylene |
| 8.26, s ⎱ C-2 methyls |
| 8.60, s ⎰ |
| 8.80, d, J = 7.5H$_z$ |

EXAMPLE 29

Preparation of
cis-3-methyl-4-(2'-hydroxyethyl)-2-azetidinone

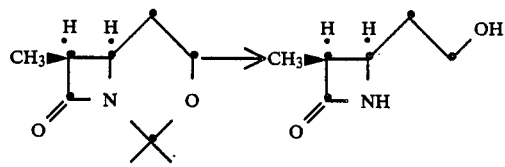

Following the procedure described for the preparation of trans-3-benzyl-4-(2-hydroxyethyl)-2-azetidinone from 8-oxo-2,2-dimethyl-7α-benzyl-3-oxa-1-azabicyclo[4.2.0]octane and using 8-oxo-2,2-dimethyl-7β-methyl-3-oxa-1-azabicyclo[4.2.0]octane one obtains cis-3-methyl-4-(2'-hydroxyethyl)-2-azetidinone.

EXAMPLE 30

Preparation of
8-Oxo-2,2-dimethyl-7β-ethyl-3-oxa-1-azabicyclo[4.2.0]octane

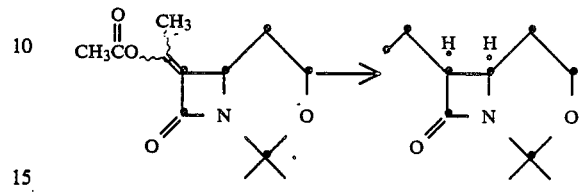

A solution of 8-oxo-7-(1'-acetoxyethylidene)-2,2-dimethyl-3-oxa-1-azabicyclo[4.2.0]octane (11 mg, 0.046 mmole) in 2 ml ethyl acetate and 0.2 ml methanol containing 10 mg of platinum oxide is hydrogenated at room temperature and 40 psi hydrogen for a period of 60 minutes. The reaction mixture is filtered through a bed of supercel washing with additional ethyl acetate. Evaporation of the filtrate under reduced pressure gives 8 mg of crystalline product. Purification by preparative thick-layer chromatography developing twice with ether gives 8-oxo-2,2-dimethyl-7β-ethyl-3-oxa-1-azabicyclo[4.2.0]octane (6 mg).

ir (CHCl$_3$)μ: 5.74 (β-lactam).
nmr (CDCl$_3$)δ:

| |
|---|
| 6.06–6.22, m, C-4 methylene |
| 6.26, sextet partially under above m; J = 10.5H$_z$, 10.5H$_z$ and 5.5H$_z$; C-7 methine |
| 6.90, m; J = 8.5H$_z$, 7H$_z$, 5.5H$_z$; C-7 methine |
| 7.94–8.89, m, C-5 methylene + C-9 methylene |
| 8.26, s ⎱ C-2 methyls |
| 8.59, s ⎰ |
| 9.02, t, J = 7H$_z$, CH$_3$CH$_2$ |

EXAMPLE 31

Preparation of
Cis-3-Ethyl-4-(2'-hydroxymethyl)-2-azetidinone

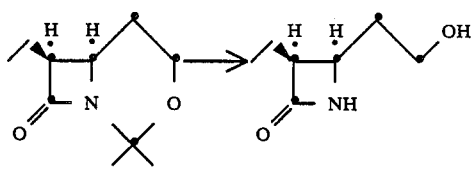

Following the procedure described for the preparation of trans-3-benzyl-4-(2-hydroxyethyl)-2-azetidinone from 8-oxo-2,2-dimethyl-7α-benzyl-3-oxa-1-azabicyclo[4.2.0]octane and using 8-oxo-2,2-dimethyl-7β-ethyl-3-oxa-1-azabicyclo[4.2.0]octane one obtains cis-3-ethyl-4-(2'-hydroxyethyl)-2-azetidinone.

EXAMPLE 32

Preparation of
1-(t-butyldimethylsilyl)-3-acetyl-4-(2'-hydroxyethyl)-2-azetidinone

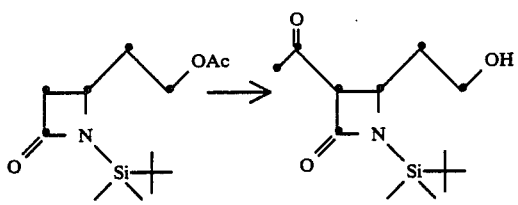

To a solution of 1.1 equivalents of freshly prepared lithium diisopropylamide in 3 ml anhydrous tetrahydrofuran under a nitrogen atmosphere at −78° is added a solution of 1-(t-butyldimethylsilyl)-4-(2'-acetoxyethyl)-2-azetidinone (61 mg, 0.225 mmole) in 1 ml anhydrous tetrahydrofuran which has been cooled to −78°. After 12 minutes the reaction mixture is poured into 5 ml water. The solution is saturated with sodium chloride and extracted with methylene chloride. The combined methylene chloride solutions are washed with brine, dried over magnesium sulfate and filtered. Evaporation of the filtrate under reduced pressure gives 50 mg of crude product. Purification by preparative thick-layer chromatography on silica gel developing with ethyl acetate gives 1-(t-butyldimethylsilyl)-3-acetyl-4-(2'-hydroxyethyl)-2-azetidinone (19 mg).

ir (CHCl$_3$)μ: 5.73 (β-lactam), 5.83 (ketone).
nmr (CDCl$_3$)τ:

---

5.88–6.57, m, 4H, C-3 methine + C-4 methine
+ CH$_2$CH$_2$OH
7.55–8.85, m, 3H, CH$_2$CH$_2$OH
7.68, s, 3H, CH$_3$CO
9.05, s, 9H, SiC(CH$_3$)$_3$
9.68, s  } 6H, Si(CH$_3$)$_2$
9.70, s

---

EXAMPLE 33

Preparation of
8-Oxo-2,2-dimethyl-7α-(1'-p-nitrobenzylcarbonyldioxyethyl)-3-oxa-1-azabicyclo[4.2.0]octane

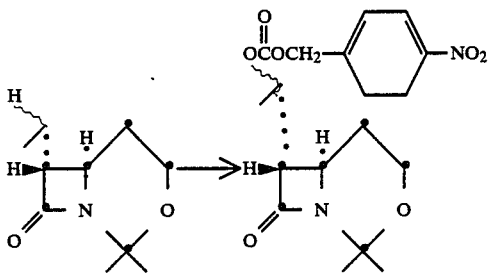

Under anhydrous conditions at 0°, a solution of 8-oxo-2,2-dimethyl-7α-(1'-hydroxyethyl)-3-oxa-1-azabicyclo[4.2.0]octane (60 mg, 0.302 mmole) in 0.6 ml ether is treated with powdered potassium hydroxide (19 mg, 0.332 mmole). After a period of 15 minutes, p-nitrobenzyl chloroformate (65 mg, 0.302 mmole) is added to the reaction mixture. Stirring is continued at room temperature for an additional 15 hours. The mixture is partitioned between 1M pH 7 phosphate buffer and more ether. The ether phase is washed with water and brine, dried over magnesium sulfate and filtered. Evaporation of the filtrate under reduced pressure gives 67 mg of a colorless oil. Purification by preparative thick-layer chromatography on silica gel developing with 1:9 ethyl acetate/benzene gives 8-oxo-2,2-dimethyl-7α-(1'-p-nitrobenzylcarbonyldioxyethyl)-3-oxa-1-azabicyclo[4.2.0]octane (40 mg) as a mixture of diastereomers.

ir (CH$_2$Cl$_2$) μ: 5.68 (β-lactam and carbonate), 6.19 and 6.54 (nitro).

nmr (CDCl$_3$) τ: 1.67, d, 2H, ArH; 2.37, d, 2H, ArH; 4.67, s, 2H, ArCH$_2$; 4.67–5.22, m, CH$_3$CH; 5.98–6.25, m, 2H, C-4 methylene; 6.25–6.62, m, 1H, C-6 methine; 6.75–7.12, m, 1H, C-7 methine; 7.75–8.83, m, 2H, C-5 methylene; 8.22, s, 3H, C-2 methyl; 8.50–8.58, m, 5H, C-2 methyl+CH$_3$CH.

EXAMPLE 34

Preparation of
Trans-3-(1'-p-nitrobenzylcarbonyldioxyethyl)-4-(2'-hydroxyethyl)-2-azetidinone

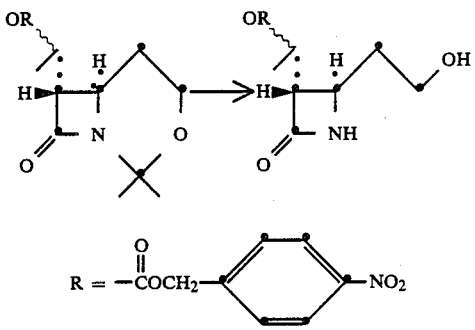

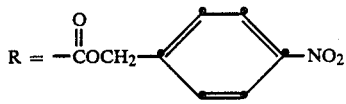

Following the procedure described for the preparation of trans-3-benzyl-4-(2'-hydroxyethyl)-2-azetidinone from 8-oxo-2,2-dimethyl-7α-benzyl-3-oxa-1-azabicyclo[4.2.0]octane and using 8-oxo-2,2-dimethyl-7α-(1'-p-nitrobenzylcarbonyldioxyethyl)-3-oxa-10azabicyclo[4.2.0]octane one obtains trans-3-(1'-p-nitrobenzylcarbonyldioxyethyl)-4-(2'-hydroxyethyl)-2-azetidinone.

ir (CH$_2$Cl$_2$)μ: 5.67 (β-lactam), 5.72 shoulder, 6.20 and 6.57 (nitro).

nmr (CDCl$_3$) δ: 1.73, d, 2H, J=8.5 Hz, ArH; 2.43, d, 2H, J=8.5 Hz, ArH; 3.63, broad s, 1H, NH; 4.37–5.13, m, 1H, CH$_3$CH; 4.72, s, 2H, ArCH$_2$; 6.07–6.53, m, 1H, C-4 methine; 6.23, t, 2H, J=5.5 Hz, CH$_2$OH; 6.73–6.93, m, 1H, C-3 methine; 7.63–8.97, m, 3H, CH$_2$CH$_2$OH; 8.53, d, J=6.5 Hz, CH$_3$CH.

EXAMPLE 35

Preparation of
8-Oxo-2,2-dimethyl-7β-(1'-p-nitrobenzylcarbonyldioxyethyl)-3-oxa-1-azabicyclo[4.2.0]octane

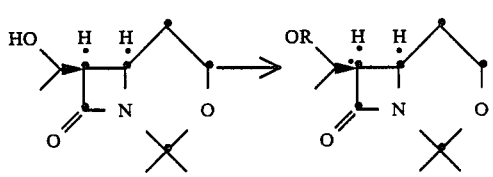

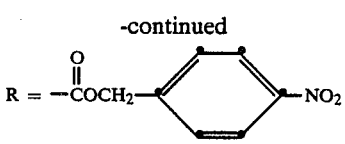

Following the procedure described for the preparation of 8-oxo-2,2-dimethyl-7α-(1'-nitrobenzylcarbonyldioxyethyl)-3-oxa-1-azabicyclo[4.2.0]octane from 8-oxo-2,2-dimethyl-7α-(1'-hydroxyethyl)-3-oxa-1-azabicyclo[4.2.0]octane and using 8-oxo-2,2-dimethyl-7β-(1'-hydroxyethyl)-3-oxa-1-azabicyclo[4.2.0]octane one obtains 8-oxo-2,2-dimethyl-7β-(1'-p-nittobenzylcarbonyldioxyethyl)-3-oxa-1-azabicyclo[4.2.0]octane.

EXAMPLE 36

Preparation of Cis-3-(1'-p-nitrobenzylcarbonyldioxyethyl)-4-(2'-hydroxyethyl)-2-azetidinone

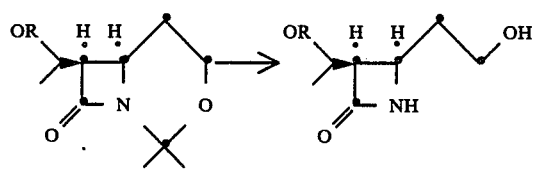

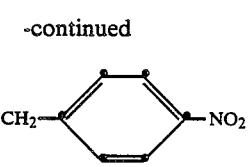

Following the procedure described for the preparation of trans-3-benzyl-4-(2'-hydroxyethyl)-2-azetidinone from 8-oxo-2,2-dimethyl-7α-benzyl-3-oxa-1-azabicyclo[4.2.0]octane and using 8-oxo-2,2-dimethyl-7β-(1'-p-nitrobenzylcarbonyldioxyethyl)-3-oxa-1-azabicyclo[4.2.0]octane one obtains cis-3-(1'-p-nitrobenzylcarbonyldioxyethyl)-4-(2'-hydroxyethyl)-2-azetidinone.

EXAMPLE 37

Following the procedures of the foregoing Examples, test and the footnotes to Table II (below), the following substituted azetidinones, useful in the preparation of the compounds of the present invention, are obtained.

TABLE II

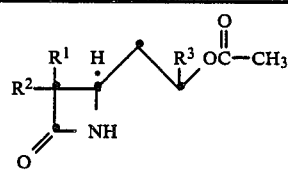

| Compound | $R^1$ | $R^2$ | $R^3$ |
|---|---|---|---|
| (1.) | (isopropyl) | H | H |
| (2.) | $C_6H_5-CH_2$ | H | H |
| (3.) | $\underset{CH_3}{\overset{H}{\diagdown}}C\diagup OCH_2-S-CH_3$ | H | H |
| (4.) | $\underset{CH_3}{\overset{H}{\diagdown}}C\diagup O-CH_2-SCH_3$ | H | $CH_2CH_2-CH_2N_3$ |
| (5.) | $\underset{CH_3}{\overset{H}{\diagdown}}C\diagup O-CH_2S-CH_3$ | H | $CH_2CH_2-CH_2-O-\underset{O}{\overset{\|}{C}}-OCH_2-\!\!\!\!\bigcirc\!\!\!\!-NO_2$ |
| (6.) | $\underset{CH_2}{\overset{OCH_2S-CH_3}{\diagup}}$ | H | $CH_3$ |
| (7.) | $\underset{CH_2}{\overset{OCH_2SCH_3}{\diagup}}$ | H | $CH_2-CH_2-COOCH_2C_6H_5$ |

TABLE II-continued

| | | | |
|---|---|---|---|
| (8.) | CH(OCH₂SCH₃)(CF₃) | H | H |
| (9.) | C₆H₅—CH₂—CH(O—CH₂SCH₃)— | H | H |
| (10.) | C₆H₅—CH₂CH(NH—C(O)—OCH₂—C₆H₄—NO₂)—CH(OCH₂SCH₃)— | H | H |
| (11.) | C₆H₅—C(O)— | H | H |
| (12.) | (CH₃)₂C(OH)— | H | H |
| (13.) | —CH₃ | H | H |
| (14.) | CH₃CH₂— | H | H |
| (15.) | H | CH₃CH(—)—O—C(O)—OCH₂—C₆H₄—NO₂ | H |
| (16.) | H | CH₃CH(—)—OCH₂SCH₃ | —CH₃ |
| (17.) | CH₃C(O)— | H | H |
| (18.) | CH₃CH(O—C(O)—OCH₂—C₆H₄—NO₂)— | H | H |
| (19.) | H | H | —CH₃ |
| (20.) | H | H | —CH₂CH₂—CH₂—N₃ |
| (21.) | (CH₃)₂CH—O—CH₂—SCH₃ | H | —CH₂—CH₂—COOCH₂—C₆H₅ |
| (22.) | CH₃—CH(H)(N₃)— | H | H |
| (23.) | —CH₃ | —CH₃ | H |
| (24.) | CH₃CH(—)—O—C(=S)—OCH₂—C₆H₄—NO₂ | CH₃ | H |
| (25.) | (CH₃)₂CH— | CH₃ | H |

TABLE II-continued

| | | | |
|---|---|---|---|
| (26.) | CH₃ group with OC(=O)CH₂-C₆H₄-NO₂ structure (isopropyl p-nitrobenzyl carbonate type) | H | phenyl-SCH₃ |
| (27.) | CH₃ group with O-C(=O)-CH₂-C₆H₄-NO₂ | H | CH=CH-S-CH₃ |
| (28.) | CH₃ group with O-C(=O)-CH₂-C₆H₄-NO₂ | H | phenyl-OCH₃ |
| (29.) | CH₃ group with O-C(=O)-CH₂-C₆H₄-NO₂ | H | CH=CH-CH₂CH₂-N₃ (i.e., —CH=CH—CH₂CH₂—N₃) |
| (30.) | CH₃ group with O-C(=O)-CH₂-C₆H₄-NO₂ | H | -CH₂CH₂CH₂CH₂-N₃ |

FOOTNOTE TO TABLE II
(1.) Described in Example 2.
(2.) Described in Example 3.
(3.) Described in Example 6.
(4.) From product of Step C, Example 6, using procedures of Examples 9, 10, 11, 12, 13 and 14, except using the Grignard reagent from 1-bromo-3-azido propane instead of CH₃MgBr in Example 12.
(5.) Same as (4.) except the Grignard reagent is made from 1-bromo-3-(p-nitrobenzyloxycarbonyloxy)-propane.
(6.) Following the procedures of Example 6, but using formaldehyde instead of acetaldehyde in Step A and using this product in the procedures of Examples 9, 10, 11, 12, 13 and 14.
(7.) Same as (6.) except that the Grignard reagent in Example 12 is prepared from 1-bromo-3-(benzyloxycarbonyl)-propane.
(8.) Following the procedure of Example 6 using trifluoro-acetaldehyde instead of acetaldehyde in Step A.
(9.) Same as (8.) except the aldehyde is 3-phenyl-propionaldehyde.
(10.) Same as (8.) except the aldehyde is 3-phenyl-3-(p-nitrobenzyloxycarbonylamino)-propionaldehyde.
(11.) By acetylation of product of Example 23.
(12.) By acetylation of product of Examples 25 or 25a.
(13.) By acetylation of product of Example 29.
(14.) By acetyaltion of product of Example 31.
(15.) By acetylation of product of Step G' of Example 8.
(16.) From product of Step C, Example 6 following the procedures of Examples 9, 10, 11, 12, 13 and 14.
(17.) Described in Example 32.
(18.) By acetylation of product of Step G, Example 8.
(19.) Described in Example 14.
(20.) By using the Grignard from 1-bromo-3-azido-propane in Example 12, followed by procedure of Examples 13 and 14.
(21.) Same as (5.) except the Grignard reagent is prepared from 1-bromo-3-(benzyloxycarbonyl)-propane.
(22.) From product of Example 8, Step E' by tosylation of alcohol;
followed by displacement with NaN₃ followed by procedure of Step G' and acetylation of the product.
(23.) From product of Example 8, Step D, using procedure of Example 3, Step A using CH₃ I instead of benzyl bromide and repeating the last procedure again, followed by procedures of Steps B and C of Example 3.
(24.) From product of Example 8, Step D, using procedure of Example 3, Step A but using CH₃ I instead of benzyl bromide, followed by procedure of Steps E, F and G of Example 8 and acylating the product.
(25.) From product of Example 28 followed by procedures of Steps A, B and C of Example 2.
(26.) From product of Step G', Example 8 using procedures of Examples 9, 10 and 11 followed by procedures of Example 15 but using p-methylthiophenyl-magnesium bromide instead of p-methoxyphenyl-magnesium bromide.
(27.) Same as (26.) except the Grignard reagent is 2-methyl-thio-vinyl-magnesium bromide.
(28.) From product of Step G', Example 8, using procedure of Examples 9, 10 and 11 followed by procedures of Example 15.
(29.) Same as (26.) except the Grignard reagent is prepared from 1-chloro-4-azido-1-butene.
(30.) Same as (26.) except the Grignard reagent is prepared from 1-chloro-4-azido-butane.

EXAMPLE 38

Following the procedures developed in the foregoing Examples and text, the following compounds, Table III, of the present invention (I) are obtained. Remarks relative to procedure are presented in the footnote to Table III.

TABLE III

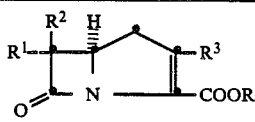

I

| Compound | R¹ | R² | R³ | R |
|---|---|---|---|---|
| (1.) | H | H | H | Na |

TABLE III-continued

| | | | | |
|---|---|---|---|---|
| (2.) | CH₃-CH(OH)- | H | H | Na |
| (3.) | H | CH₃-CH(OH)- | H | Na |
| (4.) | HO-CH₂- | H | H | Na |
| (5.) | H | HO-CH₂- | H | Na |
| (6.) | (CH₃)₂C(OH)- | H | H | Na |
| (7.) | H | (CH₃)₂C(OH)- | H | Na |
| (8.) | H | H | CH₃ | Na |
| (9.) | H | H | CH₂-CH₂-CH₂-NH₂ | H |
| (10.) | CH₃-CH(OH)- | H | CH₂CH₂-CH₂-NH₂ | H |
| (11.) | (CH₃)₂CH- | H | H | Na |
| (12.) | H | (CH₃)₂CH- | H | Na |
| (13.) | C₆H₅-C(=O)- | H | H | Na |
| (14.) | H | C₆H₅-C(=O)- | H | K |
| (15.) | C₆H₅CH₂- | H | H | K |
| (16.) | H | C₆H₅-CH₂- | H | Na |
| (17.) | CH₃CH₂ | H | H | Na |
| (18.) | H | CH₃CH₂ | H | K |
| (19.) | CH₃ | H | CH₃ | K |
| (20.) | H | CH₃ | CH₃ | Na |
| (21.) | CF₃-CH(OH)- | H | H | Na |

TABLE III-continued

| | | | | |
|---|---|---|---|---|
| (22.) | H | CF$_3$—CH(OH)— | H | Na |
| (23.) | C$_6$H$_5$CH$_2$—CH$_2$—CH(OH)— | H | H | K |
| (24.) | H | C$_6$H$_5$CH$_2$—CH$_2$—CH(OH)— | H | K |
| (25.) | C$_6$H$_5$CH(OH)CH$_2$CH(NH$_2$)— | H | H | H |
| (26.) | C$_6$H$_5$—CH(NH$_2$)—CH$_2$—CH(OH)— | H | H | H |
| (27.) | CH$_3$—C(=O)— | H | H | K |
| (28.) | H | CH$_3$—C(=O)— | H | K |
| (29.) | CH$_3$—CH(OH)— | H | —CH$_2$—CH(CH$_2$OH)— | Na |
| (30.) | H | CH$_3$—CH(OH)— | —CH$_2$—CH(CH$_2$OH)— | Na |
| (31.) | CH$_3$—CH(OH)— | H | —CH$_2$—CH(COONa)— | Na |
| (32.) | H | CH$_3$—CH(OH)— | —CH$_2$—CH(COONa)— | Na |
| (33.) | —CH$_2$—OH | H | —CH$_2$CH(COONa)— | Na |
| (34.) | CH$_3$—C(NH$_2$)— | H | H | H |
| (35.) | CH$_3$ | CH$_3$ | H | Na |
| (36.) | CH$_3$—CH(OH)— | CH$_3$ | H | Na |
| (37.) | CH$_3$—CH(OH)— | CH$_3$ | H | Na |
| (38.) | (CH$_3$)$_2$CH— | CH$_3$ | H | K |
| (39.) | CH$_3$—CH(OH)— | H | —C$_6$H$_4$—SCH$_3$ (para) | K |

TABLE III-continued

| (40.) | CH₃ OH H | H | 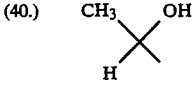 SCH₃ | Na |
| (41.) | CH₃ OH H | H | 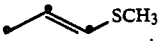 OCH₃ | Na |
| (42.) | CH₃ OH H | H | 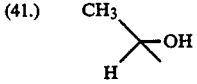 NH₂ | Na |
| (43.) | CH₃ OH | H | 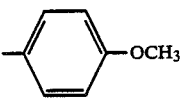 NH₂ | H |
| (44.) | CH₃ OH | H | 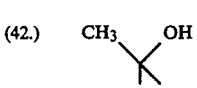 NH—C(=NH)H | H |
| (45.) | CH₃ OH | H |  NH—C(=NH)CH₃ | H |
| (46.) | CH₃ OH | H | 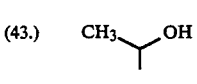 NH—C(=NH)H | H |
| (47.) | H | H |  NH—C(=NH)CH₃ | H |

(1.) Example 1.
(2.) Example 4.
(3.) From compound 15 of Example 37.
(4.) From compound 6 of Example 37, procedures of Example 4.
(5.) From epimer of compound 6 of Example 37, procedures of Example 4.
(6 & 7.) From compound 12 of Example 37, procedures of Example 4.
(8.) From compound 19 of Example 37, procedures of Example 1.
(9.) From compound 20 of Example 37, procedures of Example 1.
(10.) From compound 4 of Example 37, procedures of Example 4.
(11.) Example 7.
(12.) From epimer of compound 1 of Example 37, procedures of Example 7.
(13.) From compound 11 of Example 37, procedures of Example 1.
(14.) From epimer of compound 11 of Example 37, procedures of Example 1.
(15.) Example 5.
(16.) From epimer of compound 2 of Example 37, procedures of Example 5.
(17.) From compound 14 of Example 37, procedures of Example 1.
(18.) From epimer of compound 14 of Example 37, procedures of Example 1.
(19.) From compound 13 of Example 37, procedures of Example 1.
(20.) From epimer of compound 13 of Example 37, procedures of Example 1.
(21.) From compound 8 of Example 37, procedures of Example 4.
(22.) From epimer of compound 8 of Example 37, procedures of Example 4.
(23.) From compound 9 of Example 37, procedures of Example 4.
(24.) From epimer of compound 9 of Example 37, procedures of Example 4.
(25.) From compound 10 of Example 37, procedures of Example 4.
(26.) From epimer of compound 10 of Example 37, procedures of Example 4.
(27.) From compound 17 of Example 37, procedures of Example 1.
(28.) From epimer of compound 17 of Example 37, procedures of Example 1.
(29.) From compound 5 of Example 37, procedures of Example 4.
(30.) From epimer of compound 5 of Example 37, procedures of Example 4.
(31.) From compound 21 of Example 37, procedures of Example 4.
(32.) From epimer of compound 21 of Example 37, procedures of Example 4.
(33.) From compound 7 of Example 37, procedures of Example 4.
(34.) From compound 22 of Example 37, procedures of Example 1.
(35.) From compound 23 of Example 37, procedures of Example 1.
(36 & 37.) From compound 24 of Example 37, procedures of Example 1.
(38.) From compound 25 of Example 37, procedures of Example 1.
(39.) From compound 26 of Example 37, procedures of Example 1.
(40.) From compound 27 of Example 37, procedures of Example 1.
(41.) From compound 28 of Example 37, procedures of Example 1.
(42.) From compound 29 of Example 37, procedures of Example 1.
(43.) From compound 30 of Example 37, procedures of Example 1.

(44.) From compound 43 of Example 38, by treatment with ethyl formimidate hydrochloride at pH 8.5 (water, 25° C.)
(45.) From compound 43 of Example 38, by treatment with ethyl acetimidate hydrochloride at pH 8.5 (water, 25° C.).
(46.) From compound 10 of Example 38 by treatment with ethyl formimidate hydrochloride at pH 8.5 (water, 25° C.).
(47.) From compound 9 of Example 38 by treatment with ethyl acetimidate hydrochloride at pH 8.5 (water, 25° C.).

EXAMPLE 39

Sodium 1-carba-2-methyl-2-penem-3-carboxylate

Step A 1-(o-nitrobenzyloxycarbonylmethyltriphenyl-phosphoranyl)4-(carboxylmethyl)-2-azetidinone

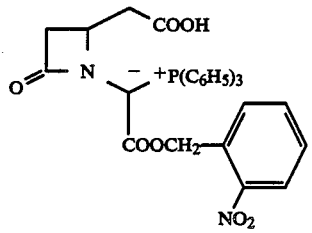

One gram of 1-(o-nitrobenzyloxycarbonylmethyltriphenylphosphoranyl)-4-(2-hydroxyethyl)-2-azetidinone is dissolved in 20 ml. acetone and cooled to 0° C. Jones Reagent (1 ml., 4N solution) is added dropwise over 5 min and the resulting solution is stirred at 0° C. for 10 min. Isopropanol (0.1 ml) is added. The mixture is stirred for another 2 min. The reaction mixture is diluted with CH$_2$Cl$_2$ and filtered. The filtrate is washed with saturated NaCl solution, dried and evaporated to give 0.851 g of crude acid which is used without further purification in the next step.

i.r. (cm$^{-1}$);

3500 to 2300 C—OH, 1735 broad ($\beta$-lactam, acid carbonyl), 1620 (ester carbonyl)

Step B 1-(o-nitrobenzyloxycarbonylmethyltriphenylphosphoranyl)-4-(chlorocarbonylmethyl)-2-azetidinone

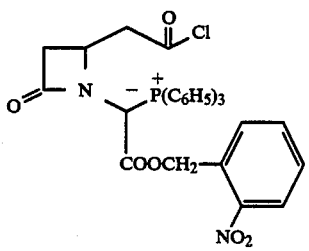

From Step A, 1-(o-nitrobenzyloxycarbonylmethyltriphenylphosphoranyl)-4-(carboxymethyl)-2-azetidinone (0.851 g) is dissolved in 20 ml CH$_2$Cl$_2$ and cooled to 0° C. under N$_2$. Oxalyl chloride (0.8 ml) is added dropwise over 5 min and then 1 drop of DMF is added. The mixture is stirred at 0° C. for 5 min and then at 25° C. for 15 min. The solvent and excess oxalyl chloride are evaporated under reduced pressure. The residue is the desired acid chloride which is used without purification in the next step.

Step C 1-(o-nitrobenzyloxycarbonyl triphenylphosphoranyl-methyl)4-(phenylthiocarbonylmethyl)-2-azetidinone

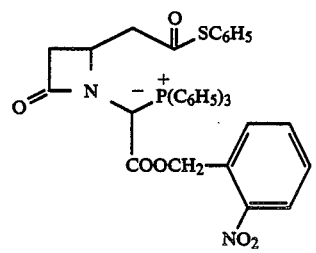

The product from Step B is dissolved in 20 ml CH$_2$Cl$_2$ and cooled to 0°, under N$_2$, Thiophenol (0.4 g) is added and then pyridine 0.8 ml is added dropwise. The reaction mixture is stirred at 0° for 5 min, then at 25° C. for 15 min, then diluted with CH$_2$Cl$_2$ and washed with water, dried and evaporated. The residue is chromatographed on silica gel using 50% EtOAc/C$_6$H$_5$ as eluant, to give 0.780 g of the thio ester.

i.r. (cm$^{-1}$); 1740 ($\beta$-lactam); 1700 (thioester); 1625(ester).

Step D 1-(o-nitrobenzyloxycarbonyl-triphenylphosphoranylmethyl)-4-(methylcarbonylmethyl)-2-azetidinone

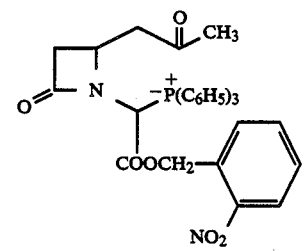

Cuprous iodide (0.380 g) is suspended in 10 ml anhydrous ether under N$_2$, in a dry flask and cooled to 0°. Methyl lithium (3.0 ml, 1.3 Molar) is added dropwise and the mixture is stirred at 0° for 5 min to give a yellow suspension. The mixture is then cooled to −50°. 1-(o-nitrobenzyloxycarbonyl-triphenylphosphoranylmethyl)-4-(phenylthiocarbonylmethyl)-2-azetidinone (0.674 g) in 10 ml THF is added dropwise over 5 min. The mixture is stirred at −50° for 5 min and allowed to come to −20° over 20 min and stirred at −20° for 5 min. Saturated NH$_4$Cl solution 5 ml is added and the mixture is diluted with CH$_2$Cl$_2$. Stirred at r.t. for 5 min. The organic phase is separated, dried and evaporated.

The residue is chromatographed on silica gel using EtOAc as eluant to give 0.162 g of the product 0.112 g of recovered thio ester.

i.r. (cm$^{-1}$); 1740 β-lactam; 1710 ketone; 1620 ester.
n.m.r. δ2.16

Step E o-Nitrobenzyl-1-carba-2-methyl-2-penem-3-carboxylate

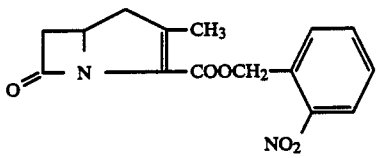

In xylene (3 ml), 1-(o-nitrobenzyloxycarbonyl-triphenylphosphoranylmethyl)-4-(methylcarbonylmethyl)-2-azetidinone (0.030 g) is dissolved, pyridine 0.019 ml is added and the mixture is heated under N$_2$ at 140° for 40 min. The xylene is removed under reduced pressure and the residue is purified by preparatory thin layer chromatography on silica gel using 50% EtOAc/C$_6$H$_5$ as eluant to give o-nitrobenzyl-1-carba-2-methyl-2-penem-3-carboxylate (0.003 g).

i.r. (cm$^{-1}$) 1775 (β-lactam); 1720 ester; 1630 c=c (100 Hz).

n.m.r. δ2.18 S(CH$_3$—); 2.86 CH$_2$—d=c, 219 g (trans C-6H, J$_{5-6}$=2.8 Hz, J$_{gem}$=16 Hz); 3.5q (cis C-6 H, J$_{5-6}$=5 Hz, J$_{gem}$=16 Hz); 4.2 m (C-5H); 5.72q (CH$_2$—C$_6$HzNO$_2$); 7.3–8.2 m (aromatic H).

u.v. λ$_{max}^{270}$ (CH$_2$Cl$_2$), ε=11450.

Step F

Sodium-1-carba-2-methyl-2-penem-3-carboxylate

The product of Step E, o-nitrobenzyl-1-carba-2-methyl-2-penem-3-carboxylate, (0.010 g) is dissolved in dioxane (2 ml) and water (2 ml) pH 7 phosphate buffer (0.1 ml, 0.5 Molar) is added and the mixture is deoxygenated by bubbling N$_2$ through the mixture. The mixture is photolysed for 1 hr using 350 nm light in a pyrex vessel cooled by a cold finger. The photolysis mixture is extracted with ethyl acetate. The aqueous phase is freeze dried to give sodium-1-carba-2-methyl-2-penem-3-carboxylate
u.v. λ$_{max}^{265}$(H$_2$O).

EXAMPLES 40–41

Sodium 1-carba-2-phenyl-2-penem-3-carboxylate

Step A 1-(o-nitrobenzyloxycarbonyltriphenylphosphoranylmethyl, 4-(phenylcarbonylmethyl)-2-azetidinone

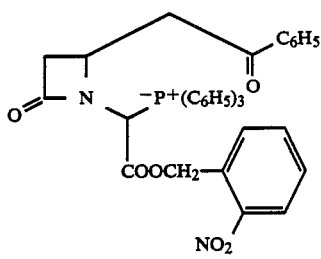

Following the procedure described in Example 39, Step D, but substituting an equivalent amount of phenyl lithium (or phenyl magnesium bromide) for methyl lithium, there is obtained 1-(o-nitrobenzyloxycarbonyl-triphenylphosphoranylmethyl)-4-(phenylcarbonylmethyl)-2-azetidinone.

Step B o-nitrobenzyl-1-carba-2-phenyl-2-penem-3-carboxylate

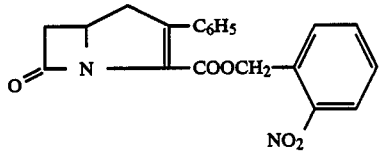

The product of Step A, 1-(o-nitrobenzyloxycarbonyl-triphenylphosphoranylmethyl)-4-(phenylcarbonylmethyl)-2-azetidinone (0.030 g), is dissolved in xylene (3 ml) and heated nder N$_2$, at 140° for 40 min. The xylene is removed under reduced pressure and the residue purified by preparatory tlc on silic gel to give o-nitrobenzyl-1-carba-2-phenyl-2-penem-3-carboxylate.

i.r. cm$^{-1}$ 1780 (β-lactam); 1722 (ester); 1610 (c=c).

n.m.r. (300 MHz) δ: 7.2–8.2 m(ArH); 5.6 q (Ar—CH$_2$—O— 4.4 m(C-5H); 3.59 q (J=7.5, U=3, C-6αH), 3.3 m (C-1H) 3.1 q(J=7.5, J=1.5, C-6βH)

u.v. λ$_{max}^{CH2Cl2}$ 268 and 297.

Step C

Sodium-1-carba-2-phenyl-2-penem-3-carboxylate

Photolysis of o-nitrobenzyl-1-carba-2-phenyl-2-penem-3-carboxylate by the procedure described in Example 39, Step F, gives sodium-1-carba-2-phenyl-2-penem-3-carboxylate.

u.v. λ$_{max}^{H2O}$ 295.

EXAMPLE 42

Sodium 1-carba-2-(p-methoxyphenyl)-2-penem-3-carboxylate

Step A

1-(o-nitrobenzyloxycarbonyl-triphenylphosphoranyl-methyl-4-(p-methoxyphenylcarboxymethyl)-2-azetidinone

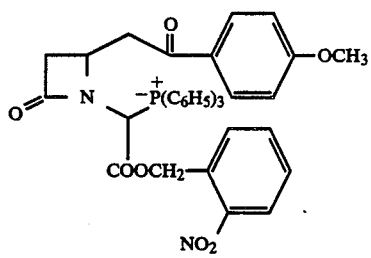

A solution of p-methoxybenzyl magnesium bromide (0.25M in 50% Et₂O/THF, 0.8 ml, is placed under N₂ and cooled to 0°. Cuprous iodide (0.019 g) is added and the mixture is stirred at 0° for ½ hours; 1-(o-nitrobenzyloxycarbonyltriphenylphosphoranylmethyl)-4-(phenylthiocarbonylmethyl)-2-azetidinone (0.034 g) in 0.5 ml THF is added dropwise. The mixture is allowed to stir at 0° for 40 min. A saturated solution of NH₄Cl in H₂O is added and the mixture is allowed to stir for 15 min. The organic phase is separated. The aqueous phase is extracted twice with CH₂Cl₂. The combined organic extracted is dried, evaporated to give a residue which is separated by preparative tlc to give 0.011 g of product and 0.004 g recovered starting material.

i.r. (CHCl₃) cm⁻¹: 1735 (β-lactam); 1665 (ketone); 1605 (ester).

n.m.r. δ: 6.8–8.2 m(ArH); 4.8–6.0 m(ArCH₂) 3.9 s(OCH₃).

Step B o-Nitrobenzyl-1-carba-2-(p-methoxyphenyl)-2-penem-3-carboxylate

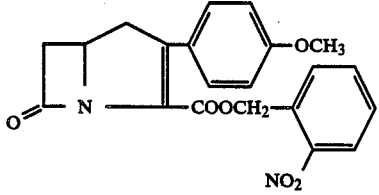

The product of Step C, 1-(o-nitrobenzyloxycarbonyl-triphenylphosphoranylmethyl)-4-(p-methoxyphenylcarbonylmethyl)-2-azetidinone (0.057 g), is dissolved in 5 ml xylene, placed under N₂ and heated at 140° for 3 hours. The xylene is removed under reduced pressure and the residue is purified by preparative tlc (50% EtOAc/C₆H₅ silica gel G) to give 0.005 g. of product.

i.r. cm⁻¹: 1770 (β-lactam); 1720 (ester); 1605 (c=c).

n.m.r. (300 Hz): δ:

| | |
|---|---|
| 7.4–8.2 m | ![structure with O₂N, H's] |
| 7.42 & 6.88 2d | ![structure with OCH₃, H's] |

5.7 q(ArCH₂); 4.34 m(C-5 H); 3.82 s(CH₃O); 3.5 q(J=8, J=3 C-6 αH); 3.28 d(J=5, C-1 H) 3.06 q(J=8, J=1.5 C-6 βH).

Step C

Sodium-1-carba-2-(p-methoxyphenyl)-2-penem-3-carboxylate

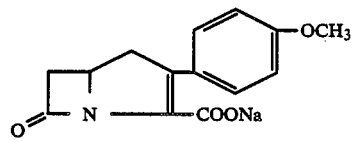

The product of Step B, o-nitrobenzyl-1-carba-2-(p-methoxyphenyl)-2-penem-3-carboxylate (10 mg), is dissolved in 5 ml dioxane, 1 ml EtOH and 5 ml H₂O; NaHCO₃ (2.2 mg, and 10 mg 10% Pd/C catalyst is added and the mixture is reduced under H₂ at 40 lbs for 45 minutes. The catalyst is filtered off and washed with 1 ml dioxane and 1 ml H₂O. The filtrate and washings are extracted with 3 × 10 ml EtOAc and then freeze dried to give sodium 1-carba-2-(p-methoxybenzyl)-2-penem-3-carboxylate.

u.v. λ$_{max}$ 295 nm (310 nm NH₂OH quenched, difference maximum).

EXAMPLE 43

Preparation of 1-Carba-2-penem-6α-(1-aminoethyl)-3-carboxylic Acid

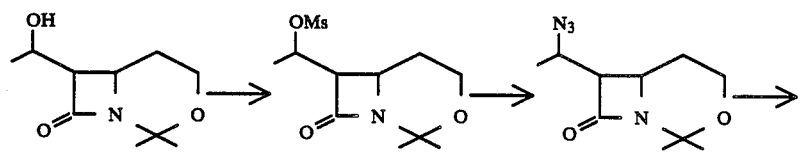

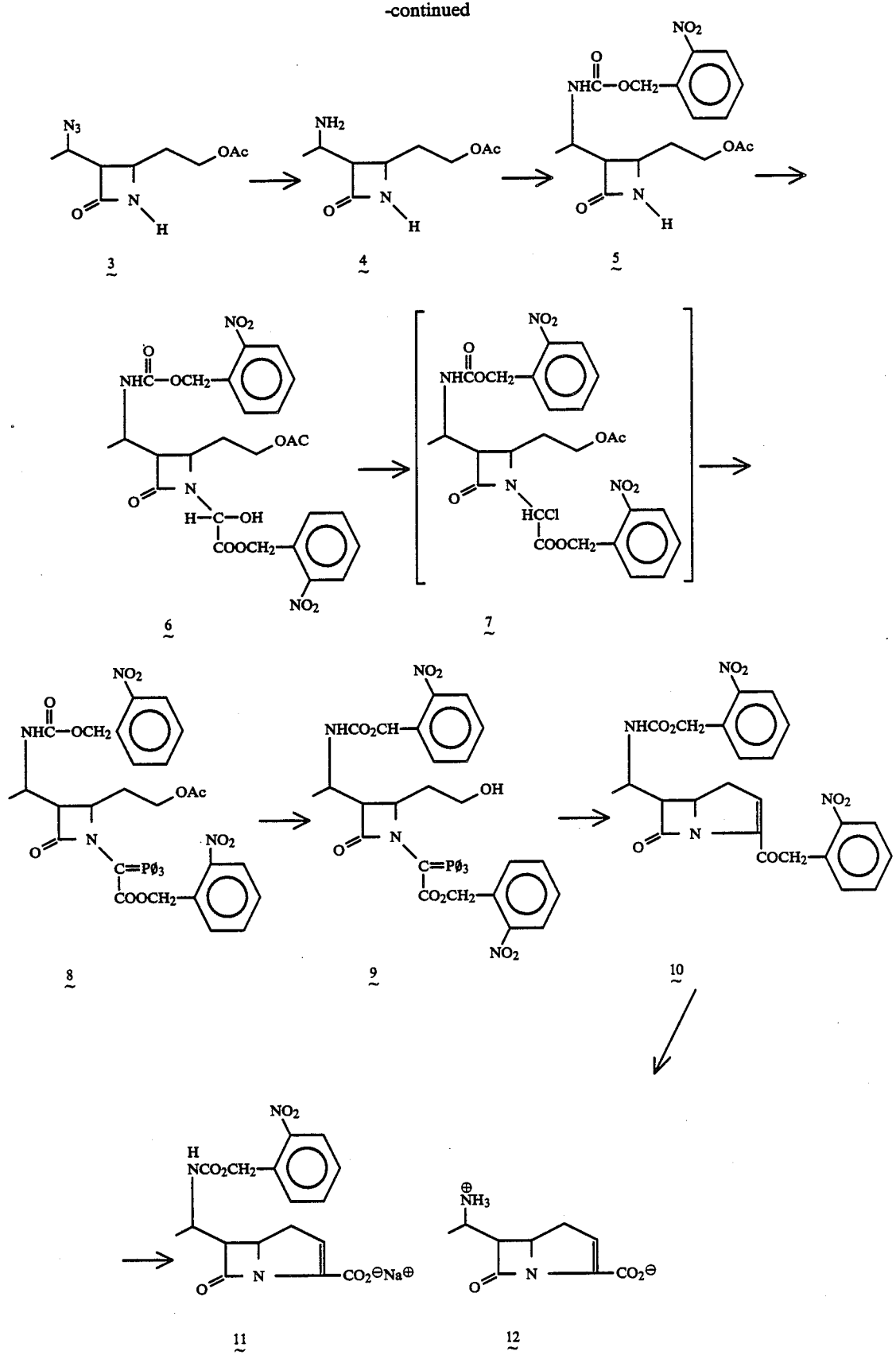
Step A

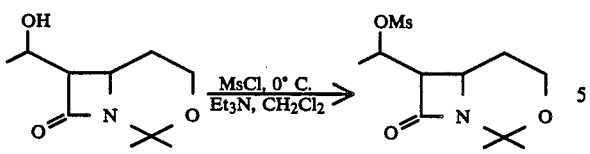

8-Oxo-2,2-dimethyl-7α and β-(1-hydroxyethyl)-3-oxa-1-azabicyclo[4.2.0]octane (1.2050 g, 0.00606 mole) is treated with 1.1 equimolar amount of methanesulfonyl chloride and triethylamine at 0° C. in $CH_2Cl_2$ with stirring. After 30 min, the reaction mixture is washed with cold water, pH 7 phosphate buffer, dried over $MgSO_4$ and evaporated in vacuo. The residue is column chromatographed

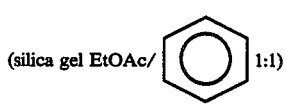

to give 1.4001 g, 0.00505 mole (77% yield) of the product.

nmr/$CDCl_3$:

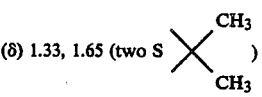

2.93, 2.96 (two S, $CH_3SO_2$)
3.0 (m, $C_7$—H)
3.3–4.00 (m, 3H, $CH_2$—O & $C_6$—H)
5.00 (m, 1H, $C_9$—H)

ir/neat (μm) 5.71 (β-lactam); 7.36 & 8.44 ($SO_2$).

Step B

Preparation of 8-Oxo-2,2-dimethyl-7α and β(1-azidoethyl)-3-oxa-1-azabicyclo[4.2.0]octane

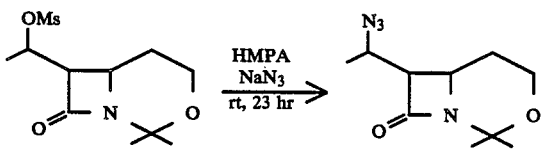

8-Oxo-2,2-dimethyl-7α and β-(1-methanesulfonyloxyethyl)-3-oxa-1-azabicyclo[4.2.0]octane (2.81 g, 0.0101 mole) is suspended in 10 ml HMPA and treated with $NaN_3$ (0.78 g, 0.012 mole) at room temperature with stirring for 23 hours. The HMPA is removed in vacuo at 70°. The residue is dissolved in $CH_2Cl_2$, washed with $H_2O$, dried over $MgSO_4$ and evaporated in vacuo. Column chromatography

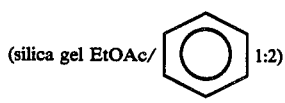

of the residue gives 1.56 g, 0.0070 mole (70% of the product).

nmr/$CDCl_3$:

(δ) 1.36 (d, $CH_3$)

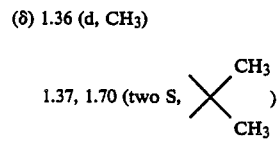

2.67–3.03 (m, $C_7$—H)
3.33–4.00 (m, $CH_2$—O & $C_6$—H)

ir/neat (mm) 4.74 (-$N_3$); 5.75 (β-lactam).

Step C

Preparation of trans-3-(1-azidoethyl)-4-(2'-acetoxyethyl)-2-azetidinone

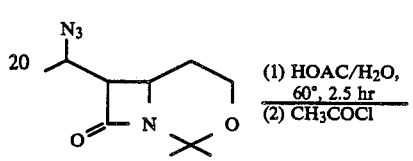

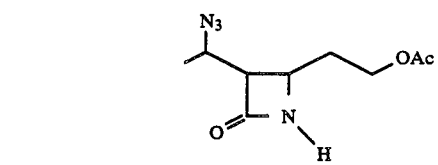

8-Oxo-2,2-dimethyl-7α and β-(1-azidoethyl)-3-oxa-1-azabicyclo[4.2.0]octane (1.31 g, 0.00586 mole) is dissolved in 80 ml HOAc/$H_2O$ (4:1) and heated at 65° for 2.5 hrs. The HOAc and $H_2O$ is removed in vacuo. Benzene is added to the residue and reevaporated to remove traces of water. The residue is then dissolved in 5.0 ml $CH_2Cl_2$, cooled to 0° C., and treated with 1.1 mole each of pyridine and acetyl chloride. The ice bath is removed 20 min after the mixing and stirring continues for another 20 min. After evaporated in vacuo, the residue is column chromatographed

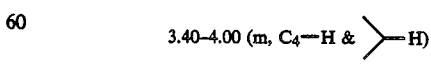

to give 0.800 g, 0.00354 mole (60% yield) of the product.

nmr/$CDCl_3$ (δ):

1.37, 1.48 (two d pairs, $CH_3$—)
2.03 (s, $CH_3CO$)
1.60–2.33 (m, $CH_2O$)
2.50–3.17 (m, $C_3$—H)

3.40–4.00 (m, $C_4$—H & >—H)

4.13 (t, $CH_2$—O—)
6.67 (broad, NH)

ir/neat (μm) 3.05 (NH); 4.74 ($N_3$); 5.62–5.81 (C=O); 8.19 (OAc).

Step D

Preparation of trans-3-(1-aminoethyl)-4-(2'-acetoxyethyl)-2-azetidinone

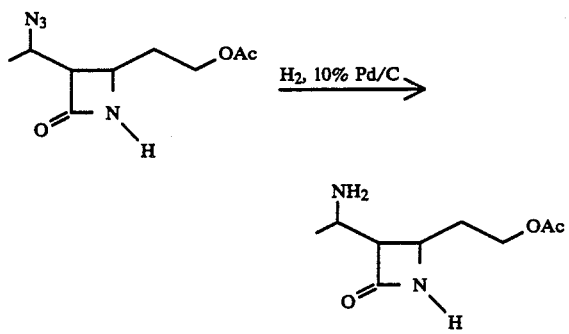

Trans-3-(1-azidoethyl)-4-(2'-acetoxyethyl)-2-azetidinone (0.824 g, 0.00364 mole), is dissolved in EtOAc and hydrogenated with 0.824 g, 10% Pd/C under 40 lbs of $H_2$ for 1 hr. IR shows disappearance of $N_3$ absorption. The catalyst is filtered off and the solution is evaporated in vacuo to give 0.658 g, (0.00328 mole, 90% yield) of the product.

nmr/CDCl$_3$ (δ):

1.15 & 1.20 (two d, CH$_3$)
2.05 (S, CH$_3$CO)
2.33–3.0 (m, C$_3$—H & NH$_2$)

3.02–3.80 (m, C$_4$—H & >—H)

4.15 (t, CH$_2$O)
7.15 (broad, N—H)

ir/neat (μm); 3.05 (NH) 5.62–5.81 (C=O).

Step E

Preparation of trans-3-(1-o-nitrobenzyloxycarbonylaminoethyl)-4-(2'-acetoxyethyl)-2-azetidinone

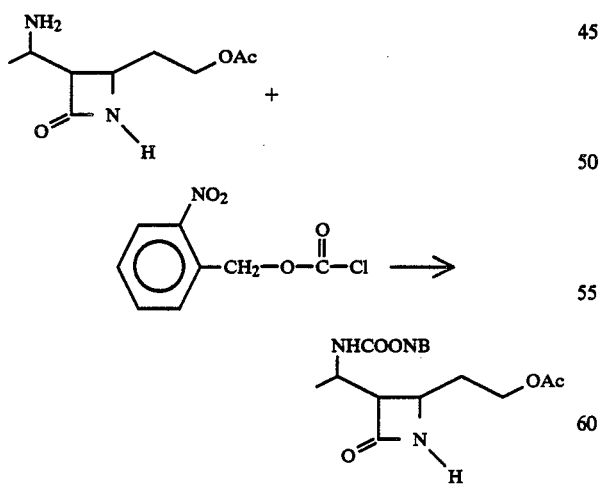

Trans and cis-3-(1-aminoethyl)-4-(2'-acetoxyethyl)-2-azetidinone (0.6575 g, 0.00328 mole) is dissolved in 10 ml CH$_2$Cl$_2$, cooled to 0° C., and treated with 1.1 mole each of pyridine and o-nitrobenzyl chloroformate. The reaction mixture is stirred at 0° for 20 min, the ice bath is removed and stirring continued for another 30 min. The solution is diluted with CH$_2$Cl$_2$, washed with H$_2$O, dried and evaporated in vacuo. Column chromatography

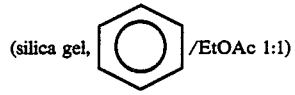

(silica gel, /EtOAc 1:1)

of the residue gives 0.7790 g (0.00206 mole, 63% yield) of the product.

nmr/CDCl$_3$ (δ):

1.32 (d, CH$_3$)
2.03 (s, CH$_3$CO)
2.81–3.15 (m, C$_3$H)

3.33–3.75 (m >—H)

4.13 (t, CH$_2$O)
5.48 (s, ArCH$_2$)
5.60 (broad, NHCOO)
6.81 (broad, NH)
7.25–8.25 (m, ArH)

ir/neat (μm): 3.03 (NH); 5.65–5.88 (C=O); 6.53 & 7.43 (NO$_2$).

Step F

Preparation of trans 1-(o-nitrobenzyloxycarbonylhydroxymethyl)-3-(1-o-nitrobenzyloxycarbonylaminoethyl)-4-(2'-acetoxyethyl)-2-azetidinone

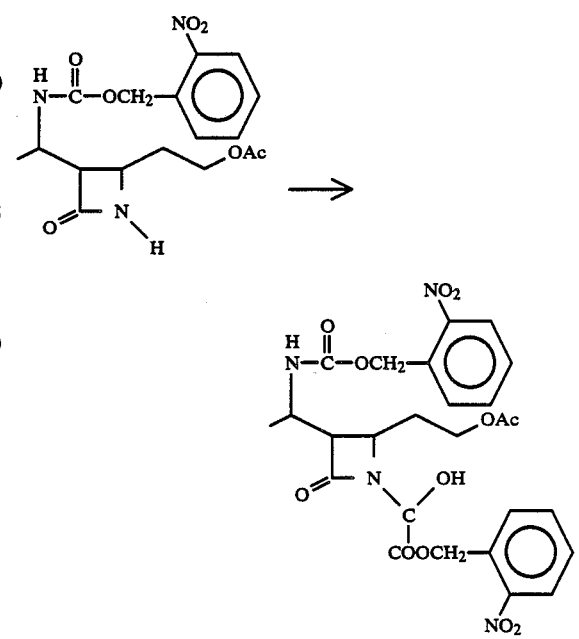

Ortho-nitrobenzyl glyoxalate preferred from (0.650 g, 0.00153 mole) of di-o-nitrobenzyl tartarate, is dissolved in 20 ml benzene and refluxed using a Dean-Stark water separator containing CaH$_2$ for an hour. Trans-3-(1-o-nitrobenzyloxycarbonylaminoethyl)-4-(2-acetoxyethyl)-2-azetidinone (0.580 g, 0.00153 mole) is added and the mixture is refluxed for 8 hrs, cooled, evaporated. The residue is column chromatographed

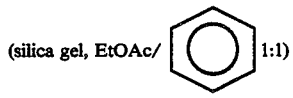

to give 0.775 g (0.00132 mole, 87% yield) of the product.

nmr/CDCl₃ (δ):

1.31 (d, CH₃)
2.03 (s, CH₃CO)
3.11 (m, C₃—H)
3.30–4.20 (m, C₄—H), CH₂OAc,

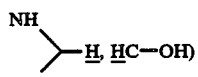

4.35 (broad, OH)
5.25–5.80 (m, ArCH₂, NHCO)
7.40–8.20 (m, ArH)

ir/neat (μm) 2.98 (broad, OH, NH) 5.65–5.88 (c=o) 6.53, 7.43 (NO₂).

Step G

Preparation of trans-1-(o-nitrobenzyloxycarbonylchloromethyl)-3-(1-o-nitrobenzyloxycarbonylaminoethyl)-4-(2'-acetoxyethyl)-2-azetidinone

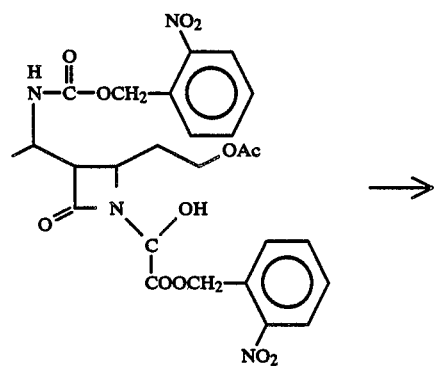

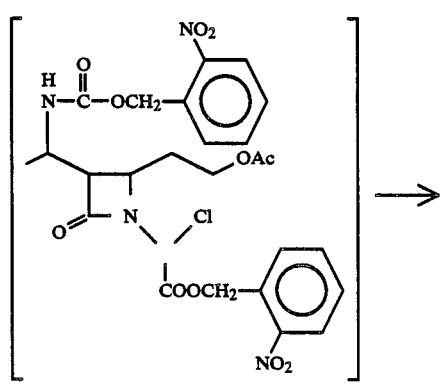

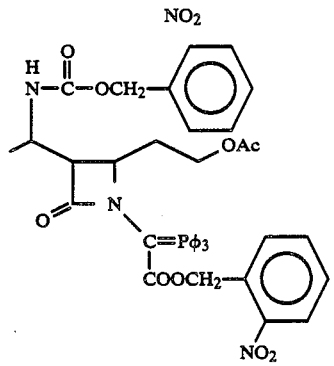

Trans-1-(o-nitrobenzyloxycarbonylhydroxymethyl)-3-(1-o-nitrobenzyloxycarbonylaminoethyl)-4-(2-acetoxyethyl)-2-azetidinone (0.775 g, 0.00132 mole) is treated with 1.2 equimolar amount each of pyridine and SOCl₂ in THF at −20°. After 20 min, the cooling bath is removed and stirring continued for another 20 mins. The reaction mixture is diluted with benzene, filtered, and evaporated to give the chloro product which is used immediately in the next reaction.

Step H

Preparation of trans-1-(o-nitrobenzyloxycarbonyltriphenylphosphoranylmethyl)-3-(1-o-nitrobenzyloxycarbonylaminoethyl)-4-(2'-acetoxyethyl)-2-azetidinone Trans-1-(o-nitrobenzyloxycarbonylchloromethyl)-3-(1-o-nitrobenzyloxycarbonylaminoethyl)-4-(2-acetoxyethyl)-2-azetidinone from above is dissolved in 4.0 ml DMF and treated with triphenylphosphine (0.414 g, 0.00158 mole) in 3.0 ml DMF at 25° C. for 1.0 hr; DMF is removed under vacuum and the residue is taken up in CHCl₃, washed with pH 7 phosphate buffer, dried and evaporated. Column chromatography of the residue

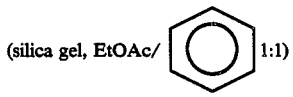

gives 0.700 g (0.000842 mole, 64% yield) of the product.

nmr/CDCl₃ (δ):

1.31 (d, CH₃)
2.03 (S, CH₃CO)
3.11 (m, C₃—H)

3.30–4.20 (m, C₄—H, CH₂OAc, 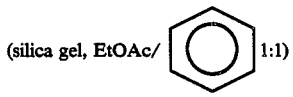—H)

5.25–5.80 (m, ArCH₂, NHCO)
7.28–8.18 (m, ArH)

ir/neat (μm) 2.98 (NH), 5.65–5.88 (⊕-lactam, acetate, carbonate), 6.17 (ester carbonyl).

Step I

Preparation of trans-1-(o-nitrobenzyloxycarbonyltriphenylphosphoranylmethyl)-3-(1-o-nitrobenzyloxycarbonylaminoethyl)-4-(2'-hydroxyethyl)-2-azetidinone

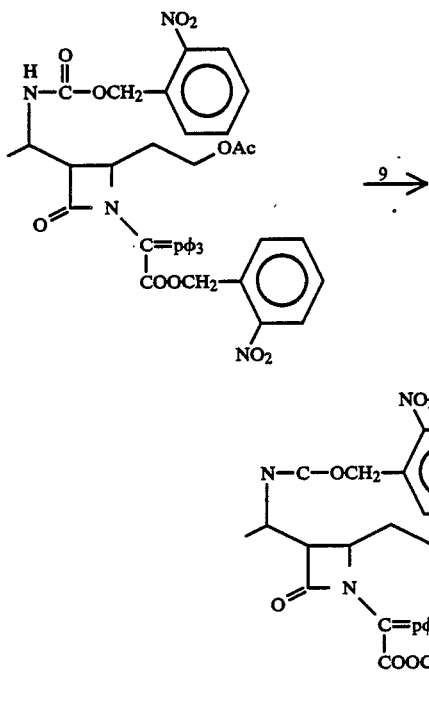

Trans-1-(o-nitrobenzyloxycarbonyltriphenylphosphoranylmethyl)-3-(1-o-nitrobenzyloxycarbonylaminoethyl)-4-(2-acetoxyethyl)-2-azetidinone (0.700 g, 0.000842 mole) is dissolved in 10 ml abs. methanol and treated with sodium methoxide (0.0500 g, 0.000926 mole) at room temperature (25° C.) in $N_2$. The solution is stirred at r.t. for 1½ hr. After removal of MeOH in vacuo, the residue is taken up in $CH_2Cl_2$. The solution is washed with pH 7 phosphate buffer dried and evaporated. Column chromatography

of the residue gives 0.455 g (0.000575 mole, 68% yield) of the product.

nmr/CDCl₃ (δ):

1.31 (d, CH₃)
2.40–4.50 (m, C₃—H, C₆—H), CH₂—OAc

5.00–6.00 (m, ArCH₂, —N—C)
         H  O 7.28–8.10 (m, ArH)

ir/neat (μm): 3.0 (broad NH & OH); 5.65–5.88 (β-lactam, carbonate); 6.17 (ester carbonyl).

Step J

Preparation of o-nitrobenzyl 1-carba-2-penem-6α-(1-o-nitrobenzyloxycarbonylaminoethyl)-3-carboxylate

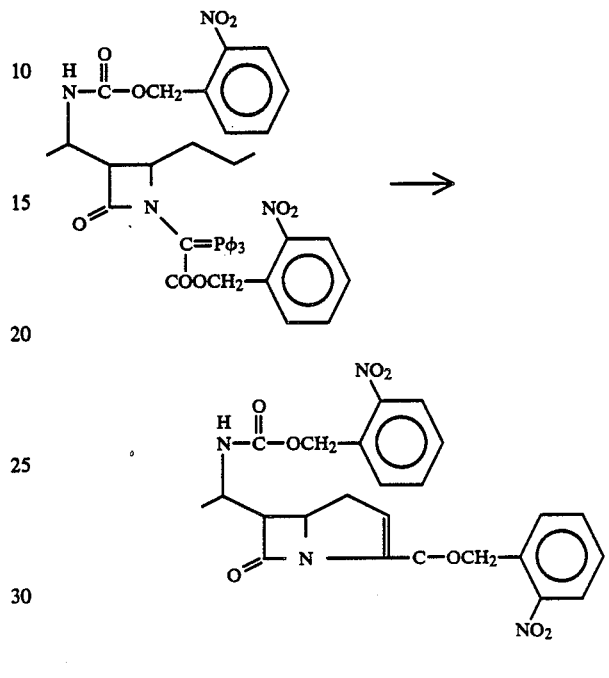

Trans-1-(o-nitrobenzyloxycarbonyltriphenylphosphoranylmethyl)-3-(1-o-nitrobenzyloxycarbonylaminoethyl)-4-(2'-hydroxyethyl)-2-azetidinone (0.0792 g, 0.00010 mole) is dissolved in 4 ml DMSO/Ac₂O (1:1) under N₂ at 3 hr; DMSO and Ac₂O is removed under vacuum. The residue is purified by preparative TLC

to give 0.1260 g (0.0247 mmole, 25% yield) of the product.

nmr/CDCl₃ (δ):

1.40 (q, CH₃)
2.91 (m, C₁—H)
3.45 (m, C₆—H)

4.25 (m, C₅—H & )

5.05 (d, N—H)
5.50–5.83 (m, CH₂—Ar)
6.60 (m, C≡C—H)
7.33–8.33 (m, Ar—H)

ir/neat (μm) 3.0 (N—H); 5.63 (β-lactam C=O); 5.81 (ester, carbamate, C=O); 6.58 & 7.46 (NO₂).

Step K

Preparation of Sodium 1-carba-2-penem-6α(1-o-nitrobenzyloxycarbonylaminethyl)-3-carboxylate

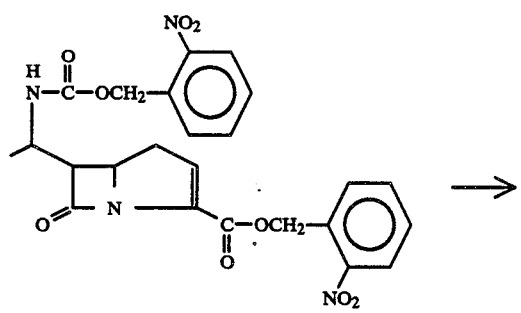

Ortho-nitrobenzyl 1-carba-2-penem-6α-(1-o-nitrobenzyloxycarbonylaminoethyl)-3-carboxylate, 2.1 mg, is dissolved in 2 ml p-dioxane and 2 ml water containing 0.01 ml 0.50N pH 7 phosphate buffer. The solution is deoxygenated and then exposed to 350 nm light for 1 hr. The solution is extracted thoroughly with ethyl acetate. The aqueous solution is freeze dried to give the product. u.v. $_{max}$ 265 nm, Electrophoresis shows single bioactive spot moving towards the anode.

Step L

Preparation of 1-carba-2-penem-6-α(1-aminoethyl)-3-carboxylic acid

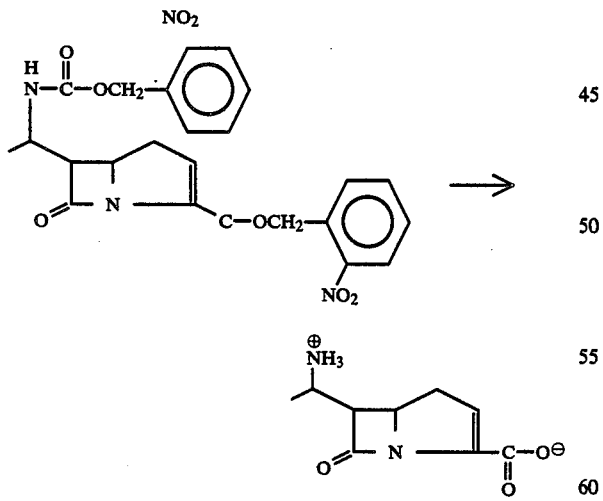

Ortho-nitrobenzyl 1-carba-2-penem-6α(1-o-nitrobenzyloxycarbonylaminoethyl)-3-carboxylate, 4.0 mg, is dissolved in 4 ml p-dioxane and 4 ml water containing 0.03 ml 0.50N pH 2 phosphate buffer. The solution is deoxygenated and exposed to 350 nm light for 2½ hrs. The solution is neutralized by adding 0.04 ml 0.50N pH 7 phosphate buffer and then extracted thoroughly with ethyl acetate. The aqueous solution is freeze dried to give the product.

u.v. $\lambda_{max}$ 265 nm.

Electrophoresis shows a single bioactive spot which moves as a zwitterion.

EXAMPLE 44

Preparation of Sodium 1-carba-2-penem-6α-(1-hydroxy-1-methyl)ethyl-3-carboxylate

Step A

Preparation of 8-oxo-2,2-dimethyl-7α and β-(1-hydroxy-1-methyl)ethyl-3-oxa-1-azabicyclo[4.2.0]octane

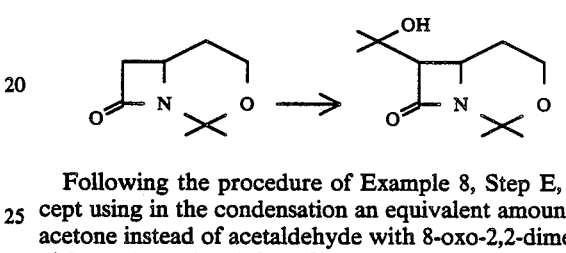

Following the procedure of Example 8, Step E, except using in the condensation an equivalent amount of acetone instead of acetaldehyde with 8-oxo-2,2-dimethyl-3-oxa-1-azabicyclo[4.2.0]octane there is obtained, in 75% yield, the title product.

nmr/CDCl$_3$ (δ):

1.23 & 1.30 (S, C$\underline{H}_3$—C—OH) 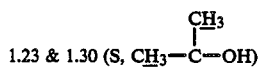

1.37 & 1.70 (S, 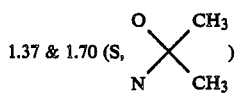 )

1.60–1.90 (m, C$\underline{H}_2$—CH$_2$—O)
2.80 (d, C$_7$—H), J$_{67}$=2.0)
2.93 (S, OH)
3.40–3.63 (two triplets, C$_6$—H, J$_{67}$=2.0)
3.73–3.93 (m, C$_4$—H)

ir/film (μm) 2.90 (OH); 5.78 (C=O).

Step B

Preparation of trans-3-(1-hydroxy-1-methyl)ethyl-4-(2'-acetoxyethyl)-2-azetidinone

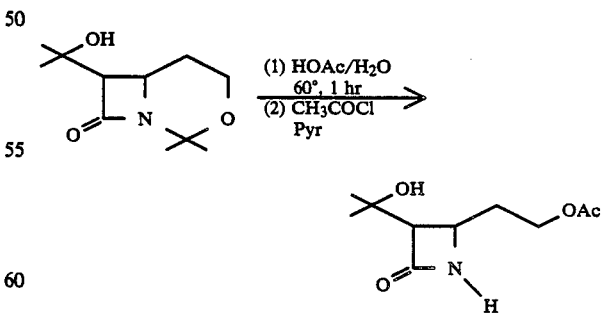

Hydrolysis of 8-oxo-,2,2-dimethyl-7α-(1-hydroxy-1-methyl)-ethyl-3-oxa-1-azabicyclo[4.2.0]octane as described in Step C, Example 43, followed by acylation of the product according to Step C, Example 43 gives trans-3-(1-hydroxy-1-methyl)ethyl-4-(2-acetoxyethyl)-2-azetidinone in 45% yield.

nmr/CDCl₃ (δ):

1.23 & 1.33 (2S, CH₃—C(CH₃)—)
1.70–2.20 (m, —CH₂—)
2.03 (s, CH₃—CO)
2.85 (d, C₃—H, J₃,₄ = 2.0)
3.20 (broad, OH)
3.53–3.83 (two triplets, C₄—H J₃,₄ = 2.0)
4.03–4.26 (m, —CH₂—O)
7.0 (broad, NH)

ir/film (μm) 3.0 (broad, NH & OH); 5.78 (C=O, β-lactam ester) 8.06 (OAC)

Step C

Preparation of trans 1-(o-nitrobenzyloxycarbonylhydroxymethyl)-3-(1-hydroxy-1-methyl)ethyl-4-(2'-acetoxyethyl)-2-azetidinone

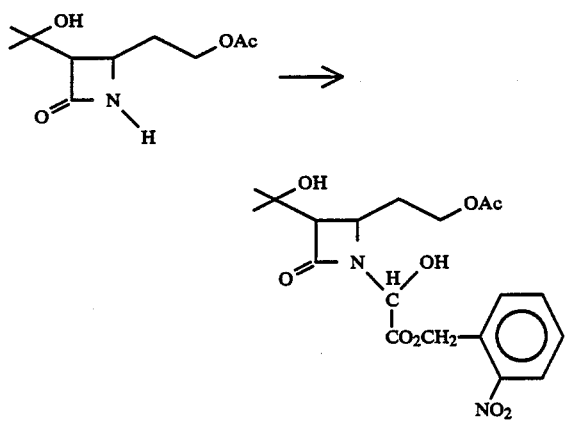

Condensation of trans-3-(1-hydroxy-1-methyl)ethyl-4-β-acetoxyethyl)-2-azetidinone with o-nitrobenzylglyoxylate as described in Step F Example 43 gives the desired product in 66% yield.

nmr/CDCl₃ (δ):

1.26–1.43 (two doublets, CH₃—C(CH₃)—OH)

2.03 (S, CH₃CO)
1.80–2.30 (m, —CH₂—)
3.00 (d, C₃—H)

3.28 (s, (CH₃)₂—OH)

3.80–4.40 (m, C₄—H & CH₂—O)

5.10–5.80 (m, N—C(H)(OH), & CH₂—Ar)

7.50–8.30 (m, Ar—H)

ir/neat (μm) 2.90 (O—H's) 5.71 (C=O, β-lactam ester); 6.58 & 7.46 (NO₂).

Step D

Preparation of trans-1-(o-nitrobenzyloxycarbonyltriphenylphosphoranylmethyl)-3-(1-hydroxy-1-methyl)ethyl-4-(2-acetoxyethyl)-2-azetidinone

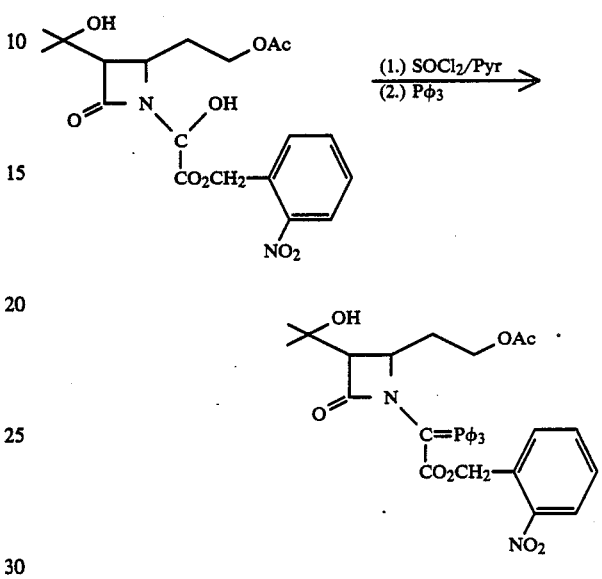

(1.) SOCl₂/Pyr
(2.) Pφ₃

Reaction of trans-1-(o-nitrobenzyloxycarbonylhydroxymethyl)-3-(1-hydroxy-1-methyl)ethyl-4-(2-acetoxyethyl)-2-azetidinone with thionylchloride and pyridine as described in Step G, Example 43 gives the desired chloro compound which is reacted with triphenylphosphine as in Step H, Example 43 to give the desired product in 63% yield.

NMR/CDCl₃ (δ):

1.00–1.40 (S, broad, CH₃—C(CH₃)—OH)

2.01 (S, CH₃CO)
1.80–2.60 (m, —CH₂— & OH)
2.90 (d, C₃—H)
3.60–4.40 (m, C₄—H & CH₂—O)
5.0–5.80 (m, CH₂Ar)
7.20–8.10 (m, ArH)

ir/neat (μm):

2.95 (O—H)
5.78 (C=O, β-lactam & acetate)

6.17 (C=Pφ₃, C=O)

Step E

Preparation of trans-1-(o-nitrobenzyloxycarbonyltriphenylphosphoranylmethyl)-3-(1-hydroxy-1-methyl)ethyl-4-(2'-hydroxyethyl)-2-azetidinone

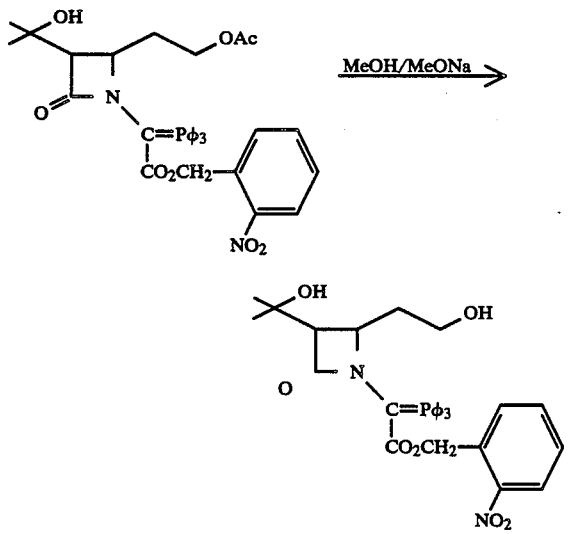

Hydrolysis of trans-1-(o-nitrobenzyloxycarbonyltriphenylphosphoranylmethyl)-3-(1-hydroxy-1-methhl)ethyl-4-(2-acetoxyethyl)2-azetidinone with sodium methoxide and methanol as described in Step I Example 43 gives the desired product in 93% yield.

nmr/CDCl$_3$ ($\delta$):

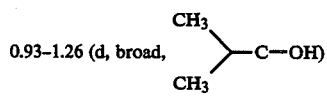

0.93–1.26 (d, broad, $CH_3{>}C{-}OH$ with $CH_3$)

1.80–2.60 (m, —CH$_2$— & OH's)
2.86 (d, C$_3$—H)
3.10–3.90 (m broad, C$_4$—H's & CH$_2$O)
4.80–5.50 (m, CH$_2$ Ar)
7.10–8.00 (m, ArH)

ir/film ($\mu$m):

2.98 (O—H's)
5.78 (C═O, $\beta$-lactam)

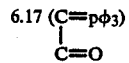
6.17 (C═p$\phi_3$) with C═O

Step F

Preparation of o-nitrobenzyl 1-carba-2-penem-6-$\alpha$-(1-hydroxy-1-methyl)ethyl-3-carboxylate

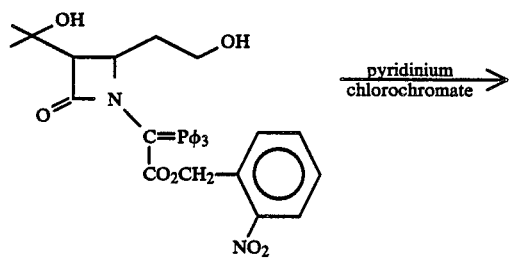

-continued

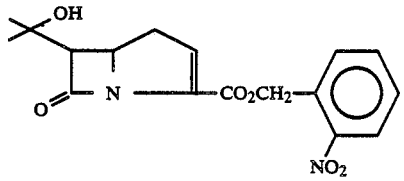

Trans-1-(o-nitrobenzyloxycarbonyltriphenylphosphoranylmethyl)-3-(1-hydroxy-1-methyl)ethyl-4-(2-acetoxyethyl)-2-azetidinone (0.1252 g, 0.00020 mole) is dissolved in 10 ml CH$_2$Cl$_2$ and slowly added to 20 ml CH$_2$Cl$_2$ suspension of pyridinium chlorochromate at 25° C. over 20 min. After completion of addition, the stirring is continued for another 30 min. The reaction mixture is then filtered and the filtrate is washed with pH 3, then pH 7 buffer solution, dried over anhydrous MgSO$_4$ and evaporated. Preparative TLC (silica gel, EtOAc) gives 0.0248 g (0.0716 mmole, 36% yield) of the product and 0.0344 g (0.0550 mmole, 27%) of the starting material recovered.

nmr/CDCl$_3$ ($\delta$):

1.35 & 1.43 (2S, CH$_3$—$\overset{CH_3}{\underset{}{C}}$—OH)

1.83 (broad, OH)
2.91 (two triplets, C$_1$—H)
3.33 (d, C$_6$—H, J$_{5,6}$ = 3.0)
4.33 (two triplets, C$_5$—H, J$_{5,6}$ = 3.0)
5.71 (q, CH$_2$AR)
6.58 (t, C═CH)
7.30–8.30 (m, Ar)

ir/thin film ($\mu$m) from CH$_2$Cl$_2$: 3.0 (Broad, O—H); 5.65 (C═O, $\beta$-lactam); 5.81 (C═O, ester); 6.25 (C═C); 6.58 & 7.46 (NO$_2$).

Step G

Preparation of Sodium 1-carba-2-penem-6$\alpha$(1-hydroxy-1-methyl)ethyl-3-carboxylate

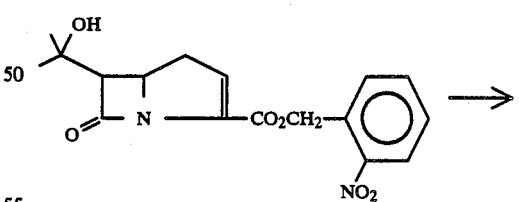

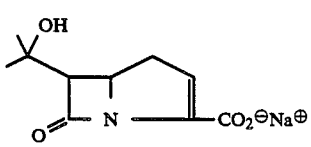

PHotolysis of o-nitrobenzyl-1-carba-2-penam-6$\alpha$(1-hydroxy-1-methyl)ethyl-3-carboxylate as described in Step F Example 39 gives sodium 1-carba-2-penem-6$\alpha$(1-hydroxy-1-methyl)ethyl-3-carboxylate.

uv/H$_2$O (m$\mu$) $\lambda_{max}$=265.

nmr/D$_2$O Varian SC-300 ($\delta$):

1.31 & 1.36 (S, CH₃—C ); CH₃

2.90 (m, C₁—H's)
3.47 (d, C₆—H)
4.27 (two triplets, C₅—H)
6.30 (t, C=CH)

EXAMPLE 45

Preparation of Sodium 1-carba-2-(p-methoxyphenyl)-6α-(1(S)-hydroxyethyl)-2-penem-3-carboxylate Step A 8-oxo-2,2-dimethyl-7α-(1-o-nitrobenzyloxycarbonyloxyethyl)-3-oxa-1-azabicyclo-[4.2.0]-octane

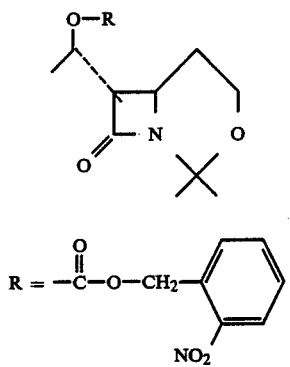

$R = -\overset{O}{\underset{\|}{C}}-O-CH_2-\text{(o-NO}_2\text{-phenyl)}$

8-Oxo-2,2-dimethyl-7,α-(1-hydroxyethyl)-3-oxo-1-aza-bicyclo[4.2.0]-octane (3.0 g, 0.015 m) is dissolved in 40 ml THF and cooled to −78° under N₂. Methyl Lithium (13.3 ml, 1.3 m solution in Et₂O/C₆H₆) is added dropwise over 5 minutes and the mixture is stirred for 10 minutes; o-nitrobenzyloxycarbonylchloride (3.56 g, 0.0165 m) in 20 ml THF is added dropwise over 10 minutes and the mixture is stirred at −78° C. for 45 minutes. The mixture is treated with 20 ml of pH 7 phosphate buffer (0.5 m) and water. The organic phase is separated and the aqueous phase is extracted with CH₂Cl₂. The combined organic extract is dried and evaporated. The residue is chromatographed on silica gel using 50% EtOAc/cyclohexane to give 8-oxo-2,2-dimethyl-7α-(1(R)-o-nitrobenzyloxycarbonyloxyethyl)-3-oxa-1-azabicyclo-[4.2.0]-octane. (0.717 g)

i.r. cm⁻¹: 1760 δ lactam, 1730 carbonate, 1512 nitro.
n.m.r.δ:

1.41 & 1.73, 2s (gem dimethyl); 1.45 d (C<u>H</u>₃—C);
                                              |
                                              <u>H</u>

1.85 m (C-5 H); 2.96 d of d, (j = 2, j = 8, C-7 H);

3.53 m (C-6 H); 3.81 d of d (C-4 H); 5.03 m (CH₃—C);
                                                |
                                                H 5.53 s (Ar—C<u>H</u>₂—O); 7.35–8.15 m (Ar<u>H</u>)

and 8-oxo-2,2-dimethyl-7α-[1(S)—o-nitrobenzyloxycarbonyloxyethyl]-3-oxa-1-azabicyclo-[4.2.0]-octane.

(0.670 g)

i.r. cm⁻¹: 1760 (β lactam), 1730 carbonate, 1512 nitro.
n.m.r.δ:

1.4 & 1.73, 2s (gem dimethyl); 1.5 d (CH₃—C<);
                                           H 1.85 m (C-5 H); 3.14 d of d (j = 2, j = 5), C-7 H);
3.53 m (C-6 H); 3.85, d of d (C-4 H); 5.2 m
(CH₃—C—<u>H</u>); 5.56 s, (ArCH₂—o); 7.9–8.25 m (Ar H)

and a fraction (1.707 g) which is a mixture of the two isomers which can be separated by repeated chromatography.

Step B trans-3-[1(S)-o-nitrobenzyloxycarbonyloxyethyl]-4-(2-hydroxyethyl)-2-azetidinone

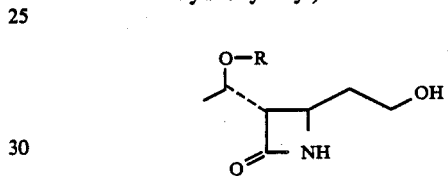

8-Oxo-2,2-dimethyl-7α-[1(S)-o-nitrobenzyloxycarbonyloxyethyl]-3-oxa-1-azabicyclo-[4.2.0]-octane (1.38 g) is dissolved in acetic acid (16 ml) and water (4 ml) is added and the mixture is heated at 65° C. for 1.5 hours. The solvent is removed under reduced pressure and the residue taken up in 10 ml xylene which is evaporated off under reduced pressure and this process is repeated twice. The residue is the crude trans-3[1(S)-o-nitrobenzyloxycarbonyloxyethyl]-4-(2-hydroxyethyl)-2-azetidinone, which is used in the next step without further purification.

Step C trans 1-(o-nitrobenzyloxycarbonylhydroxymethyl)-3-[1(S)-o-nitrobenzyloxycarbonyoxyethyl]-4-(2-hydroxyethyl)-2-azetidinone

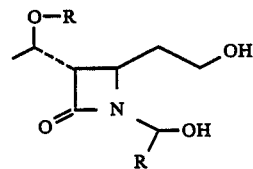

To trans-3[1(S)-o-nitrobenzyloxycarbonyloxyethyl]-4-(2-hydroxyethyl)-2-azetidinone from Step B in benzene (20 ml) is added o-nitrobenzylglyoxalate (prepared from 1.55 g di-o-nitrobenzyltartarate and 0.92 g periodic acid as described in Step A, Example 1 for benzylglyoscalate). The mixture is refluxed overnight using a Dean-Stark apparatus with CaH₂ to trap the water. The mixture is cooled, filtered evaporated and chromatographed on silica gel using 70% EtOAC/C₆H₁₂ as eluant to give the diol (0.825 g).

i.r. cm$^{-1}$: 3400 (OH); 1740 (β lactam, carbonate ester) 1520 (nitro).

n.m.r.δ:

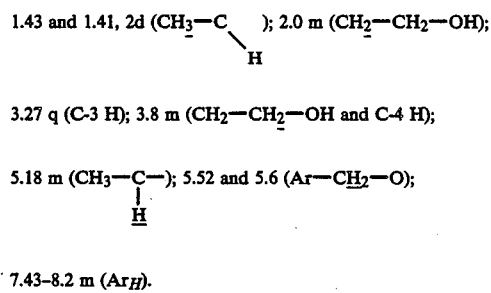

1.43 and 1.41, 2d (CH$_3$—C, H); 2.0 m (CH$_2$—CH$_2$—OH);

3.27 q (C-3 H); 3.8 m (CH$_2$—CH$_2$—OH and C-4 H);

5.18 m (CH$_3$—C—H); 5.52 and 5.6 (Ar—CH$_2$—O);

7.43–8.2 m (Ar H).

Step D trans 1-(o-nitrobenzyloxycarbonylhydroxymethyl)-3-[1(S)-o-nitrobenzyloxycarbonyloxyethyl]-4-(2-t-butyldimethylsilyloxy)ethyl-2-azetidinone

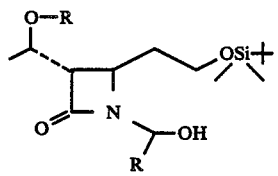

trans 1-(o-nitrobenzyloxycarbonylhydroxymethyl)-3-[1(S)-o-nitrobenzyloxycarbonyloxyethyl]-4-(2-hydroxyethyl)-2-azetidinone (0.825 g) is dissolved in 10 ml DMF and treated with t-butyldimethylchlorosilane (0.250 g) and triethylamine 0.233 g. The mixture is allowed to stir at r.t. for ½ hour. Water is added and the mixture is extracted with ether 3 times. The ether extract is washed with water 4 times, then dried evaporated and the residue chromatographed on silica gel using 50% EtOAc/C$_6$H$_{12}$ to give the silyl ether 0.845 g.

i.r. cm$^{-1}$: 3350 (OH); 1750 (β-lactam, ester & carbonate); 1525 (nitro).

n.m.r.δ:

0.06 s (CH$_3$Si); 0.86 s (CH$_3$—C—Si); 1.43 d (CH$_3$—C);

2.03 m (CH$_2$—CH$_2$—O); 3.26 q (C-3 H); 3.76 m (CH$_2$—CH$_2$—O and C-4 H); 5.06 m (CH$_3$—C—H); 5.53 and 5.63 (Ar—CH$_2$—O); 7.33–8.26 m (Ar H).

Step E trans-1-(o-nitrobenzyloxycarbonyltriphenylphosphoranylmethyl)-3-[1(S)-o-nitrobenzyloxycarbonyloxyethyl]-4-(2-hydroxyethyl)-2-azetidinone

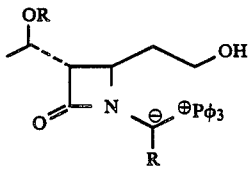

Trans 1-(o-nitrobenzyloxycarbonylhydroxymethyl)-3-[1(S)-o-nitrobenzyloxycarbonyloxyethyl]-4-(2-t-butyldimethylsilyloxy)ethyl-2-azetidinone (0.845 g) is treated with SOCl$_2$ (0.11 ml) and pyridine (0.13 ml) according to the procedure described in Example I Step B and the chloro compound so obtained is treated with triphenylphosphine (0.397 g) following the procedure of Example I Step C to give the DMF solution of the ylidsilylether. To this solution is added 0.1 ml concentrated HCl, the mixture is allowed to stir at 25° C. for 10 minutes. The solvent is removed under reduced pressure and the residue is taken up in CH$_2$Cl$_2$ and washed with 5% NaHCO$_3$ solution, dried evaporated and chromatographed on silica gel using 70% EtOAc/C$_6$H$_{12}$ to give trans-1-(o-nitrobenzyloxycarbonyltriphenylphosphoranylmethyl)-3-[1(S)-o-nitrobenzyloxycarbonylethyl]-4-(2-hydroxyethyl)-2-azetidinone (0.750 g).

i.r. cm$^{-1}$: 3400 (OH); 1740 (β-lactam, and carbonate); 1620 (ester); 1522 (nitro).

n.m.r.δ:

1.36 d (CH$_3$—C—H); 1.9 m (CH$_2$—CH$_2$—OH); 3.58 m and 3.8 m (CH$_2$—CH$_2$ OH and C-4 H); 5.12 m (CH$_3$—C—H);

5.2–5.85 m (Ar CH$_2$—O); 7.4–8.2 m (Ar H).

m.s.: m$^+$ = 792.

Step F trans-1-(o-nitrobenzyloxycarbonyltriphenylphosphoranylmethyl)3-[1(S)-o-nitrobenzyloxycarbonyloxyethyl]-4-(carboxylmethyl)-2-azetidinone

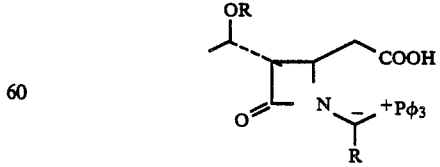

The product of Step E (0.700 g) is oxidized with Jones Reagent following the procedure of Step A Example 39 to give the carboxylic acid.

Step G trans-1-(o-nitrobenzyloxycarbonyltriphenylphosphoranylmethyl)-3-[1(S)-o-nitrobenzyloxycarbonyloxyethyl]-4-(chlorocarbonylmethyl)-2-azetidinone

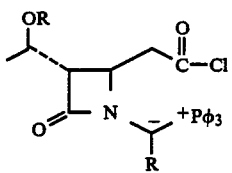

The product of Step F is treated with oxalyl chloride following the procedure of Step B Example 39 to give the acid chloride.

Step H trans-1-(o-nitrobenzyloxycarbonyltriphenylphosphoranylmethyl)-3-[1(S)-o-nitrobenzyloxycarbonyloxyethyl]-4-[phenylthiocarbonylmethyl]-2-azetidinone

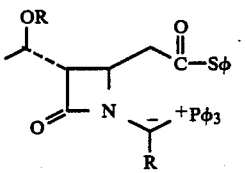

The product from Step G is treated with thiophenol and pyridine following the procedure described in Step C Example 39 to give the thioester (0.586 g).

i.r. cm$^{-1}$: 1750 ($\beta$ lactam and carbonate); 1700 (thioester); 1620 (ester); 1520 (nitro).

Step I trans-1-(o-nitrobenzyloxycarbonyltriphenylphosphoranylmethyl)-3-[1(S)-o-nitrobenzyloxycarbonyoxyethyl]-4-(p-methoxyphenylcarbonylmethyl)-2-azetidinone

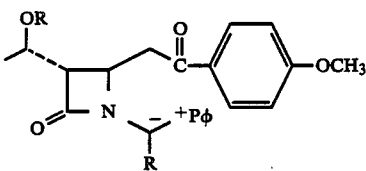

A solution (4 ml, 0.25 m) of p-methoxyphenyl magnesium bromide is placed in a dry flask under $N_2$ and cooled to 0°. Cu I (0.110 g) is added and the mixture is stirred under $N_2$ for 0.5 hour. The thioester from Step H (0.224 g) dissolved in THF (5 ml) is added dropwise followed by $Et_2O$ (5 ml). The mixture is stirred at 0°–5° for 45 minutes. Saturated $NH_4Cl$ is added and the mixture is stirred open to air for 15 minutes. $CH_2Cl_2$ is added and the layers are separated. The aqueous layer is extracted once with $CH_2Cl_2$ and the total organic phase is dried and evaporated. Purification by preparative t.l.c. gives the ketone (0.138 g).

i.r. cm$^{-1}$: 1742 ($\beta$-lactam and carbonate); 1670 (ketone); 1620 (ester), 1520 (nitro).

n.m.r.: 3.92 (OCH$_3$).

Step J o-nitrobenzyl-1-carba-2-(p-methoxyphenyl)-6$\alpha$-[1(S)-o-nitrobenzyloxycarbonyoxyethyl]-2-penem-3-carboxylate

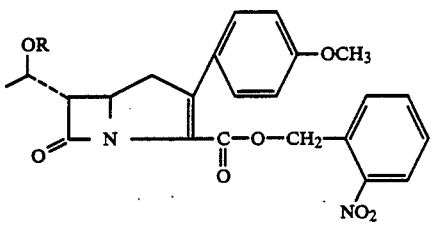

Trans-1-(o-nitrobenzyloxycarbonyltriphenylphosphoranylmethyl)-3-[1(S)-o-nitrobenzyloxycarbonyloxyethyl]-4-(p-methoxyphenylcarbonylmethyl)-2-azetidinone (0.138 g) is dissolved in 6 ml xylene and heated under $N_2$ for 1 hour by an oil bath at 145°. The mixture is cooled, the solvent evaporated under reduced pressure and the residue purified by preparative t.l.c. to give the cyclized product (0.017 g) and recovered starting material (0.102 g). This recovered ketone is heated in xylene as described above for another 3 hours to give after purification by preparative t.l.c. on silica gel 50% EtOAC/C$_6$H$_{12}$ eluant to give 0.037 g of cyclized product. Total yield 0.054 g (57% yield).

i.r. cm$^{-1}$: 1775 ($\beta$-lactam); 1745 (carbonate); 1720 (ester); 1605 (c=c); 1520 (nitro).

n.m.r. $\delta$: 1.56 d (CH$_3$—CH); 3.3 d of d (C-1H); 3.63 m (C-6H); 3.8 s (OCH$_3$); 4.2 m (C-5H); 5.3 m (CH$_3$—C$\underline{H}$); 5.63 (ArCH$_2$O); 6.8 to 8.3 m (Ar$\underline{H}$).

Step K

Sodium 1-carba-2-(p-methoxyphenyl)-6$\alpha$-[1(S)-hydroxyethyl]-2-penem-3-carboxylate

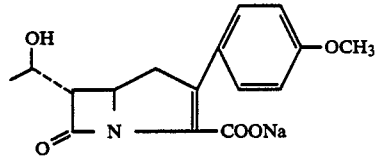

The product of Step J (0.020 g) is dissolved in 6 ml dioxane, 2.7 ml of a 1 mg/ml solution of NaHCO$_3$ is added followed by 3.3 ml of H$_2$O and 1.2 ml ETOH; Pd/C 10% (0.020 g) is added and the mixture is hydrogenated at 40 lbs. H$_2$ pressure for 1 hour. The catalyst is filtered off and washed with water. The filtrate and washings are extracted with 3×15 ml EtOAC and the aqueous phase is free-dried to give sodium 1-carba-2-(p-methoxyphenyl)-6$\alpha$-[1(S)-hydroxyethyl]-2-penem-3-carboxylate.

U.V. $\lambda$max. 312 (NH$_2$OH extinguishable).

EXAMPLE 46

1-Carba-2-phenyl-2-penem-6$\alpha$-(1-aminoethyl)-3-carboxylate

Step A trans
1-(o-nitrobenzyloxycarbonyltriphenylphosphoranylmethyl)-3-(1-o-nitrobenzyloxycarbonylaminoethyl)-4-(carboxymethyl)-2-azatidinone

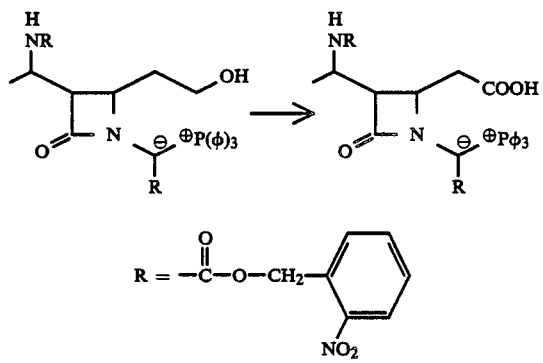

$$R = -\overset{O}{\underset{\|}{C}}-O-CH_2-\phantom{-}\text{(o-NO}_2\text{-phenyl)}$$

1-(o-Nitrobenzyloxycarbonyltriphenylphosphoranylmethyl)-3-(1-o-nitrobenzyloxycarbonylaminoethyl)-4-(2'-hydroxyethyl)-2-azetidinone (0.1582 g, 0.20 mmole) (cf. Example 43, Step I) is dissolved in 5 ml acetone cooled to 0°. Jones Reagent (0.12 ml, 4N solution) is added dropwise over 3 minutes and the resulting solution is stirred at 0° for 10 minutes. Isopropanol (0.05 ml) is added and the mixture stirred for another 2 minutes. The reaction mixture is diluted with CH$_2$Cl$_2$ and filtered. The filtrate is washed with saturated NaCl aqueous solution, dried and evaporated to give 0.132 g of crude acid which was used without further purification in the next step.

i.r./neat (cm$^{-1}$):

| O |
|---|
| 2300–3500 (NH and C—OH) |
| 1670–1770 ($\beta$-lactam, carbamate, and acid carbonyl)<br>1620 (ester carbonyl)<br>1345 and 1520 (NO$_2$) |

Step B trans
1-(o-nitrobenzyloxycarbonyltriphenylphosphoranylmethyl)-3-(1-o-nitrobenzyloxycarbonylaminoethyl)-4-(chlorocarbonylmethyl)-2-azetidinone

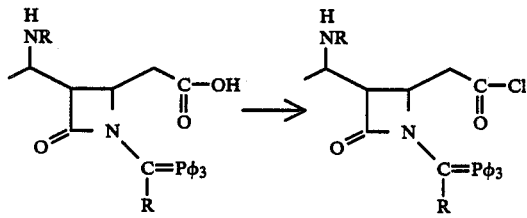

1-(o-nitrobenzyloxycarbonyltriphenylphosphoranylmethyl)-3-(1-o-nitrobenzyloxycarbonylaminoethyl)-4-(carboxymethyl)-2-azetidinone (0.1320 g from the previous step) is dissolved in 5 ml CH$_2$Cl$_2$ and cooled to 0° under N$_2$. Oxalyl chloride (0.040 ml, 0.44 mmole) is added dropwise over 5 minutes and then 1 drop of DMF is added. The mixture is stirred at 0° for 5 minutes and then at 25° C. for another 15 minutes. The solvent and excess oxalyl chloride are evaporated under reduced pressure. The residue is then desired acid chloride which is used without purification in the next step.

Step C trans
1-(o-nitrobenzyloxycarbonyltriphenylphosphoranylmethyl)-3-(1-o-nitrobenzyloxycarbonylaminoethyl)-4-(phenylthiocarbonylmethyl)-2-azetidinone

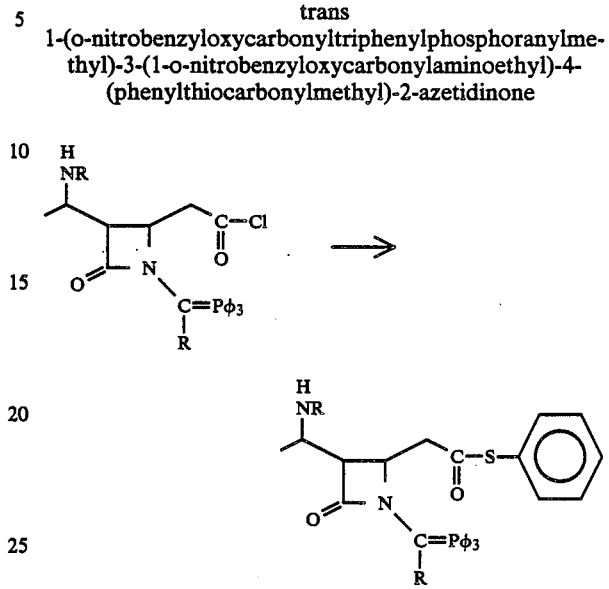

1-(o-nitrobenzyloxycarbonyltriphenylphosphoranylmethyl)-3-(1-o-nitrobenzyloxycarbonylaminoethyl)-4-(chlorocarbonylmethyl)-2-azetidinone (from the previous step) is dissolved in 5 ml CH$_2$Cl$_2$ and cooled to 0° under N$_2$. Thiophenol (0.045 ml, 0.44 mmole) is added and then pyridine (0.090 ml, 1.1 mmole) is added dropwise. The reaction mixture is stirred at 0° for 5 minutes and then at 25° C. for 15 minutes, then diluted with CH$_2$Cl$_2$ and washed with water, dried and evaporated. The residue is chromatographed on silica gel using 50% EtOAc/C$_6$H$_6$ as eluant, to give the desired product (0.1080 g, 0.120 mmole).

i.r./neat (cm$^{-1}$): 3300 (broad, NH); 1710–1760 ($\beta$-lactam, carbamate); 1700 (thioester); 1620 (ester); 1345 and 1520 (NO$_2$).

Step D trans
1-(o-nitrobenzyloxycarbonyltriphenylphosphoranylmethyl)-3-(1-o-nitrobenzyloxycarbonylaminoethyl)-4-(phenylcarbonylmethyl)-2-azetidinone

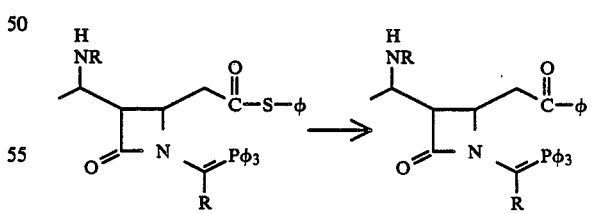

A solution of phenyl magnesium bromide (0.25 m in Et$_2$O, 2.6 ml) is cooled to 0° under N$_2$. Cuprous iodide (61. mg, 0.32 mmol) is added and the mixture is stirred at 0° for ½ hour.

1-(o-nitrobenzyloxycarbonyltriphenylphosphoranylmethyl)-3-(1-o-nitrobenzyloxycarbonylaminoethyl)-4-(phenylthiocarbonylmethyl)-2-azetidinone (64. mg, 0.071 mmole) in 2 ml THF is added dropwise. The mixture is allowed to stir at 0° for 1 hour. A saturated NH$_4$Cl aqueous solution is added and the mixture is allowed to stir for 10 minutes. The organic phase is separated. The aqueous phase is extracted twice with CH₂Cl₂. The combined organic extracted is dried and evaporateed. Preparative t.l.c. of the residue using silica gel and 50% EtOAc/benzene gives starting material (27 mg, 0.031 mmole) and recovered starting material (25 mg, 0.028 mmole).

i.r./neat (cm⁻¹): 3300 (broad, NH); 1710~1750 (β-lactam, carbamate); 1670 (ketone); 1620 (ester); 1345 and 1520 (NO₂).

Step E

O-nitrobenzyl-1-carba-2-phenyl-2-penem-6α-(1-o-nitrobenzyloxycarbonylaminoethyl)-3-carboxylate

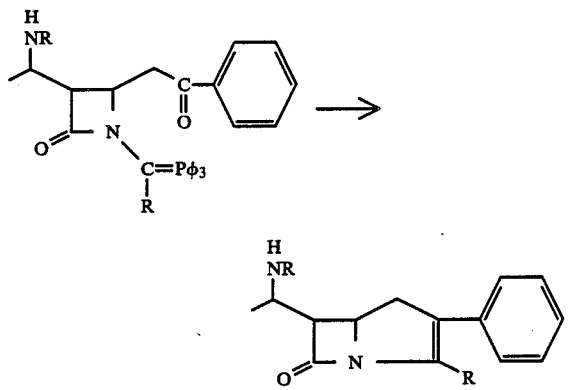

1-(o-nitrobenzyloxycarbonyltriphenylphosphoranyl-methyl)-3-(1-o-nitrobenzyloxycarbonylaminoethyl)-4-(phenylcarbonylmethyl)-2-azetidinone (42 mg, 0.049 mmole) is dissolved in 5 ml xylene, placed under N₂ and heated at 140° for 1 hour. The xylene is removed under reduced pressure and the residue is purified by preparative t.l.c. (silica gel G, 50% EtOAc/benzene) to give the desired product (6. mg, 0.010 mmole) and recovered starting material (22. mg, 0.025 mmole).

i.r./neat (cm⁻¹): 3350 (broad, N—H); 1770 (β-lactam); 1720 (ester and carbamate); 1610 (c=c); 1525 and 1345 (NO₂).

n.m.r./CDCl₃ (δ): 7.00~8.20 (m, ArH); 5.20~5.80 (m, ArCH₂); 5.01 (broad, NH); 4.33 (m, C₅—H); 3.58 (m, C₆—H); 3.33 (q, C₁—H); 1.48 (d, CH₃).

Step F

1-Carba-2-(phenyl)-2-penem-6α-(1-aminoethyl)-3-carboxylate

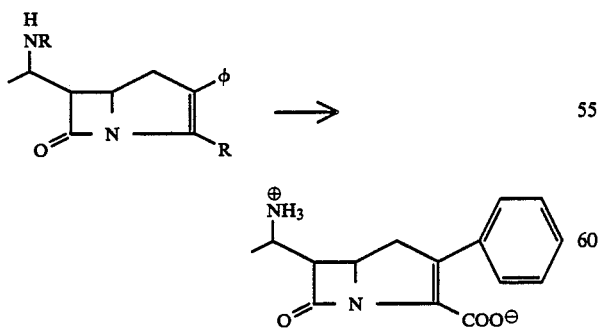

The product of Step F (1 mg, 0.0017 mmole) is dissolved in 2 ml p-dioxane, 0.2 ml EtOH and 2 ml H₂O. The mixture is photolyzed at 350 mm for 1 hour under N₂. The solution is extracted with 3 portions of 10 ml ETOAc and the aqueous solution is freeze dried to give 1-carba-2-(phenyl)-2-penem-6-(1-aminoethyl)-3-carboxylate.

U.V. λmax 297 nm.

EXAMPLE 47

1-Carba-2-(p-methoxyphenyl)-2-penem-6α-(1-aminoethyl)-3-carboxylate

Step A trans 1-(o-nitrobenzyloxycarbonyltriphenylphosphoranylme-thyl)-3-(k-o-nitrobenzyloxycarbonylaminoethyl)-4-(p-methoxyphenyl)-2-azetidinone

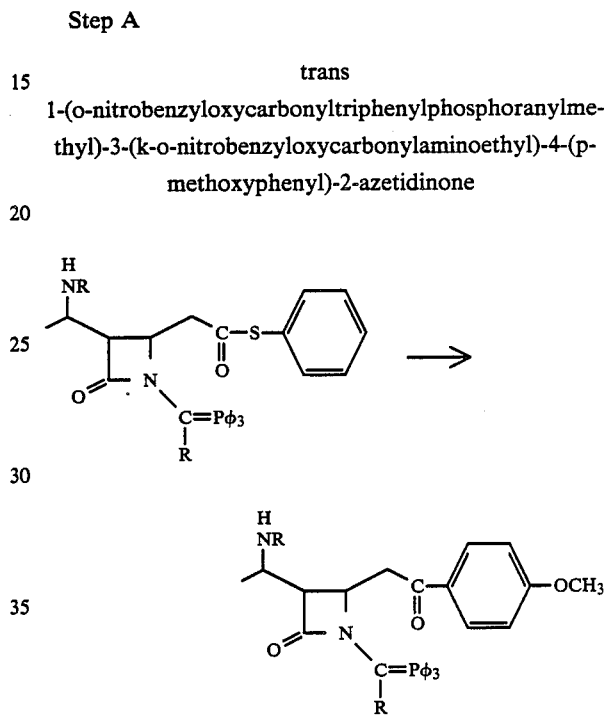

Following the procedure of Step D Example 40, but using p-methoxyphenyl magnesium bromide instead of phenyl magnesium bromide the desired ketone is obtained.

i.r./neat (cm⁻¹): 3300 (broad, NH); 1710–1750 (β-lactam, carbamate); 1660 (ketone); 1620 (ester); 1345 and 1520 (NO₂).

n.m.r./CDCl₃ (δ):

| |
|---|
| 6.8–8.2 (m, ArH) |
| 5.1–5.8 (m, ArCH₂ and N<u>H</u>) |
| 3.77 and 3.87 (two singlet, OCH₃, 2 isomers) |
| 1.07 and 1.27 (two doublets, CH₃, 2 isomers) |
| 2.7 m (C<u>H</u>₂—C(=O)) |
| 2.9 m (C—3 H) |

Step B trans o-nitrobenzyl-1-carba-2-(p-methoxyphenyl)-2-penem-6-(1-o-nitrobenzyloxycarbonylaminoethyl)-3-carboxylate

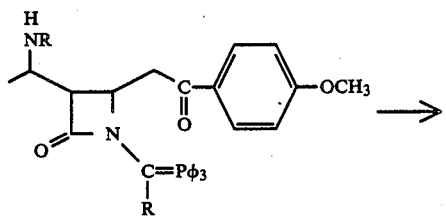

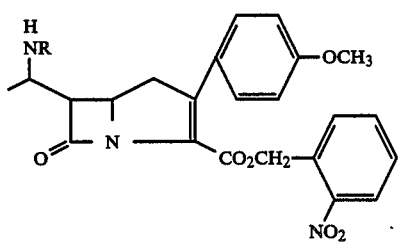

Following the procedure of Step E Example 40 on the p-methoxy phenyl ketone one obtains the desired cyclized compound.

i.r./neat (cm$^{-1}$): 3350 (broad, N—H); 1770 (β-lactam); 1720 (ester); 1605 (c=c); 1525 and 1345 (NO$_2$).

n.m.r./CDCl$_3$ (δ): 6.8–8.3 (m, ArH); 5.2–5.8 (m ArCH$_2$); 3.83 (s, OCH$_3$); 3.3, d of d (C-1H); 3.5, m (C-6H); 4.25 m (C-5H and CH$_3$—CH).

Step C 1-carba-2-pmethoxyphenyl-2-penem-6α-(1-aminoethyl)-3-carboxylate

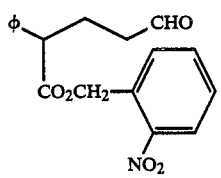

The product of Step B is dissolved in 1 ml dioxane 0.2 ml EtOH 1 ml H$_2$O 1 mg of 10% Pd/C catalyst is added and the mixture hydrogenated at 40 lbs. for 45 minutes. The catalyst is filtered and washed with a little water. The filtrate and washings are extracted 3× with EtOAc and the aqueous phase is freeze dried to give 1-carba-2-(p-methoxyphenyl)-2-penem-6α-(1-aminoethyl)-3-carboxylate.

U.V. λmax. 310 nm.

EXAMPLE 48

Step A

Preparation of o-nitrobenzyl-2-hydroxyethylphenyl acetate

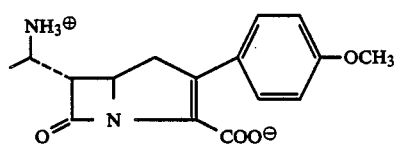

To a stirred mixture of 10 mmoles of 2-hydroxyethyl phenyl acetic acid and 10 mmoles of triethylamine in 25 ml of acetone is added 10 mmoles of solid o-nitrobenzyl bromide. The mixture is stirred overnight under nitrogen atmosphere and the insoluble materials removed by filtration. The filtrate is evaporated under reduced pressure and the residue obtained is partitioned between ethyl acetate and water. The organic phase is separated and is washed successively with dilute aqueous sodium bicarbonate solution and water, then dried (MgSO$_4$), filtered, and evaporated. The residue is purified by silica gel chromatography to provide the product.

Step B

Preparation of 2-o-nitrobenzylcarboxyhydroannamaldehyde

To a stirred suspension of pyridinium chlorochromate (1.0 mmoles) in 10 ml anhydrous methylene chloride is added in one portion a solution of the above alcohol, Step A, (0.66 mmoles) in 15 ml dry methylene chloride. The mixture is vigorously stirred at 25° C. under a nitrogen atmosphere for 3 hours. To the reaction mixture is added 50 ml of anhydrous diethyl ether and the solution is decanted away from the gummy residue. The residual tar is further extracted with Et$_2$O (3×25 ml). The extracts are combined and passed over a short column of ether-moist florisil eluting with Et$_2$O. The filtrate is evaporated to give the pure aldehyde product.

EXAMPLE 49

Following the procedures of the foregoing Examples and text, the following substituted azetidinone thioesters, useful in the preparation of the compounds of the present invention are obtained.

TABLE IV
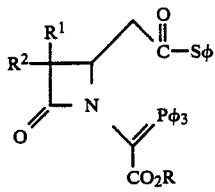
R = o-nitrobenzyl
φ = phenyl
| Compound | R₁ | R₂ |
|---|---|---|
| (1.) | (R)-CH₃-CH(O-C(=O)-O-CH₂-(2-NO₂-C₆H₄)) | H |
| (2.) | (S)-CH₃-CH(O-C(=O)-O-CH₂-(2-NO₂-C₆H₄)) | H |
| (3.) | H | CH₃-CH(O-C(=O)-O-CH₂-(2-NO₂-C₆H₄)) |
| (4.) | CH₃-CH₂-O-C(=O)-O-CH₂-(2-NO₂-C₆H₄) | H |
| (5.) | H | CH₃-CH₂-O-C(=O)-O-CH₂-(2-NO₂-C₆H₄) |
| (6.) | CH₃-CH(H)-NH-C(=O)-O-CH₂-(2-NO₂-C₆H₄) | H |
| (7.) | H | CH₃-CH(H)-NH-C(=O)-O-CH₂-(2-NO₂-C₆H₄) |
| (8.) | CH₃-CH₂-NH-C(=O)-O-CH₂-(2-NO₂-C₆H₄) | H |

TABLE IV-continued

| | | |
|---|---|---|
| (9.) | 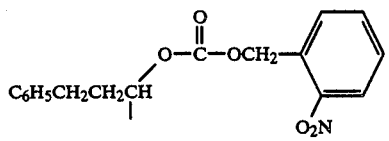 | H |
| (10.) | 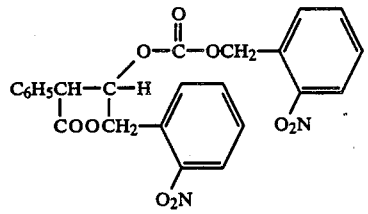 | H |
| (11.) | 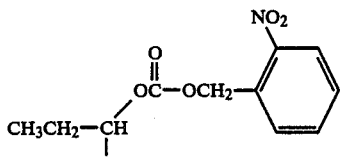 | H |

FOOTNOTES TO TABLE IV
(1.) Starting with the (R) isomer from Step A, Example 45 and using the procedures described in Steps B to H.
(2.) As described in Example 45 Steps A to Step H.
(3.) By the procedure of Example 45, Steps A to H starting with the product of Example 8, Step E (β-isomer).
(4.) Starting with the product of Step D, Example 8 and following the procedure of Step E, Example 8, but substituting formaldehyde instead of acetaldehyde and using the product as starting material for the procedures described in Example 45, Steps A to H.
(5.) Same as 4 except that the β-product is used for the procedures described in Example 45 Steps A to H.
(6.) As described in Example 46, Steps A to C
(7.) As described in Example 43, Steps A to I and Example 46, Steps A to C, but starting with the product of Example 8, Step E (β-isomer).
(8.) From the product obtained from Step E example 8 wherein formaldehyde is substituted for acetaldehyde and using the products described in Example 43 Steps A to I, Example 46 Steps A to C.
(9.) From the product obtained from Step E, Example 8 wherein hydrocinamaldehyde is substituted for acetaldehyde and following the procedures described in Example 45, Steps A to H.
(10.) From the product obtained from Step E Example 8 wherein the aldehyde product of Example 48 Step B is used instead of acetaldehyde and following the procedures described in Example 45, Step A to H.
(11.) From the product obtained from Step E, Example 8 where propionaldehyde is used instead of acetaldehyde and using the procedure described in Example 45, Steps A to H.

EXAMPLE 50

Following the procedures developed in the foregoing Examples and text, the following compounds of the present invention, I, are obtained. Remarks relative to the procedures are presented in the footnote to Table V. Table V is complementary to the Table of Example 38, above.

TABLE V $$\text{structure with } R^1, R^2, R^3, \text{COOR}$$

| Compound | $R^1$ | $R^2$ | $R^3$ | R |
|---|---|---|---|---|
| (1.) | CH₃—C(OH)(H)— | H | —C₆H₄—OCH₃ | Na |
| (2.) | CH₃—C(NH₂)(H)— | H | —C₆H₅ | H |
| (3.) | CH₃—C(OH)(H)— | H | —C₆H₄—CH₂—N(CH₃)₂ | H |

TABLE V-continued

Structure I:

R¹ with R² and H on one carbon, connected to C=O, N ring, with R³ and COOR on the double bond side.

| Compound | R¹ | R² | R³ | R |
|---|---|---|---|---|
| (4.) | CH₃–C(OH)(H)– | H | –C₆H₄–CH₂OH | Na |
| (5.) | CH₃–C(OH)(H)– | H | –C₆H₄–COONa | Na |
| (6.) | CH₃–C(OH)(H)– | H | –C₆H₄–CH₂–NH–CH₃ | H |
| (7.) | CH₃–C(OH)(H)– | H | –C₆H₄–CH₂–NH₂ | H |
| (8.) | CH₃–C(OH)(H)– | H | –C₆H₄–CH₂–NH–CH(CH₃)₂ | H |
| (9.) | CH₃–C(OH)(H)– | H | –C₆H₄–N(CH₃)₂ | H |
| (10.) | CH₃–C(OH)(H)– | H | –C₆H₄(o-CH₂–N(CH₃)₂) | H |
| (11.) | CH₃–C(OH)(H)– | H | –C₆H₄–CH₂–COONa | Na |
| (12.) | CH₃–C(OH)(H)– | H | –C₆H₄(o-CH₂OH) | Na |
| (13.) | CH₃–C(OH)(H)– | H | –C₆H₄(o-CH₂COONa) | Na |
| (14.) | CH₃–C(OH)(H)– | H | –C₆H₄–C(=O)–OCH₂CH₂–NH₂ | H |

TABLE V-continued

Structure I: R¹-C(R²)(H)-C(=O)-N-[ring]-CH=C(R³)-COOR

| Compound | R¹ | R² | R³ | R |
|---|---|---|---|---|
| (15.) | CH₃–C(OH)(H)– | H | –C₆H₄–C(=O)–NH–CH₂CH₂NH₂ (para) | H |
| (16.) | CH₃–C(OH)(H)– | H | –C₆H₄–COONa (meta) | Na |
| (17.) | CH₃–C(H)(OH)– | H | –C₆H₄–CH₂–N=C(NH₂)(H) (para, guanidine-type) | H |
| (18.) | (CH₃)₂C(H)–OH | H | –C₆H₄–CH₂–N=C(NH₂)(CH₃) (para) | H |
| (19.) | CH₃–C(OH)(H)– | H | –C₆H₄–CH₂–N(CH₃)–C(=NH)(H) (para) | H |
| (20.) | CH₃–C(OH)(H)– | H | –C₆H₄–CH₂–N(iPr)–C(=NH)(H) (para) | H |
| (21.) | CH₃–C(H)(OH)– | H | –C₆H₄–N(H)–C(=NH)(CH₃) | H |
| (22.) | CH₃–C(H)(OH)– | H | –CH=CH–CH₃ (cis) | Na |
| (23.) | CH₃–C(H)(OH)– | H | –C(CH₃)=CH–CH₂–NH₂ | H |
| (24.) | CH₃–C(H)(OH)– | H | –C(CH₃)=CH₂ | Na |
| (25.) | CH₃–C(H)(OH)– | H | –C(CH₃)=CH–CH₂–N(H)–CH₃ | H |
| (26.) | CH₃–C(H)(OH)– | H | –C(CH₃)=C(CH₃)₂ | Na |

TABLE V-continued

| Compound | R¹ | R² | R³ | R |
|---|---|---|---|---|
| (27.) | CH₃-C(H)(OH)- | H | C(=CH₂)(C₆H₅)- | Na |
| (28.) | CH₃-C(H)(OH)- | H | -C(CH₃)=CH-CH₂-N(Et)₂ (cis) | H |
| (29.) | CH₃-C(H)(OH)- | H | -C(CH₃)=CH-CH₂-OEt | Na |
| (30.) | CH₃-C(H)(OH)- | H | -CH=CH-C₆H₅ | Na |
| (31.) | CH₃-C(H)(OH)- | H | 1-cycloheptenyl | Na |
| (32.) | CH₃-C(H)(OH)- | H | -C≡CH | Na |
| (33.) | CH₃-C(H)(OH)- | H | -C≡C-CH₂NH₂ | H |
| (34.) | CH₃-C(H)(OH)- | H | 1-naphthyl | Na |
| (35.) | CH₃-C(H)(OH)- | H | 4-pyridyl | H |
| (36.) | CH₃-C(H)(OH)- | H | 2-pyridyl | H |
| (37.) | CH₃-C(H)(OH)- | H | 5-methyl-2-furyl | Na |
| (38.) | CH₃-C(H)(OH)- | H | 2-thienyl | Na |

TABLE V-continued

| Compound | R¹ | R² | R³ | R |
|---|---|---|---|---|
| (39.) | CH₃ / OH | H | (3-thienyl) | Na |
| (40.) | CH₃ / OH | H | (isothiazolyl) | Na |
| (41.) | CH₃ / OH | H, CH₃ | (dimethylthiazolyl) | Na |
| (42.) | CH₃ / OH | H | (thiazolyl) | Na |
| (43.) | CH₃ / OH | H | (1-methylpyrazolyl) | H |
| (44.) | CH₃ / OH (inverted) | H | (1-methylpyrazolyl) | Na |
| (45.) | CH₃ / OH (inverted) | H | (1-methylimidazolyl) | H |
| (46.) | CH₃ / OH (inverted) | H | (1-methylpyrrolyl) | H |
| (47.) | CH₃ / OH (inverted) | H | (trimethylpyrazinyl) | H |
| (48.) | CH₃ / OH (inverted) | H | (1-methyltetrazolyl) | Na |
| (49.) | —CH₂—OH | H | (phenyl) | Na |

TABLE V-continued

Structure I: R¹ at position with R² and H, ring with C=O, N, and =C(R³)-COOR

| Compound | R¹ | R² | R³ | R |
|---|---|---|---|---|
| (50.) | —CH₂—OH | H | —C₆H₄—CH₂—N(CH₃)₂ (para) | H |
| (51.) | —CH₂OH | H | —C₆H₄—CH₂OH (para) | Na |
| (52.) | —CH₂—OH | H | —C₆H₄—COONa (para) | Na |
| (53.) | —CH₂OH | H | —C₆H₄—CH₂—NH₂ (para) | H |
| (54.) | —CH₂OH | H | —C₆H₄—CH₂N—C(CH₃)₂ (para) | H |
| (55.) | —CH₂OH | H | —C₆H₄—CH₂—N=C(NH₂)(H) (para) | H |
| (56.) | —CH₂OH | H | —C₆H₄—CH₂—N=C(NH₂)(CH₃) (para) | H |
| (57.) | —CH₂—OH | H | —C₆H₄—CH₂—N(H)—C(H)=NCH₃ (para) | H |
| (58.) | —CH₂OH | H | —C₆H₄—CH₂N=C(H)—N< (para) | H |
| (59.) | —CH₂OH | H | CH₃—CH=CH— | Na |
| (60.) | —CH₂OH | H | CH₃—C(H)=C(H)—N(H)—CH₃ | H |
| (61.) | —CH₂OH | H | C₆H₅—C(H)=C(H)— | Na |

TABLE V-continued $$\underset{O}{\overset{R^2\;H}{\underset{N}{R^1}}}\diagdown\diagup\overset{R^3}{\underset{COOR}{}}\quad I$$

| Compound | R¹ | R² | R³ | R |
|---|---|---|---|---|
| (62.) | —CH₂OH | H | 1-cycloheptenyl | Na |
| (63.) | —CH₂OH | H | —C≡C—CH₂—NH₂ | H |
| (64.) | —CH₂OH | H | 4-pyridyl | H |
| (65.) | —CH₂OH | H | 2-pyridyl | H |
| (66.) | —CH₂OH | H | 3-thienyl | Na |
| (67.) | —CH₂OH | H | benzo[b]thien-2-yl | Na |
| (68.) | —CH₂OH | H | 2,4,5-trimethylthiazol-? (4,5-dimethyl-2-methylthiazolyl) | Na |
| (69.) | —CH₂OH | H | 1-methyl-pyrazol-5-yl | H |
| (70.) | —CH₂OH | H | 1,5-dimethyl-tetrazol-? | Na |
| (71.) | CH₃CH(NH₂)— | H | 4-methoxyphenyl | H |
| (72.) | CH₃CH(NH₂)— | H | 4-(hydroxymethyl)phenyl | H |
| (73.) | CH₃CH(NH₂)— | H | 4-carboxyphenyl | Na |

TABLE V-continued

Structure I: R¹-C(R²)(H)-C(=O)-N(ring)-C(=CH-R³)-COOR

| Compound | R¹ | R² | R³ | R |
|---|---|---|---|---|
| (74.) | CH₃-C(NH₂)(H)- | H | -C₆H₄-CH₂-N(CH₃)₂ (para) | H |
| (75.) | CH₃-C(NH₂)(H)- | H | -C(CH₃)=CH- (with H's) | H |
| (76.) | CH₃-C(NH₂)(H)- | H | -CH=CH-CH₂-N(Et)₂ | H |
| (77.) | CH₃-C(NH₂)(H)- | H | cycloheptenyl | H |
| (78.) | CH₃-C(NH₂)(H)- | H | 5-methyl-furan-2-yl | — |
| (79.) | CH₃-C(NH₂)(H)- | H | 5-methyl-isothiazol-3-yl | H |
| (80.) | CH₃-C(NH₂)(H)- | H | thiazol-2-yl | H |
| (81.) | CH₃-C(NH₂)(H)- | H | 1-methyl-tetrazol-5-yl | H |
| (82.) | C₆H₅CH₂CH₂-C(OH)(H)- | H | -C₆H₄-OCH₃ (para) | Na |
| (83.) | C₆H₅CH₂CH₂-C(OH)(H)- | H | -C₆H₄-CH₂-N(CH₃)₂ | H |
| (84.) | C₆H₅CH₂CH₂-C(OH)(H)- | H | -C₆H₄-CH₂OH (para) | Na |
| (85.) | C₆H₅CH₂CH₂-C(OH)(H)- | H | -C₆H₄-COONa (para) | Na |

TABLE V-continued

| Compound | R¹ | R² | R³ | R |
|---|---|---|---|---|
| (86.) | C₆H₅CH₂CH₂–C(OH)(H)– | H | –C₆H₄–CH₂–NH₂ (para) | Na |
| (87.) | C₆H₅CH₂CH₂–C(OH)(H)– | H | –C₆H₄–CH₂–N=C(H)(NH₂) (para) | H |
| (88.) | C₆H₅CH₂CH₂–C(OH)(H)– | H | –C₆H₄–NH–C(CH₃)=NH (para) | H |
| (89.) | C₆H₅CH₂CH₂–C(H)(OH)– | H | –C(CH₃)=CH–H (cis) | Na |
| (90.) | C₆H₅CH₂CH₂–C(H)(OH)– | H | –C(CH₃)=C(H)–CH₂–NH₂ | Na |
| (91.) | C₆H₅CH₂CH₂–C(H)(OH)– | H | –C(CH₃)=C(H)–CH₂–OH | Na |
| (92.) | C₆H₅CH₂CH₂–C(H)(OH)– | H | 4-pyridyl | H |
| (93.) | C₆H₅CH₂CH₂–C(H)(OH)– | H | 2-thienyl | Na |
| (94.) | C₆H₅CH₂CH₂–C(H)(OH)– | H | N-methylisothiazolyl | Na |
| (95.) | C₆H₅CH₂CH₂–C(H)(OH)– | H | N-methylpyrazolyl | H |
| (96.) | C₆H₅CH₂CH₂–C(H)(OH)– | H | N-methylpyrrolyl | H |
| (97.) | C₆H₅CH(COONa)–CH₂–C(OH)(H)– | H | –C₆H₄–OCH₃ (para) | Na |

TABLE V-continued

Structure I:
$R^1$-C($R^2$)(H)-C(H)(•)-C(•)(=N-...)-C(R^3)=...-COOR, with β-lactam (C=O, N) ring.

| Compound | $R^1$ | $R^2$ | $R^3$ | R |
|---|---|---|---|---|
| (98.) | $C_6H_5CH(COONa)-CH_2-C(OH)(CH_3)-$ | H | 4-($(CH_3)_2NCH_2$)-$C_6H_4$- | H |
| (99.) | $C_6H_5CH(COONa)-CH_2-C(OH)(CH_3)-$ | H | 4-($CH_3NHCH_2$)-$C_6H_4$- | H |
| (100.) | $C_6H_5CH(COONa)-CH_2-C(OH)(CH_3)-$ | H | 4-($H_2NCH_2$)-$C_6H_4$- | H |
| (101.) | $C_6H_5CH(COONa)-CH_2-C(OH)(CH_3)-$ | H | 4-($(CH_3)_2N$)-$C_6H_4$- | H |
| (102.) | $C_6H_5CH(COONa)-CH_2-C(OH)(CH_3)-$ | H | 3-($(CH_3)_2NCH_2$)-$C_6H_4$- | H |
| (103.) | $C_6H_5CH(COONa)-CH_2-C(OH)(CH_3)-$ | H | 4-[$CH_2-N=C(CH_3)(NH)$]-$C_6H_4$- | H |
| (104.) | $C_6H_5CH(COONa)-CH_2-C(OH)(CH_3)-$ | H | 4-[$CH_2-N(CH_3)-CH=NH$]-$C_6H_4$- | H |
| (105.) | $C_6H_5CH(COONa)-CH_2-C(OH)(CH_3)-$ | H | 4-[$CH_2-N(iPr)-CH=NH$]-$C_6H_4$- | H |
| (106.) | $C_6H_5CH(COONa)-CH_2-C(OH)(CH_3)-$ | H | $(CH_3)_2C=C(CH_3)-$ | Na |
| (107.) | $C_6H_5CH(COONa)-CH_2-CH(OH)-$ | H | $CH_3-C(=CHCH_2NH_2)-$ | H |
| (108.) | $C_6H_5CH(COONa)-CH_2-CH(OH)-$ | H | $-CH=CH-CH_2-N(Et)_2$ | H |
| (109.) | $C_6H_5CH(COONa)-CH_2-CH(OH)-$ | H | $-C\equiv C-H$ | Na |

TABLE V-continued

Structure I:

$$R^1-C(R^2)(H)-C(=O)-N-CH=C(R^3)-COOR$$

(β-lactam ring with R¹ on C adjacent to C=O, R² and H on the other ring carbon, R³ on the vinyl carbon bearing COOR)

| Compound | R¹ | R² | R³ | R |
|---|---|---|---|---|
| (110.) | C₆H₅CH(COONa)—CH₂—C(OH)(H)— | H | 4-pyridyl | H |
| (111.) | C₆H₅CH(COONa)—CH₂—C(OH)(H)— | H | 2-pyridyl | H |
| (112.) | C₆H₅CH(COONa)—CH₂—C(OH)(H)— | H | benzo[b]thiophen-2-yl | Na |
| (113.) | C₆H₅CH(COONa)—CH₂—C(OH)(H)— | H | 1,3-thiazol-2-yl | Na |
| (114.) | C₆H₅CH(COONa)—CH₂—C(OH)(H)— | H | 1-methyl-5-methylpyrazol-3-yl (1-CH₃-pyrazolyl with CH₃) | H |
| (115.) | C₆H₅CH(COONa)—CH₂—C(OH)(H)— | H | 3,5,6-trimethylpyrazin-2-yl | H |
| (116.) | C₆H₅CH(COONa)—CH₂—C(OH)(H)— | H | 1-methyl-1H-tetrazol-5-yl (N-CH₃ tetrazolyl) | Na |
| (117.) | CH₃—CH₂—C(OH)(H)— | H | C₆H₅— (phenyl) | Na |
| (118.) | CH₃—CH₂—C(OH)(H)— | H | 4-(N,N-dimethylaminomethyl)phenyl | H |
| (119.) | CH₃—CH₂—C(OH)(H)— | H | 4-(hydroxymethyl)phenyl | Na |
| (120.) | CH₃—CH₂—C(OH)(H)— | H | 2-(hydroxymethyl)phenyl | Na |
| (121.) | CH₃—CH₂—C(OH)(H)— | H | 4-(COONa)phenyl | Na |

TABLE V-continued

| Compound | R¹ | R² | R³ | R |
|---|---|---|---|---|
| (122.) | CH₃—CH₂—C(OH)(H)— | H | (2-COONa-phenyl) | Na |
| (123.) | CH₃—CH₂—C(OH)(H)— | H | (4-CH₂—NH—CH₃-phenyl) | H |
| (124.) | CH₃—CH₂—C(OH)(H)— | H | (4-CH₂—NH₂-phenyl) | H |
| (125.) | CH₃—CH₂—C(OH)(H)— | H | (4-CH₂—N=C(NH₂)(H)-phenyl) | H |
| (126.) | CH₃CH₂—C(OH)(H)— | H | (4-CH₂—N=C(NH₂)(iPr)-phenyl) | H |
| (127.) | CH₃—CH₂—C(OH)(H)— | H | (4-CH₂—N(CH₃)—C(=NH)(NH)-phenyl) | H |
| (128.) | CH₃—CH₂—C(OH)(H)— | H | (CH₃)(=CH₂)C— | Na |
| (129.) | CH₃—CH₂—C(OH)(H)— | H | CH₃—C=C(H)(NH₂)— | H |
| (130.) | CH₃—CH₂—C(OH)(H)— | H | 4-pyridyl | H |
| (131.) | CH₃—CH₂—C(OH)(H)— | H | 2-thienyl | Na |
| (132.) | CH₃—CH₂—C(OH)(H)— | H | 2-thiazolyl | Na |
| (133.) | CH₃—CH₂—C(OH)(H)— | H | 1-methyl-2-pyrrolyl | H |

TABLE V-continued

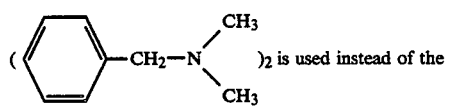

| Compound | R¹ | R² | R³ | R |
|---|---|---|---|---|
| (134.) | CH₃—CH₂—C(OH)(H) | H | CH₃, N—N / N=N (tetrazolyl-methyl) | Na |

FOOTNOTE TO TABLE V
(1.) Starting with compound 1, 2 or 3 of Table IV and following the procedures of Example 45, Steps I to K.
(2.) Example 46
(3.) Starting with compound 1, 2 or 3 of Table IV and following the procedure of Example 45, Steps I to K except that 1 eq of LiCu

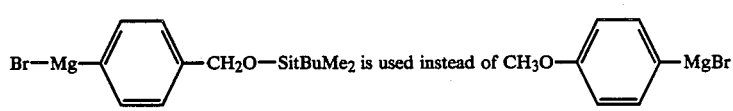

)₂ is used instead of the

Grignard reagent. —CuI complex in Step I.
(4.) Starting with compound 1, 2 or 3 of Table IV and following the procedure of Example 45, Steps I to K except that

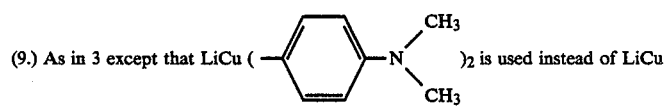

in Step I followed by hydrolysis of the silyl protecting group before cyclization.
(5.) From 1-(o-nitrobenzyloxycarbonyltriphenylphosphoranylmethyl)-3-[1-o-nitrobenzyl-oxycarbonyloxyethyl)-4-(p-hydroxymethylphenylcarbonylmethyl)-2-azetidinone (A) prepared as an intermediate for comp. 4, by oxidation of the alcohol to the corresponding acid by Jones Reagent, protection of the acid function as a o-nitrobenzyl ester, followed by cyclization and deprotection as in Steps J & K of Example 45.
(6.) From (A) in 5, by conversion to the mesylate to the chloro derivative, and displacement with CH₃NH₂ followed by cyclization of the methyl amino ketone and deprotection as in Steps J and K of Example 45.
(7.) From the mesylate or chloro derivative in 6 by displacement with NaN₃ and reduction of the azide formed to the amine, followed by cyclization and deprotection as in Steps J & K of Example 45. Optionally, the amine may be protected as a o-nitrobenzyl carbamate before cyclization; or the keto-azide itself may be cyclized, followed by reductive deprotection.
(8.) As for 6 except that the mesylate is displaced with isopropylamine instead of CH₃NH₂.

(9.) As in 3 except that LiCu ( 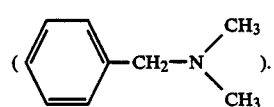 )₂ is used instead of LiCu

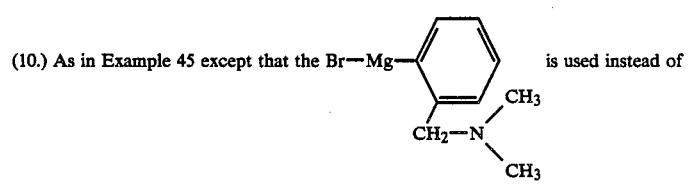

(10.) As in Example 45 except that the Br—Mg— 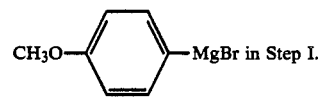 is used instead of

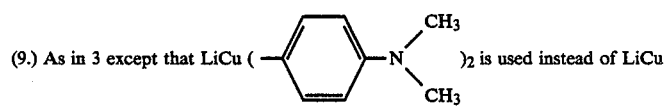

CH₃O—⟨⟩—MgBr in Step I.

TABLE V-continued

| Compound | R¹ | R² | R³ | R |
|---|---|---|---|---|

(11.) As for comp. 5 using Br—Mg—C₆H₄—CH₂—CH₂O SitBuMe₂ as the Grignard reagent.

(12.) As in 4 using the ortho isomer of the Grignard reagent.

(13.) As for comp. 11 using the ortho isomer of the Grignard reagent.

(14.) From 1-(o-nitrobenzyloxycarbonyltriphenylphosphoranylmethyl-3-(1-o-nitrobenzyl-oxycarbonyloxyethyl)-4-(p-carboxyphenylcarbonylmethyl)-2-azetidinone which is an intermediate for comp. 5, by esterification with 2-(o-nitrobenzyloxycarbonylamino)-ethanol, followed by cyclization and deblocking as in Steps J & K as in example 45.

(15.) As for comp. 14 except that the acid is converted to the amide of 2-(o-nitrobenzyloxycarbonylamino)-ethylamine.

(16.) As for comp. 5 except that the meta isomer of the Grignard reagent is used.

(17.) From compound 7, by treatment with 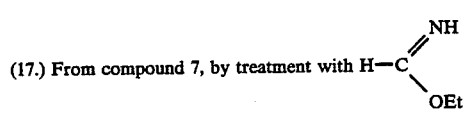

(18.) From compound 7, by treatment with 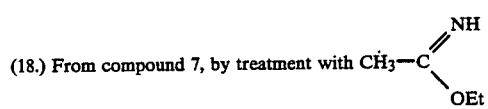

(19.) From compound 6, by treatment with 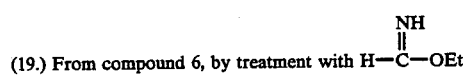

(20.) From compound 8, by treatment with 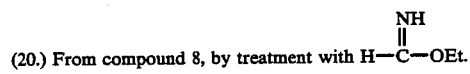

(21.) Starting with compound 1, 2 or 3 of Table IV and following the procedure of example 45, Steps I to K except that 1 eq of LiCu

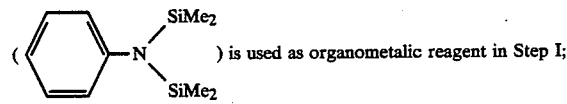 ) is used as organometalic reagent in Step I;

and amidination of the product with 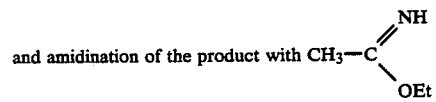

(22.) Starting with compd. 1, 2 or 3 of Table IV and following the procedure of Example 45, Steps I to K except that Cl—Mg—CH=CH₂ 

is used instead of CH₃O—C₆H₄—MgBr in Step I.

(23.) As for compd. 3 except that 1 eq of LiCu

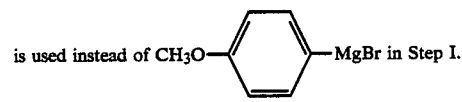 is used as the organomatlic reagent in Step I.

(24.) As for compd. 22 using  as the Grignard reagent.

TABLE V-continued

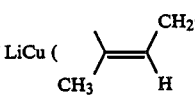

| Compound | R¹ | R² | R³ | R |
|---|---|---|---|---|

(25.) As for compd. 23 using 1 eq. of LiCu ( 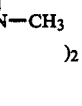 )₂ in Step I.

(26.) As for compd. 22 using ClMg 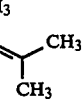

(27.) As for compd. 22 using Cl—Mg 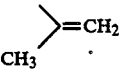

(28.) As for compd. 23 using LiCu ( 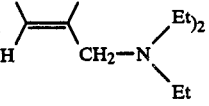 )₂

(29.) As for compd. 23 using LiCu ( 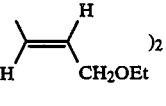 )₂

(30.) As for compd. 23 using LiCu ( 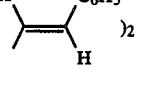 )₂

(31.) As for compd. 23 using LiCu ( 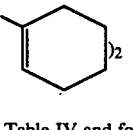 )₂

(32.) Starting with compd. 1 or 2 of Table IV and following the procedures of Example 45 Steps I to K except that 2 eq of LiCu (—C≡CH)₂ are used instead of the Grignard reagent CuI complex in Step I.

(33.) As for compd 32 using LiCu (—C≡C—CH₂—N 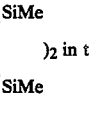 )₂ in the procedure of Step I example 45.

(34.) As for compd. 1 using Br—Mg— 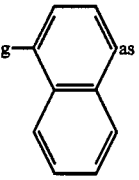 as the Grignard reagent in Step I.

(35.) As for compd 3 using LiCu (— 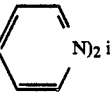 N)₂ in procedure of Step I.

(36.) As for compd. 3 using LiCu ( 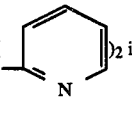 )₂ in the procedure of Step I.

TABLE V-continued $$\text{structure I: } R^1-C(=O)-N \text{ ring with } R^2, H, R^3, \text{COOR substituents}$$

| Compound | R¹ | R² | R³ | R |
|---|---|---|---|---|

(37.) As for compd 3 using LiCu (—[furan-CH₃])₂ in the procedure of Step I.

(38.) As for compd. 3 using LiCu ([thiophene])₂ in the procedure of Step I.

(40.) As for compd. 3 using LiCu ([thiazole])₂ in the procedure of Step I.

(41.) As for compd. 3 using LiCu ([dimethyl-thiazole with CH₃ groups])₂ in the procedure of Step I.

(42.) As for compd. 3 using LiCu ([thiazole isomer])₂ in the procedure of Step I.

(43.) As for compd. 3 using LiCu ([N-methylpyrazole])₂ in the procedure of Step I.

(44.) As for compd. 3 using LiCu ([N-methylpyrazole isomer])₂ in the procedure of Step I.

(45.) As for compd. 1 using BrMg—[N-methylimidazole] as the Grignard reagent of Step I.

(46.) As for compd. 3 using LiCu ([N-methylpyrrole])₂ in the procedure of Step I.

(47.) As for compd. 3 using LiCu ([dimethylpyrazine])₂ in the procedure of Step I.

(48.) As for compd. 3 using LiCu (—[N-methyl triazole])₂ in the procedure of Step I.

(49.) Starting with compd. 4 or 5 of Table IV and following the procedure of Example 45, Steps I to K using C₆H₅MgBr as the Grignard reagent in Step I.
(50.) As described for compd. 3 but starting with compd 4 or 5 of Table IV.
(51.) As described for compd. 4 but starting with compd. 4 or 5 of Table IV.
(52.) As described for compd. 5 but starting with compd 4 or 5 of Table IV.

TABLE V-continued

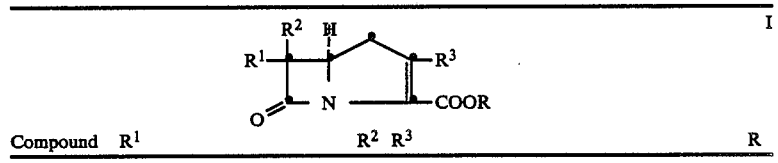

Compound  R¹  R²  R³  R (54.) As described for compd. 8 but starting with compd. 4 or 5 of Table IV.
(55.) As described for compd. 17 but starting with compd. 53.
(56.) As described for compd. 18 but starting with compd 53

(57.) Starting with compd. 53 using H—C(=N—CH₃)(OEt) as the amidinating agent.

(58.) Starting with compd. 53 and following the procedure described for compd. 17 but using HC(=N—C(CH₃)(CH₃))(OEt) as the amidinating agent.

(59.) As for compd. 24 but starting with compd. 4 or 5 of Table IV.
(60.) As for compd. 25 but starting with compd. 4 or 5 of Table IV.
(61.) As for compd. 30 but starting with compd. 4 or 5 of Table IV.
(62.) As for compd. 31 but starting with compd. 4 or 5 of Table IV.
(63.) As for compd. 33 but starting with compd. 4 or 5 of Table IV.
(64.) As for compd. 35 but starting with compd. 4 or 5 of Table IV.
(65.) As for compd. 36 but starting with compd. 4 or 5 of Table IV.
(66.) As for compd. 39 but starting with compd. 4 or 5 of Table IV.
(67.) Starting with compd. 4 or 5 of Table IV and following the procedure of Example 45

Steps I to K using LiCu(benzothiophene)₂ as the organometallic reagent in Step I.

(68.) As for compd. 41 but starting with compd. 4 or 5 of Table IV.
(69.) As for compd. 43 but starting with compd. 4 or 5 of Table IV.
(70.) As for compd. 48 but starting with compd. 4 or 5 of Table IV.
(71.) Example 47.
(72.) As for compd. 4 but starting with compd. 6 or 7 of Table IV.
(73.) As for compd. 5 but starting with compd. 6 or 7 of Table IV.
(74.) As for compd 3 but starting with compd. 6 or 7 of Table IV.
(75.) As for compd 24 but starting with compd. 6 or 7 of Table IV.
(76.) As for compd. 28 but starting with compd 6 or 7 of Table IV.
(77.) As for compd 31, but starting with compd 6 or 7 of Table IV.
(78.) As for compd. 37 but starting with compd 6 or 7 of Table IV.
(79.) As for compd 40 but starting with compd 6 or 7 of Table IV.
(80.) As for compd 42 but starting with compd 6 or 7 of Table IV.
(81.) As for compd 48 but starting with compd 6 or 7 of Table IV.
(82.) As for compd 9 of Table IV and using the procedures of Steps I to K of Example 45.
(83.) As for compd 3 but starting with compd 9 of Table IV.
(84.) As for compd 4 but starting with compd 7 of Table IV.
(85.) As for compd 5 but starting with compd 9 of Table IV.
(86.) As for compd 7 but starting with compd. 9 of Table IV.

(87.) From compd 86 by treatment with H—C(=NH)(OEt).

(88.) As for compd 21 but starting with compd 9 of Table IV.
(89.) As for compd 24 but starting with compd 9 of Table IV.
(90.) As for compd 23 but starting with compd 9 of Table IV. and using 1 eq of LiCu(CH₃C=CH-Si(CH₃)₂-CH₂-N-Si(CH₃)₂)₂ organometalic reagent in Step I.

(91.) As for compd 22, but starting with compd 9 of Table IV and using

ClMg-C=C-OSitBuMe₂ as the Grignard reagent in Step I.

TABLE V-continued $$\text{structure I: } R^1\text{-C(=O)-N ring with } R^2, H, R^3, \text{COOR}$$

| Compound | $R^1$ | $R^2$ | $R^3$ | R |
|---|---|---|---|---|

(92.) As for compd 35 but starting with compd 9 of Table IV.
(93.) As for compd 38 but starting with compd 9 of Table IV.
(94.) As for compd 40 but starting with compd 9 of Table IV.
(95.) As for compd 44 but starting with compd 9 of Table IV.
(96.) As for compd 46 but starting with compd 9 of Table IV.
(97.) Starting with compd 10 of Table IV and following the procedures of Example 45 Steps J and K.
(98.) As for compd 3 but starting with compd. 10 of Table IV.
(99.) As for compd 6 but starting with compd 10 of Table IV.
(100.) As for compd 7 but starting with compd 10 of Table IV.
(101.) As for compd 9 but starting with compd 10 of Table IV.
(102.) As for compd 10 but starting with compd 10 of Table IV.

(103.) From compd 100 by treatment with 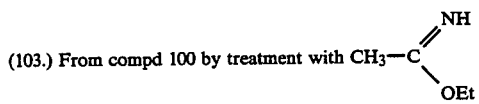

(104.) From compd 99 by treatment with 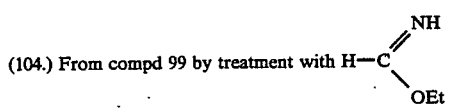

(105.) Starting with compd 10 of Table IV and following the procedures described for compd 8 and amidinating the resulting amine with 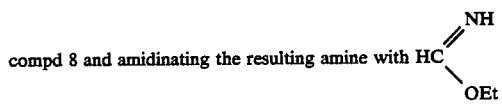

(106.) As for compd 26 but starting with compd 10 of Table IV.
(107.) As for compd 90 but starting with compd 10 of Table IV.
(108.) As for compd 28 but starting with compd 10 of Table IV.
(109.) As for compd 32 but starting with compd 10 of Table IV.
(110.) As for compd 35 but starting with compd 10 of Table IV.
(111.) As for compd 36 but starting with compd 10 of Table IV.
(112.) As for compd 67 but starting with compd 10 of Table IV.
(113.) As for compd 42 but starting with compd 10 of Table IV.
(114.) As for compd 43 but starting with compd 10 of Table IV.
(115.) As for compd 47 but starting with compd 10 of Table IV.
(116.) As for compd 48 but starting with compd 10 of Table IV.
(117.) Starting with compd 11 of Table IV and following the procedures of example 45 steps I to K but using $C_6H_5MgBr$ as the Grignard reagent in Step I.
(118.) As for compd 3 but starting with compd 11 of Table IV.
(119.) As for compd 4 but starting with compd 11 of Table IV.
(120.) As for compd 12 but starting with compd 11 of Table IV.
(121.) As for compd 5 but starting with compd 11 of Table IV.
(122.) Starting with compd 11 of Table IV and using the procedure described for compd 5 but using 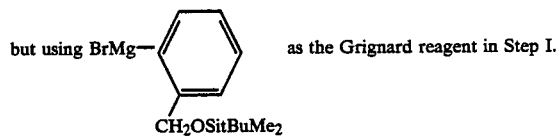 as the Grignard reagent in Step I.

(123.) As for compd 6 but starting with compd 11 of Table IV.
(124.) As for compd 7 but starting with compd. 11 of Table IV.

(125.) From compd 124 by amidination with 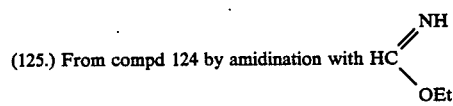

(126.) From compd 124 by amidination with 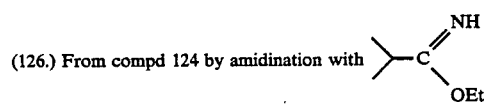

TABLE V-continued

Compound $R^1$ — $R^2$ $R^3$ — R (127.) From compd 123 by amidination with H—C(=NH)OEt (128.) As for compd 24 but starting with compd 11 of Table IV.
(129.) As for compd 90 but starting with compd 11 of Table IV.
(130.) As for compd 35 but starting with compd 11 of Table IV.
(131.) As for compd 38 but starting with compd 11 of Table IV.
(132.) As for compd 42 but starting with compd 11 of Table IV.
(133.) As for compd 46 but starting with compd 11 of Table IV.
(134.) As for compd 48 but starting with compd 11 of Table IV.

EXAMPLE 51

Preparation of Pharmaceutical Compositions

One such unit dosage form consists in mixing 120 mg. of 1-carba-2-(p-aminomethylphenyl)-6-(1'-hydroxyethyl)pen-2-em-3-carboxylic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
| --- | --- |
| 1-carba-2-(p-aminomethylphenyl)-6-(1'-hydroxyethyl)-pen-2-em-3-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
| --- | --- |
| Ampoule: | |
| 1-carba-2-(p-aminomethylphenyl)-6-(1'-hydroxyethyl)-pen-2-em-3-carboxylic acid | 500 mg. |
| Sterile Water | 2 ml. |
| OPTHALMIC SOLUTION | |
| 1-carba-2-(p-aminomethylphenyl)-6-(1'-hydroxyethyl)-pen-2-em-3-carboxylic acid | 100 mg. |
| Hydroxypropylmethyl cellulose | 5 mg. |
| Sterile Water to | 1 ml. |
| OTIC SOLUTION | |
| 1-carba-2-(p-aminomethylphenyl)-6-(1'-hydroxyethyl)-pen-2-em-3-carboxylic acid | 100 mg. |
| Benzalkonium Chloride | 0.1 mg. |

| -continued | |
| --- | --- |
| Sterile Water to | 1 ml. |
| TOPICAL OINTMENT | |
| 1-carba-2-(p-aminomethylphenyl)-6-(1'-hydroxyethyl)-pen-2-em-3-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

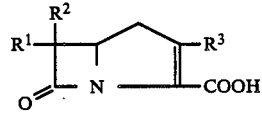

wherein:
$R^1$ is hydrogen;
$R^2$ is selected from the group consisting of:

$CH_3\overset{OH}{\underset{|}{CH}}-$, $HOCH_2-$, $(CH_3)_2\overset{OH}{\underset{|}{C}}-$, $(CH_3)_2CH-$, $CH_3CH_2-$, $CH_3-$, $CF_3CH(OH)$, $CH_3\overset{NH_2}{\underset{|}{CH}}$, and $C_1-C_6$ alkyl, substituted by fluoro; and $R^3$ is unsaturated heterocyclyl, wherein the heterocyclic structure is substituted or unsubstituted mono- or bicyclic and comprises 5 to 10 atoms, one or more of which is selected from oxygen, sulphur and nitrogen, and wherein the substituent or substituents are selected from the group consisting of $C_1-C_6$ alkyl, amino, hydroxyl, alkoxy having from 1 to 6 carbon atoms, 1 to 6 carbon atoms, mercapto, alkylthio having from 1 to 6 carbon atoms, mercapto, alkylthio having from 1 to 6 carbon atoms, sulfamoyl, amidino, guanidino, nitro, chloro, bromo, fluoro, cyano and carboxyl; with the proviso that
R³ is attached to the carbapenem ring via a heterocyclic ring carbon atom.

2. The compound of claim 1 wherein R³ is selected from the group consisting of:

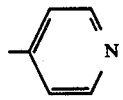 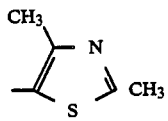

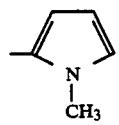 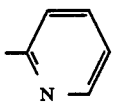

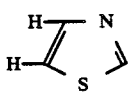 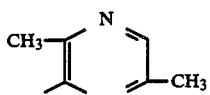

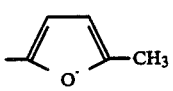 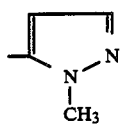

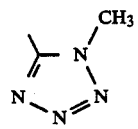 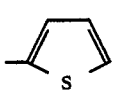

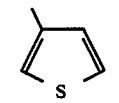 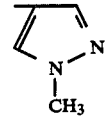

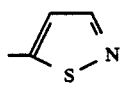 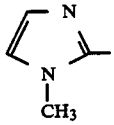

3. A compound according to claim 1 wherein R² is

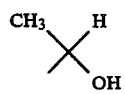

and R³ is

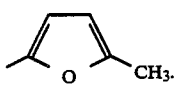

4. A compound according to claim 1 wherein R² is

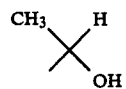

and R³ is

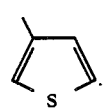

5. A compound according to claim 1 wherein R² is

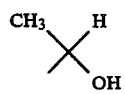

and R³ is

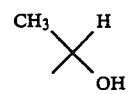

6. A compound according to claim 1 wherein R² is

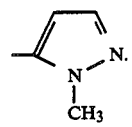

and R³ is

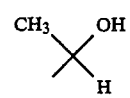

7. A compound according to claim 1 wherein R² is —CH₂OH and R³ is

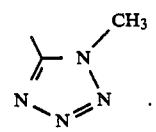

8. A compound according to claim 1 wherein R² is —CH₂OH and R³ is

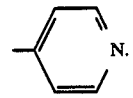

9. A compound according to claim 1 wherein R² is —CH₂OH and R³ is

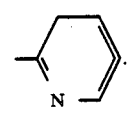

10. A compound according to claim 1 wherein R² is —CH₂OH and R³ is

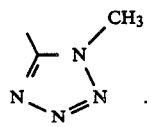

11. A compound according to claim 1 wherein $R^2$ is

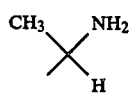

and $R^3$ is

12. A compound according to claim 1 wherein $R^2$ is

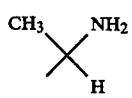

and $R^3$ is

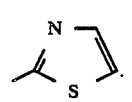

13. A compound according to claim 1 wherein $R^2$ is

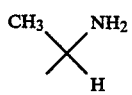

and $R^3$ is

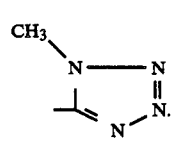

14. A compound according to claim 1 wherein $R^2$ is

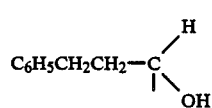

and $R^3$ is

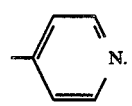

15. A compound according to claim 1 wherein $R^2$ is

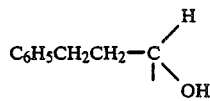

and $R^3$ is

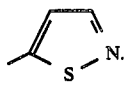

16. A compound according to claim 1 wherein $R^2$ is

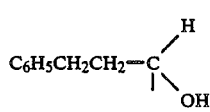

and $R^3$ is

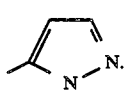

17. A compound according to claim 1 wherein $R^2$ is

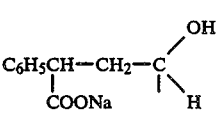

and $R^3$ is

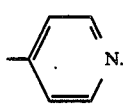

18. A compound according to claim 1 wherein $R^2$ is

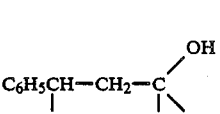

and $R^3$ is

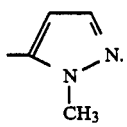

19. A compound according to claim 1 wherein $R^2$ is

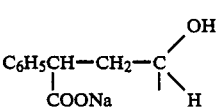

and $R^3$ is

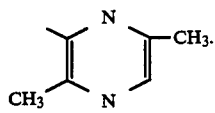

20. A compound according to claim 1 wherein $R^2$ is

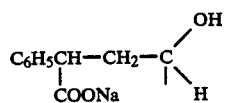

and $R^3$ is

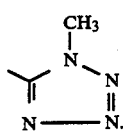

21. A compound according to claim 1 wherein $R^2$ is

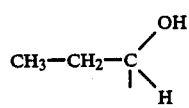

and $R^3$ is

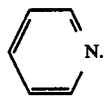

22. A compound according to claim 1 wherein $R^2$ is

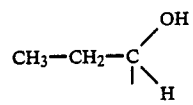

and $R^3$ is

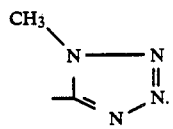

23. A compound according to claim 1 wherein $R^2$ is $CF_3CH(OH)$— and $R^3$ is

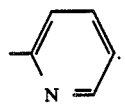

24. A compound according to claim 1 wherein $R^2$ is $CF_3CH(OH)$— and $R^3$ is

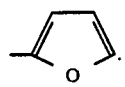

25. A compound according to claim 1 wherein $R^2$ is $CF_3CH(OH)$— and $R^3$ is

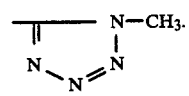

26. A pharmaceutical antibiotic composition comprising a compound according to claim 1 and a pharmaceutical carrier therefor.

27. A pharmaceutical antibiotic compositions comprising, in unitary dosage form, a therapeutically effective amount of a compound according to claim 1 and a pharmaceutical carrier therefor.

* * * * *